(12) United States Patent
Wilson et al.

(10) Patent No.: US 8,883,820 B2
(45) Date of Patent: Nov. 11, 2014

(54) TRIAZOLE DERIVATIVES AS KINASE INHIBITORS

(75) Inventors: Francis Wilson, Welwyn Garden (GB); Nigel Ramsden, Fowlmere Royston (GB); Kathryn Bell, London (GB); Andrew Cansfield, Harston (GB); Svenja Burckhardt, Boxworth (GB); Jess Taylor, Hitchin (GB); Mihiro Sunose, Sawston (GB); David Middlemiss, Bishops Stortford (GB)

(73) Assignee: Cellzome Ltd., Brentford, Middlesex (GB)

( * ) Notice: Subject to any disclaimer, the term of this patent is extended or adjusted under 35 U.S.C. 154(b) by 1083 days.

(21) Appl. No.: 12/438,662

(22) PCT Filed: Aug. 30, 2007

(86) PCT No.: PCT/EP2007/059051
§ 371 (c)(1),
(2), (4) Date: Mar. 23, 2010

(87) PCT Pub. No.: WO2008/025821
PCT Pub. Date: Mar. 6, 2008

(65) Prior Publication Data
US 2010/0227800 A1 Sep. 9, 2010

(30) Foreign Application Priority Data

Aug. 30, 2006 (EP) .................................... 06119831
May 23, 2007 (EP) .................................... 07108769

(51) Int. Cl.
*A61K 31/437* (2006.01)
*C07D 471/04* (2006.01)

(52) U.S. Cl.
CPC .................................... *C07D 471/04* (2013.01)
USPC ........................................ 514/303; 546/119

(58) Field of Classification Search
USPC ........................................ 514/303; 546/119
See application file for complete search history.

(56) References Cited

U.S. PATENT DOCUMENTS

| 6,514,989 B1 * | 2/2003 | Nettekoven et al. .......... 514/303 |
| 2010/0035756 A1 | 2/2010 | Luthy et al. |
| 2011/0021497 A1 | 1/2011 | Ramsden et al. |
| 2012/0135421 A1 | 5/2012 | Bell et al. |

FOREIGN PATENT DOCUMENTS

| DE | 287 263 A5 | 2/1991 |
| EP | 1 887 359 A1 | 2/2008 |
| MX | 2009/002171 A | 5/2009 |
| WO | 96/31517 A1 | 10/1996 |
| WO | 03/010167 A1 | 2/2003 |
| WO | 2004/072072 A | 8/2004 |
| WO | 2006/018735 A2 | 2/2006 |
| WO | 2006/038116 A2 | 4/2006 |
| WO | WO 2006/038116 * | 4/2006 .................... 546/119 |
| WO | 2006134056 A1 | 12/2006 |
| WO | WO 2007/095588 A1 | 8/2007 |
| WO | 2008006540 A1 | 1/2008 |
| WO | 2008015013 A1 | 2/2008 |
| WO | WO 2008/025821 A1 | 3/2008 |
| WO | 2009010530 A1 | 1/2009 |
| WO | WO 2009/068482 A1 | 6/2009 |
| WO | 2010133318 A1 | 11/2010 |

OTHER PUBLICATIONS

Golub et al. Science (1999), vol. 286 531-537.*
Lala et al. Cancer and Metastasis Reviews (1998), 17(1), 91-106.*
Chiji Yamazaki et al., Cyclization of isothiosemicarbazones. Part 10. A novel to route to 2-amino[1,2,4]triazolo[1.5-α] pyridine derivatives, J. Chem, Sou Perkin Trans., 1994; pp. 1972-1999.
International Search Report (Form PCT/ISA/210), Issued in the Corresponding Application No. PCT/EP2007/059051, Completed on Nov. 23, 2007 and Mailed on Dec. 3, 2007.
Ali Khaled et al Essential Role for the p110δ phosphoinositide 3-kinase in the allergeic response, Letters to Nature, 2004, pp. 1007-1011, vol. 431.
Andreas G. Bader et al., Oncogenic PI3K Deregulates Transcription and Translation, Nature Reviews Cancer, 2005, pp. 921-929, vol. 5.
Domingo F. Barber et al., PI3Kγ inhibition blocks glomerulonephritis and extends lifespan in a mouse model of systemic lupus, Nature Medicine, 2005, pp. 933-935, vol. 11, No. 9.
Leslie J. Berg et al., TEC Family Kinase in T Lymphocyte Development and Function, Annu. Rev. Immunol., 2005, pp. 549-600, vol. 23.
Lei Bi et al., Proliferative Defect and Embryonic Lethality in Mice Homozygous for a Deletion in the p110α Subunit of Phosphoinositide 3-Kinase, The Journal of Biological Chemistry, 1999, pp. 10963-10968, vol. 274, No. 16.

(Continued)

*Primary Examiner* — Samantha Shterengarts
(74) *Attorney, Agent, or Firm* — Loretta J. Sauermelch; Alan X. Scrivner

(57) ABSTRACT

The invention relates to compounds of formula (I); wherein X and $R^1$ to $R^5$ have the meaning as cited in the description and the claims. Said compounds are useful as protein kinase inhibitors, especially inhibitors of Itk or PI3K, for the treatment or prophylaxis of immunological, inflammatory or allergic disorders. The invention also relates to pharmaceutical compositions including said compounds, the preparation of such compounds as well as the production of and use as medicaments.

(I)

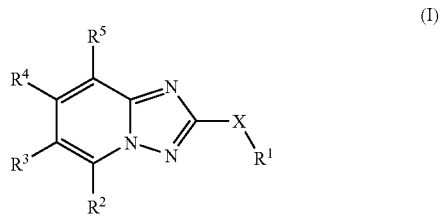

27 Claims, No Drawings

(56) References Cited

OTHER PUBLICATIONS

Tzvetanka Bondeva et al. Bifurcation of Lipid and Protein Kinase Signals of PI3Kγ to the Protein Kinases PKB and MAPK, Science, 1998, pp. 293-296, vol. 282.

Saskia M. Brachmann et al., Phosphoinostitide 3-Kinase Catalytic Subunit Deletion and Regulatory Subunit Deletion Have Opposite Effects on Insulin Sensitivity in MIce, Molecular and Cellular Biology, 2005. pp. 1596-1607, vol. 25, No. 5.

Monsterrat Camps et al., Blockade of PI3Kγ suppresses joint inflammation and damage in mouse models of rheumatoid arthritis, Nature Medicine, 2005, pp. 936-943, vol. 11, No. 9.

Lewis C. Cantley, The Phosphoinostitide 3-Kinase Pathway, Science, 2002, pp. 1655-1657, vol. 296.

Alison M. Condliffe et al., Sequential activation of class IB and class IA PI3K is important for the primed respiratory burst of human but not murine neutrophils, Blood, 2005, pp. 1432-1440, vol. 106, No. 4.

M. Falasca et al., Role of class II phosphoinositide 3-kinase in cell signalling, Biochemical Society Transitions, 2007, pp. 211-214.

G. John Ferguson et al., PI(3)Kγ has an important context-dependent role in neutrophil chemokinesis, Nature Cell Biology, 2007, pp. 86-91, vol. 9, No. 1.

Johan Forssell et al., Interleukin-2-Inducible T Cell Kinase Regulates Mast Cell Degranulation and Acute Allergic Responses, Am. J. Respir. Cell Mol. Biol., 2005, pp. 511-520, vol. 32.

Deborah C. Fowell et al., Impaired NFATc Translocation and Failure of Th2 Development in Itk-Deficient CD4+ T Cells, Immunity, 1999, pp. 399-409, vol. 11.

David A. Fruman et al., Phosphoinostitide Kinases, Annu. Rev. Biochem., 1998, pp. 481-507, vol. 67.

Daisuke Hata et al., Bruton's Tyrosine Kinase-mediated Interleukin-2 Gene Activation in Mast Cells, The Journal of Biological Chemistry, 1998, pp. 10979-10987, vol. 273, No. 18.

P.T. Hawkins et al., Signalling through Class I PI3Ks in mammalian cells, Biochemical Society Transactions, 2006, pp. 647-662, vol. 34.

Emilio Hirsch et al., Central Role for G Protein-Coupled Phosphoinositide 3-Kinase γ in Inflammation, Science, 2000, pp. 1049-1053.

Emilio Hirsch et al., Signaling through PI3KSCIENCE: a common platform for leukocyte, platelet and cardiovascular stress sensing, Thromb Haemost, 2006, pp. 29-35, vol. 95.

Zachary A. Knight et al., A Pharmacological Map of the PI3-K Family Defines a Role for p110α in Insulin Signalling, Cell 125, 2006, pp. 733-747, vol. 4.

Muriel Laffargue et al., Phosphoinositide 3-Kinase γ Is an Essential Amplifier of Mast Cell Function, Immunity, 2002, pp. 441-451, vol. 16.

Daniela Leopoldt et al., Gβγ Stimulates Phosphoinositide 3-Kinase-γ by Direct Interaction with Two Domains of the Catalytic p110 Subunit, The Journal of Biological Chemistry, 1998, pp. 7024-7029, vol. 273, No. 12.

Zhong Li et al., Roles of PLC-β2 and -β3 and PI3Kγ in Chemoattractant-Mediated Signal Transduction, Science, 2000, pp. 1046-1049, vol. 287.

Tai-An Lin et al., Selective Itk Inhibitors Block T-Cell Activation and Murine Lung Inflammation, Biochemistry, 2004, pp. 11056-11062, vol. 43.

Karine Lindmo et al., Regulation of membrane traffic by phosphoinositide 3-kinases, Journal of Cell Science, 2006, pp. 605-614, vol. 119.

Karen-Qianye Liu et al., T Cell Receptor-initiated Calcium Release Is Uncoupled from Capacitative Calcium Entry in Itk-deficient T Cells, J. Exp. Med., 1998, pp. 1721-1727, vol. 187, No. 10.

Marco Lopez-Llasaca et al., Linkage of G Protein-Coupled Receptors to the MAPK Signalling Pathway Through PI 3-Kinase γ, Science, 1997, pp. 394-397, vol. 275.

Yoshiko Matsumoto et al., Identification of Highly Expressed Genes in Peripheral Blood T Cells from Patients with Atopic Dermatitis, International Archives of Allergy and Immunology, 2002, pp. 327-340, vol. 129.

Cynthia Mueller et al., Attenuation of Immunological Symptoms of Allergic Asthma in Mice Lacking the Tyrosine Kinase ITK1, The Journal of Immunologies, 2003, pp. 5056-5063, vol. 170.

Klaus Okkenhaug et al., Impaired and T Cell Antigen Receptor Signaling in p110δ PI 3-Kinase Mutant Mice, Science, 2002, pp. 1031-1034, vol. 297.

Enrico Patrucco et al., PI3Kγ Modulates the Cardiac Response to Chronic Pressure Overload by Distinct Kinase-Dependent and -Indeoendent Effects, Cell, 2004, pp. 375-387, vol. 118.

Vinecnt Pomel et al., Furan-2-ylmethylene Thiazolidinediones as Novel, Potent, and Selective Inhibitors of Phosphoinositide 3-Kinase, Journal of Medicinal Chemistry, 2006, pp. 3857-3871, vol. 49, No. 13.

Christian Rommel et al., PI3Kδ and PI3Kγ: partners in crime in inflammation in rheumatoid arthritis and beyond?, Nature Reviews Immunology, 2007, pp. 191-201, vol. 7.

Ignacio Rubio et al., Interaction of Ras with phosphoinositide 3-kinase γ, Biochem. J., 1997, pp. 891-895, vol. 326.

Thomas Rückle et al., PI3Kγ inhibition: towards an 'aspirin of the 21st century'?, Nature Reviews Drug Discovery, 2006, pp. 903-918, vol. 5.

Chanchal Sadhu et al., Selective Role of PI3Kδ in neutrophil inflammatory responses, Biochemical and Biophysical Research Communications 308, 2003, pp. 764-769.

Takehiko Sasaki et al., Function of PI3Kγ in Thymocyte Development, T Cell Activation, and Neutrophil Migration, Science, 2000, pp. 1040-1046, vol. 287.

Edward M. Schaeffer et al., Requirement for Tec Kinases Rlk and Itk in T Cell Receptor Signaling and Immunity, 1999, Science, pp. 638-641, vol. 284.

Pamela L. Schwartzberg et al., TEC-Family Kinases: Regulators of T-Helper-Cell Differentiation, Nature Reviews Immunology. 2005, pp. 284-295, vol. 5.

C.I. Edvard Smith et al., The Tec family of cytoplasmic tyrosine kinases: mammalian Btk, Bmx, Itk, Tec, Txk and homologs in other species, BioEssays 23.5, 2001, pp. 436-446.

L. Stephens et al., A Novel Phosphoinositide 3 Kinase Activity in Myeloid-Derived Cells Is Activated by G Protein βγ Subunits, Cell, 1994, pp. 83-93, vol. 77.

Len Stephens et al., Protein Kinase B Kinases That Mediate Phosphatidylinositol 3, 4, 5-Trisphosphate-Dependent Activation of Protein Kinase B, Science, 1998, pp. 710-714, vol. 279.

L.R. Stephens et al., The Gβγ Sensitivity of a PI3K Is Dependent upon a Tightly Associated Adaptor, Cell, 1997, pp. 105-114, vol. 89.

Matthew J. Thomas et al., Airway inflammation: chemokine-induced neutrophilia and the class I phosphoinositide 3-kinases, Eur. J. Immunol., 2005, pp. 1283-1291, vol. 35.

Bart Vanhaesebroeck et al., Synthesis and Function of 3-Phosphorylated Inositol Lipids, Annu. Rev. Biochem., 2001, pp. 535-602, vol. 70.

Philipp Voigt et al., Characterization of p87PIKAP, a Novel Regulatory Subunit of Phosphoinositide 3-Kinase γ That Is Highly Expressed in Heart and Interacts with PDE3B, The Journal of Biological Chemistry, 2006, pp. 9977-9986, vol. 281, No. 15.

WS Fred Wong, Inhibitors of the tyrosine kinase signaling cascade for asthma, Current Opinion in Pharmacology, 2005, pp. 1-8, vol. 5.

Matthias P. Wymann et al., Phosphoinositide 3-kinase signalling-which way to target?, Trends in Pharmalogical Sciences, 2003, pp. 366-376, vol. 24, No. 7.

Matthias P. Wymann et al., Phosphoinositide 3-kinase in disease:timing, location, and scaffolding, Current Opinion in Cell Biology, 2005, pp. 141-149, vol. 17.

Matthias P. Wymann et a., Synthetic access to 2-amido-5-aryl-8-methoxy-triazolopyridine and 2-amido-5- morpholino-8-methoxy-triazolopyridine derivatives as potential inhibitors of the adenosine receptor subtypes, Synthesis, 2003, pp. 1649-1652.

Asakura et al., *World J. Gastroenterol.* 13(15):2145-2149 (2007).

Benistant et al., *Oncogene* 19(44):5083-5090 (2000).

Bille et al., *J. Infect. Dis.* 146:220-226 (1982).

Billottet et al., *Oncogene* 25(50):6648-6659 (2006).

Bruno et al., *J. Immunol.* 174:8090-8096 (2005).

Busse and Lemanske, *N. Engl. J. Med.* 344(5):350-362 (2001).

Carpenter et al., *J. Biol. Chem.* 265:19704-19711 (1990).

(56) References Cited

OTHER PUBLICATIONS

Carroll et al., *American Family Physician* 75(10):1513-1520 (2007).
Cauwels et al., *J. Clin. Invest.* 116(8):2244-2251 (2006).
Chang et al., *PNAS* 104(19):8077-8082 (2007).
Cohen et al., *Orphanet J. Rare Dis.* 2:34 (2007).
Crow et al., *Circ. Res.* 95(10):957-970 (2004).
D'Cruz et al., *Lancet* 369:587-596 (2007).
Doukas et al., *PNAS* 103(52):19866-19871 (2006).
Doukas et al., *Biochem. Soc. Trans.* 35(2):204-206 (2007).
Erhardt et al., *J. Virol.* 81(7):3058-67 (2007).
Firestein, *Nature* 423:356-361 (2003).
Foukas et al., *Nature*, 441:366-370 (2006).
Frangogiannis et al., *Cardiovasc. Res.* 53(1):31-47 (2002).
Fuchikami et al., *J. Biomol. Screening* 7(5):441-450 (2002).
Hale et al., *PNAS* 103(38):14194-14199 (2006).
Hanahan et al., *Cell* 100:57-70 (2000).
Hemmer et al., *Nat. Rev. Neuroscience* 3:291-301 (2002).
Hennessy et al., *Nat. Rev. Drug Discovery* 4(12):988-1004 (2005).
Jackson, et al., *Nature Medicine* 11(5):507-514 (2005).
Kang et al., *PNAS* 103(5):1289-1294 (2006).
Knobbe et al., *Brain Pathol.* 13(4):507-518 (2003).
Kratz et al., *Blood* 99(1):372-374 (2002).
Lupia et al., *Am. J. Pathol.* 165(6):2003-2011 (2004).
Mcintosh et al., *FASEB J* 6:2775-2782 (1992).
Molad Yet al., *J. Investig. Med.* 52(1):58-61 (2004).
Nashed et al., *Eur. J. Immunol.* 37:416-424 (2007).
Niswender et al., *Diabetes* 52:227-231 (2003).
Palanki et al., *J. Med. Chern.* 50(18):4279-4294 (2007).
Plum et al., *Trends Endocrinol. Metab.* 16(2):59-65 (2005).
Ryckman et al., *Arthritis & Rheumatism* 48(8):2310-2320 (2003).
Samuels et al., *Science* 304:554 (2004).
Samuels et al., *Cancer Cell* 7(6):561-573 (2005).
Schön et al., *New Engl. J. Med.* 352:1899-1912 (2005).
Seki et al., *DNA Research* 4:355-358 (1997).
Shapiro, *N. Engl. J. Med.* 352:2016-2019 (2005).
Stoyanow et al., *Science* 269:690-693 (1995).
Suzuki et al., *Chem Commun.* 866-867 (1979).
Vanhaesebroeck et al., *Proc. Natl. Acad Sci.* 94:4330-4335 (1997).
Vanhaesebroeck et al., *Trends in Biochemical Sciences* 30(4):194-204 (2005).
Walker et al., *Drug Discovery Today: Disease Mechanisms* 3(1):63-69 (2006).
Xu et al., *J. Clin. Inv.* 115(4):951-8 (2005).
International Search Report for PCT/EP2008/066001, mailed Jan. 29, 2009.
International Preliminary Report on Patentability for PCT/EP2008/066001, mailed Jun. 1, 2010.
Written Opinion of the International Searching Authority for PCT/EP2008/066001, Jun. 1, 2010.
Anieto and Gruenberg, "Chapter 4.3 Subcellular Fractionation of Tissue Culture Cells," in Current Protocols in Protein Science, Editors: John. E. Coligan, Ben M. Dunn, Hidde L. Ploegh, David W. Speicher, Paul T. Wingfield; John Wiley & Sons, Inc., ISBN: 0-471-14098-8 (2003).
Ausubel et al., "Chapter 11 Immunology," pp. 11-1 to 11-29 in: Short Protocols in Molecular Biology. Fifth Edition, John Wiley & Sons, Inc., New York, (2002).
Bain et al., "The Selectivity of Protein Kinase Inhibitors: A Further Update," Biochem. J. 408:297-315 (2007).
Balla and Balla, "Phosphatidylinositol 4-Kinases: Old Enzymes with Emerging Functions," Trends in Cell Biology 16:351-361 (2006).
Bantscheff et al., "Quantitative Chemical Proteomics Reveals Mechanisms of Action of Clinical ABL Kinase Inhibitors," Nat Biotechnol. 25:1035-1044 (2007).
Biddison, W.E., "Chapter 2.2 Preparation and Culture of Human Lymphocytes," pp. 2.2.1-2.213 in Current Protocols in Cell Biology, John Wiley & Sons, Inc. (1998).
Breinbauer et al., "Natural Product Guided Compound Library Development," Curr Med Chem. 9:2129-2145 (2002).

Castle, "Chapter 4.2: Purification of Organelles from Mammalian Cells" pp. 4.2.1-4.2.57 in Current Protocols in Protein Science John Wiley & Sons, Inc., (2004).
Deora et al., "A Redox-Triggered Ras-Effector Interaction. Recruitment of Phosphatidylinositol 3'-Kinase to Ras by Redox Stress," J Biol Chem. 273:29923-29928 (1998).
Elias and Gygi, "Target-Decoy Search Strategy for Increased Confidence in Large-Scaled Protein Identifications by Mass Spectrometry," Nat. Methods 4:207-214 (2007).
Fenteany et al., "Inhibition of Proteasome Activities and Subunit-Specific Amino-Terminal Threonine Modification by Lactacystin," Science 268:726-731 (1995).
Garcia-Martinez et al., "Ku-0063794 is a Specific Inhibitor of the Mammalian Target of Rapamycin (mTOR)," Biochem. J. 421:29-42 (2009).
Gharbi et al., "Exploring the Specificity of the PI3K Family Inhibitor L Y294002," Biochem J. 404:15-21 (2007).
Glickman et al., "A Comparison of ALPHAScreen, TR-FRET, and TRF as Assay Methods for FXR Nuclear Receptors," J. Biomol Screen 7:3-10 (2002).
Karaman et al., "A Quantitative Analysis of Kinase Inhibitor Selectivity," Nat Biotechnol. 26:127-32 (2008).
Karwa and Mitra, Techniques for the Extraction, Isolation, and Purification of Nucleic Acids; Chapter 8 in "Sample Preparation Techniques in Analytical Chemistry," Chemical Analysis 162:331-375 (2003).
Kashem et al., "Three Mechanistically Distinct Kinase Assays Compared: Measurement of Intrinsic ATPase Activity Identified the Most Comprehensive Set of ITK Inhibitors," J. Biomol. Screening 12:70-83 (2007).
Kersey et al., "Technical Brief: The International Protein Index: An Integrated Database for Proteomics Experiments," Proteomics 4:1985-1988 (2004).
Lingaraj et al., "A High-Throughput Liposome Substrate Assay with Automated Lipid Extraction Process for PI3-Kinase," J. Biolmol. Screen. 13:906-911 (2008).
Mann et al., "Analysis of Proteins and Proteomes by Mass Spectrometry," Ann. Rev. Biochem. 70:437-473 (2001).
Moger et al., "The Application of Fluorescence Lifetime Readouts in High-Throughput Screening," J. Biomol. Screening 11:765-772 (2006).
Patricelli et al., "Functional Interrogation of the Kinome Using Nucleotide Acyl Phosphates," Biochemistry. 46:350-358 (2007).
Perkins et al., "Probability-Based Protein Identification by Searching Sequence Databases Using Mass Spectrometry Data," Electrophoresis 20:3551-3567 (1999).
Petty, "Overview of the Physical State of Proteins Chapter 1", Unit 5.1.1-5.1.10 in Current Protocols in Cell Biology John Wiley & Sons, Inc. (1998).
Ross et al., "Multiplexed Protein Quantitation in *Saccharomyces cerevisae* Using Amine-Reactive Isobaric Tagging Reagents," Mol. Cell. Proteomics 3:1154-1169 (2004).
Sasaki et al., "Colorectal carcinomas in mice lacking the catalytic subunit of PI(3)Kgamma," Nature 406:897-902 (2000).
Shevchenko et al., "Mass spectrometric sequencing of proteins silver-stained polyacrylamide gels," Anal Chem. 68:850-858 (1996).
Subramanian, "Immunoaffinity Chromatography," Molecular Biotechnology 20:41-47 (2002).
Tolias et al., "Type I Phosphatidylinositoi-4-Phosphate 5-Kinases Synthesize the Novel Lipids Phosphatidylinositol 3, 5-Bisphosphate and Phosphatidylinositol 5-Phosphate," J. Biol. Chem. 273:18040-18046 (1998).
Vedvik et al., "Overcoming Compound Interference in Fluorescence Polarization-Based Kinase Assays Using Far-Red Tracers," Assay Drug Dev. Technol. 2:193-203 (2004).
Weernink et al., "Regulation and Cellular Roles of Phosphoinositide 5-Kinases," Eur. J. Pharmacal. 500:87-99 (2004).
Wingfield, Paul T., "Production of Recombinant Proteins," Chapter 5, Unit 5.0.1-5.0.3 in: Current Protocols in Protein Science, Editors: John. E. Coligan, Ben M. Dunn, Hidde L. Ploegh, David W. Speicher, Paul T. Wingfield; John Wiley & Sons Inc., ISBN: 0-471-14098-8 (2002).

(56) References Cited

OTHER PUBLICATIONS

Wu et al., "Comparative Study of Three Proteomic Quantitative Methods, DIGE, ciCAT, and iTRAQ, Using 2D Gel- or LC-MALDI TOF/TOF," J. Proteome Res. 5:651-658 (2006).

Wymann and Schneiter, "Lipid Signalling in Disease," Nat. Rev. Mol. Cell. Bio. 9:162-176 (2008).

Zaman et al., "Fluorescence Assays for High-Throughput Screening of Protein Kinases," Comb. Chem. High Throughput Screen 6: 313-320 (2003).

Zaman et al., "Enzyme Fragment Complementation Binding Assay for P38α Mitogen-Activated Protein Kinase to Study the Binding Kinetics of Enzyme Inhibitors," Assay Drug Dev. Technol. 4:411-420 (2006).

Zhang et al., "Time-Resolved Forster Resonance Energy Transfer Assays for the Binding of Nucleotide and Protein Substrates to P38a Protein Kinase," Analytical Biochemistry 343:76-83 (2005).

International Preliminary Report on Patentability for International Application No. PCT/EP2010/002987, issued Nov. 22, 2011.

International Search Report for International Application No. PCT/EP2010/002987, completed Aug. 13, 2010, mailed Aug. 20, 2010.

Office Action in U.S. Appl. No. 12/744,940 dated Sep. 21, 2012.

* cited by examiner

TRIAZOLE DERIVATIVES AS KINASE INHIBITORS

This is a National Phase Application in the United States of International Patent Application No. PCT/EP2007/059051 filed Aug. 30, 2007, which claims priority on European Patent Application No. 06119831.3 filed Aug. 30, 2006, which claims priority on European Patent Application No. 07108769.6 filed May 23, 2007. The entire disclosures of the above patent applications are hereby incorporated by reference.

The present invention relates to a novel class of kinase inhibitors, including pharmaceutically acceptable salts, prodrugs and metabolites thereof, which are useful for modulating protein kinase activity for modulating cellular activities such as signal transduction, proliferation, differentiation, programmed cell death, migration and cytokine secretion. More specifically the invention provides compounds which inhibit, regulate and/or modulate kinase activity, in particular Itk or PI3K activity, and signal transduction pathways relating to cellular activities as mentioned above. Furthermore, the present invention relates to pharmaceutical compositions comprising said compounds, e.g. for the treatment of diseases such as immunological, inflammatory and allergic disorders, and processes for preparing said compounds.

Protein kinases participate in the signaling events which control the activation, growth, differentiation and survival of cells in response to extracellular mediators or stimuli such as growth factors, cytokines or chemokines. In general, these kinases are classified in two groups, those that preferentially phosphorylate tyrosine residues and those that preferentially phosphorylate serine and/or threonine residues. The tyrosine kinases include membrane-spanning growth factor receptors such as the epidermal growth factor receptor (EGFR) and cytosolic non-receptor kinases such as Src family kinases (Lck and Lyn), the Syk family kinases (ZAP-70 and Syk) and the Tec family kinases (e.g. Itk).

Inappropriately high protein kinase activity is involved in many diseases including cancer, metabolic diseases, immunological diseases and inflammatory disorders. This can be caused either directly or indirectly by the failure of control mechanisms due to mutation, overexpression or inappropriate activation of the enzyme. In all of these instances, selective inhibition of the kinase is expected to have a beneficial effect.

Protein tyrosine kinases—both receptor tyrosine kinases and non-receptor kinases—are essential for the activation and proliferation of cells of the immune system. Among the earliest detectable events upon the immunoreceptor activation in mast cells, T cells and B cells is the stimulation of non-receptor tyrosine kinases. Immune receptors such as the high-affinity IgE receptor (FcεRI), T cell antigen receptor (TCR) and B cell receptor (BCR), consist of antigen-binding subunits and signal transducing subunits. The signal transducing chain contains one or more copies of immunoreceptor tyrosine-based activation motifs (ITAMSs). For TCR activation, ITAMS located in the CD3 molecule are phosphorylated by Lck and Fyn, two Src family tyrosine kinases, followed by recruitment and activation of ZAP-70, a member of the Syk family of tyrosine kinases. These activated tyrosine kinases then phosphorylate downstream adaptor molecules such as LAT (linker for activation of T cells) and SLP-76 (SH2 domain-containing leukocyte protein of 76 kDa). This step leads to the activation of multiple downstream signaling molecules such as inducible T cell kinase (Itk), PLCγ1 and PI3 kinase (PI3K) (Wong, 2005, Current Opinion in Pharmacology 5, 1-8).

The Tec family now comprises five members (Tec, Btk, Itk, Rlk and Bmx) which are expressed mainly by hematopoietic cells and play a central role in signaling through immune receptors such as the high-affinity IgE receptor (FcεRI), T cell antigen receptor (TCR) and B cell receptor (BCR) (Smith et al., 2001, Bioessays 23, 436-446). The members of the Tec family share a common protein domain organization. They have an amino-terminal Pleckstrin Homology domain, a Tec homology domain with one or two proline-rich regions, Src homology 3 (SH3) and 2 (SH2) protein interaction domains and a carboxy-terminal kinase domain. Activation of the Tec family kinases requires several steps: recruitment to the plasma membrane through their Pleckstrin Homology domain, phosphorylation by Src family kinases and interactions with proteins that bring them into the vicinity of immune receptor signaling complexes (Schwartzberg et al., 2005, Nature Reviews Immunology 5, 284-295).

Tec family kinases are essential for B cell development and activation. Patients with mutated Btk display a block in B cell development resulting in the almost complete absence of B cells and plasma cells, reduced Ig levels and an impaired humoral immune response (Smith et al., 2001, Bioessays 23, 436-446).

In addition, Tec kinases play a role in mast cell activation through the high-affinity IgE receptor (FcεRI). Itk and Btk are expressed in mast cells and are activated by FcεRI crosslinking (Hata et al., 1998, J. Biol. Chem. 273, 19979-10987). Both acute and late phase inflammatory allergic responses are significantly reduced in Itk-deficient mice when challenged with allergen via the airways. Importantly, airway mast cell degranulation is impaired despite wild-type levels of allergen-specific IgE and IgG1 (Forssell et al., 2005, Am. J. Respir. Cell Mol. Bio. 32, 511-520).

T cells express three Tec kinases (Itk, Rlk and Tec) which are involved in T cell receptor (TCR) signaling (Berg et al., 2005, Ann. Rev. Immunol. 23, 549-600). The study of genetically manipulated mice in which the gene encoding the Itk protein is deleted gives important information about the physiological and pathophysiological function of Itk. Itk-deficient (Itk$^{-/-}$) mice display a calcium mobilization defect after TCR stimulation (Liu et al, 1998, J. Exp. Med. 187, 1721-1727). In addition, Itk$^{-/-}$ mice have specific defects in T Helper 2 ($T_H2$) cell development (Fowell et al., 1999, Immunity 11, 399-409; Schaeffer et al., 1999, Science 284, 638-641). $T_H2$-cell responses play a role in the pathology of allergic asthma characterized by an increased number of $T_H2$ cells in the lungs, increased $T_H2$ cytokine secretion and mucus production. In a mouse model of allergic asthma, Itk-deficient mice show decreased interleukin 5 (IL-5) and interleukin 13 (IL-13) secretion, less mucus production and reduced T cell infiltration in the lungs (Mueller and August, 2003, J. Immunol. 170, 5056-5063). This study suggests that Itk is important for the pathology of allergic asthma and suggests that Itk is a potential therapeutic target for asthma. This notion is further corroborated by studies with compounds that selectively inhibit Itk kinase activity (Lin et al., 2004, Biochemistry 43, 11056-11062).

By contrast, Itk expression is elevated in T cells from patients with Atopic Dermatitis, a $T_H2$ cell mediated disease (Matsumoto et al., 2002, Int. Archiv. Allergy Immunol 129, 327-340). Taken together, these reports suggest that Itk is a suitable therapeutic target for immunological, inflammatory and allergic disorders provided that inhibitors with sufficient potency and selectivity can be identified.

Phosphoinositide 3-kinase (also called Phosphatidylinositol 3-kinase, PI3K) represents a group of dual-specificity kinases that play pivotal roles as lipid and protein kinases in numerous intracellular signaling events, for example in T-cell receptor signaling (Cantley L C, 2002, Science 296(5573):1655-7; Vanhaesebroeck B et al., 2001, Annu Rev. Biochem. 70:535-602; Bondeva T et al., 1998, Science 282(5387):293-6).

PI3K belongs to a superfamily of signaling lipid kinases that catalyse the phosphorylation of phosphatidylinositol-4,5-bisphosphate (PtdIns(4,5)P2 or phosphatidylinositol (PtdIns) at the 3'-OH group, giving rise to the second messengers phosphatidylinositol-3,4,5-trisphosphate (PtdIns(3,4,5)P3) or phosphatidylinositol-3-phosphate (PtdIns(3)P). PtdIns(3,4,5)P3 can be converted into PtdIns(3,4)P2 by SH2-containing inositol phosphatase (SHIP), or can be dephosphorylated by phosphatase and tensin homologue (PTEN) phosphatase to regenerate PtdIns(4,5)P2. The 3'-phosphorylated phosphoinositides, PtdIns(3,4,5)P3, PtdIns(3,4)P2 and PtdIns(3)P, recruit and activate various signalling proteins (PtdInsbinding proteins; PtdIns-BPs) through direct lipid-protein interactions (Fruman D A et al., 1998, Annu Rev. Biochem. 67:481-507; Hawkins P T et al., 2006, Biochem. Soc. Trans. 34:647-62).

Phosphatidylinositol-3,4,5-trisphosphate (PtdIns(3,4,5)P3) has an important role as second messenger by working as a docking platform for lipid-binding domains, such as the pleckstrin homology (PH) domains of various cellular proteins. These include kinases (such as 3-phosphoinositide-dependent protein kinase 1 (PDK1) and protein kinase B (PKB)/Akt) that trigger downstream kinase cascades, and guanine-nucleotide exchange factors (such as Vav and P-Rex) that control the activity of small GTPases (Wymann M P et al., 2005, Curr Opin Cell Biol. 17(2):141-9; Wymann M P et al., 2003, Trends Pharmacol. Sci. 24(7):366-76; Stephens L et al., 1998, Science 279(5351):710-4).

PI3-kinase activation is believed to be involved a variety of signal transduction pathways, including those essential to cell proliferation, cell differentiation, cell growth, cell survival, apoptosis, adhesion, chemotaxis, invasion, cytoskeletal rearrangement, cell shape changes, vesicle trafficking and metabolic pathways. PI3K appears to be involved in a number of aspects of leukocyte activation (Rommel C et al., 2007, Nat. Rev. Immunol. 7(3):191-201; Ruckle T et al., 2006, Nat. Rev. Drug Discov. 5(11):903-18).

Different types of PI3K have been identified and grouped into three classes according to their primary and secondary structures, mode of regulation and substrate specificity. Class I PI3K has been the most extensively studied so far, and includes heterodimeric proteins that consist of a catalytic and a regulatory adaptor subunit, the nature of which determines a further subdivision into class IA and IB PI3K. Class II PI3K uses PtdIns as in vivo substrate, yielding phosphatidylinositol-3-phosphate (PtdIns(3)P). Some evidence has been presented that class II enzymes, similarly to class I can be activated by external stimuli. By contrast, the class III PI3K, represented by a single species (hVps34) in humans, has relatively high activity even in resting cells. The class III represents the most ancient form of PI3K and as class II, uses PtdIns as a substrate to produce PtdIns(3)P (Falasca M et al., 2007, Biochem. Soc. Trans. 35:211-4; Lindmo K et al., 2006, J. Cell Sci. 119:605-14).

The class IA-PI3Kα, β and δ (PIK3CA, PIK3CB and PIK3CD)—consists of an SH2-domain-containing regulatory subunit (p85; five distinct isoforms of which have been identified) that forms a complex with one of three catalytic subunits, p110α, p110β or p110δ (Bader A G et al., 2005, Nat. Rev. Cancer 5(12):921-9; Bi L et al., 1999, J. Biol. Chem. 274(16):10963-8; Brachmann S M et al., 2005, Mol. Cell. Biol. 25(5):1596-607).

Genetic polymorphisms within the PI3K pathway are also associated with an increased risk of type 2 diabetes. Downstream of the insulin-like growth factor 1 (IGF1) receptor, signaling through class I PI3K controls growth and development. Moreover, amplification and point mutations of the gene encoding PI3Kα that increase the enzymatic activity of the protein have been frequently found in human cancers. PI3Kβ has been implicated in regulating the formation and stability of integrin α(IIb)β(3), which is necessary for the activation and aggregation of platelets. PI3Kδ is predominantly expressed in the haematopoietic system and PI3Kδ-deficient mice are viable, fertile, apparently healthy and have a normal life span. PI3Kδ has important roles in T- and B-cell signaling, mast-cell-mediated allergic responses, the neutrophils oxidative burst and, possibly, extravasation (Ali K et al., 2004, Nature 431(7011):1007-11; Okkenhaug K et al., 2002, Science 297(5583):1031-4). PI3K inhibitors selective for PI3Kδ were reported to block neutrophil activation in an animal model for neutrophil activation, thus pointing to PI3kδ as a target for the development of anti-inflammatory drugs (Sadhu et al., 2003, Biochem. Biophys. Res. Communications 308, 764-769).

PI3Kγ, the only member of class IB (PIK3CG), associates with two regulatory subunits, p101 and p84, that control its expression, activation and subcellular location. PI3Kγ activation is driven by the activation of pertussis-toxin-sensitive Gαi-coupled G-protein-coupled receptors (GPCRs), and is mediated by direct association of its catalytic domain with the βγ subunits of G proteins and Ras (Stephens L et al., 1994, Cell 77(1):83-93; Leopoldt D et al., 1998, Biol. Chem. 273 (12):7024-9).

Several proteins, such as Ras, mitogen-activated protein kinase (MAPK) kinase (MEK), phosphodiesterase (PDE), p101 and p84, can bind to PI3Kγ, indicating a protein-scaffold function in addition to its enzymatic activity. PI3Kγ was also shown to directly phosphorylate and activate MEK as well as to mediate G βγ-dependent regulation of JNK activity (Lopez-Ilasaca M et al., 1997, Science 275(5298):394-7; Rubio I et al., 1997, Biochem J. 326:891-5; Stephens L R et al., 1997, Cell 89(1):105-14; Voigt P et al., 2006, J Biol. Chem. 281(15):9977-86).

The mouse PI3Kγ protein is encoded by the Pik3cg locus. Mice lacking functional PI3Kγ (PI3 Kg−/− mice) were viable, fertile, and displayed a normal life span in a conventional mouse facility. Further studies revealed that neutrophils of these mice were unable to produce PtdIns (3,4,5) P3 when stimulated with GPCR agonists such as formylated bacterial peptides (N-formyl-Met-Leu-Phe, fMLP), complement C5a or interleukin 8 (IL-8). This observation demonstrates that PI3Kγ is the sole PI3K isoform that is coupled to these GPCRs in neutrophils (Hirsch E et al., 2000, Science 287(5455):1049-53; Sasaki T et al., 2000, Science 287(5455):1040-6; Li Z et al., 2000, Science 287(5455):1046-9).

Moreover, PtdIns (3, 4, 5) P3-dependent activation of protein kinase B (PKB) was also absent in those neutrophils, while PKB could still be activated by GM-CSF or IgG/C3b-coated zymosan. Pi3kcg−/− mice showed impaired thymocyte development and increases in neutophil, monocyte, and eosinophil populations. Furthermore, neutrophils and macrophages isolated from Pi3kcg−/− mice exhibited severe defects in migration and respiratory burst in response to GPCR agonists and chemotactic agents. Work with knockout mice also established that PI3Kγ is an essential amplifier of mast cell activation (Ferguson G J et al., 2007, Nat. Cell Biol. 9(1):86-91; Condliffe A M et al., 2005, Blood 106(4):1432-40; Patrucco E et al., 2004, Cell 118(3):375-87; Laffargue M et al., 2002, Immunity 16(3):441-51). Collectively, the class IB phosphoinositide 3-kinase PI3Kγ seems to be pivotal in the control of leukocyte trafficking and accordingly the development of isotype-selective inhibitors of PI3Kγ should be an attractive anti-inflammatory therapeutic strategy (Knight Z A et al., 2006, Cell 125(4):733-47; Thomas M J et al., 2005, Eur. J. Immunol. 35(4):1283-91; Camps M et al., 2005, Nat. Med. 11(9):936-43; Barber D F et al., 2005, Nat. Med. 11(9):933-5).

PI3Kγ plays a crucial role in both vascular cells and white blood cells. It controls diverse immune modulatory and vascular functions like respiratory burst, cell recruitment, mast cell reactivity, platelet aggregation, endothelial activation as well as smooth muscle contractility.

The relative specificity of these events suggests that blocking PI3Kγ function might turn out beneficial for diseases like inflammation, allergy, autoimmunity, thrombosis, and major cardiovascular disorders like hypertension and atherosclerosis (Hirsch E et al., 2006, Thromb. Haemost. 95(1):29-35).

Recently, the development of potent and selective PI3Kγ inhibitors was reported (Pomel et al., 2006, J. Med. Chem. 49(13):3857-71). Treatment with these compounds caused a reduction of leukocyte recruitment in a mouse model of acute peritonitis.

Thus, an object of the present invention is to provide a new class of compounds as kinase inhibitors, especially as Itk or PI3K inhibitors, which may be effective in the treatment or prophylaxis of immunological, inflammatory, allergic disorders or other diseases or disorders associated with both kinases, Itk and PI3K. Furthermore, another object of the present invention is to provide said compounds, which may be effective in the treatment or prophylaxis of cancer or cardiovascular disorders associated with PI3K only.

Accordingly, the present invention provides compounds of formula (I)

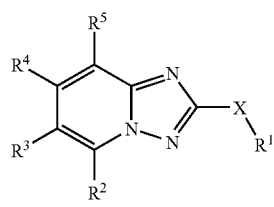

(I)

or a pharmaceutically acceptable salt, prodrug or metabolite thereof, wherein

X is O; S or $NR^6$;

$R^1$ is $T^1$; $C_{1-6}$ alkyl; $C(O)OR^7$; $C(O)R^7$; $C(O)N(R^7R^{7a})$; $S(O)_2N(R^7R^{7a})$; $S(O)N(R^7R^{7a})$; $S(O)_2R^7$; or $S(O)R^7$, wherein $C_{1-6}$ alkyl is optionally substituted with one or more $R^8$;

One of $R^2$, $R^3$ is $T^2$ and the other is $R^{5a}$;

$R^4$, $R^5$, $R^{5a}$ are independently selected from the group consisting of H; halogen; CN; $C(O)OR^9$; $OR^9$; $C(O)R^9$; $C(O)N(R^9R^{9a})$; $S(O)_2N(R^9R^{9a})$; $S(O)N(R^9R^{9a})$; $S(O)_2R^9$; $S(O)R^9$; $N(R^9)S(O)_2N(R^{9a}R^{9b})$; $SR^9$; $N(R^9R^{9a})$; $OC(O)R^9$; $N(R^9)C(O)R^{9a}$; $N(R^9)S(O)_2R^{9a}$; $N(R^9)S(O)R^{9a}$; $N(R^9)C(O)N(R^{9a}R^{9b})$; $N(R^9)C(O)OR^{9a}$; $OC(O)N(R^9R^{9a})$; and $C_{1-6}$ alkyl, wherein $C_{1-6}$ alkyl is optionally substituted with one or more halogen, which are the same or different;

$R^6$, $R^{7a}$, $R^9$, $R^{9a}$, $R^{9b}$ are independently selected from the group consisting of H; and $C_{1-6}$ alkyl, wherein $C_{1-6}$ alkyl is optionally substituted with one or more halogen, which are the same or different;

$R^7$ is $T^1$; or $C_{1-6}$ alkyl, wherein $C_{1-6}$ alkyl is optionally substituted with one or more $R^8$;

$R^8$ is $T^1$; $C_{1-6}$ alkyl; halogen; CN; $C(O)OR^{11}$; $OR^{11}$; $C(O)R^{11}$; $C(O)N(R^{11}R^{11a})$; $S(O)_2N(R^{11}R^{11a})$; $S(O)N(R^{11}R^{11a})$; $S(O)_2R^{11}$; $S(O)R^{11}$; $N(R^{11})S(O)_2N(R^{11a}R^{11b})$; $SR^{11}$; $N(R^{11}R^{11a})$; $OC(O)R^{11}$; $N(R^{11})C(O)R^{11a}$; $N(R^{11})S(O)_2R^{11a}$; $N(R^{11})S(O)R^{11a}$; $N(R^{11})C(O)N(R^{11a}R^{11b})$; $N(R^{11})C(O)OR^{11a}$; or $OC(O)N(R^{11}R^{11a})$, wherein $C_{1-6}$ alkyl is optionally substituted with one or more halogen which are the same or different;

$T^1$ is $C_{3-7}$ cycloalkyl; heterocyclyl; or phenyl, wherein $T^1$ is optionally substituted with one or more $R^{10}$;

$R^{11}$, $R^{11a}$, $R^{11b}$, are independently selected from the group consisting of H; and $C_{1-6}$ alkyl, wherein $C_{1-6}$ alkyl is optionally substituted with one or more halogen, which are the same or different;

$R^{10}$ is $C_{1-6}$ alkyl; halogen; CN; $C(O)OR^{12}$; $OR^{12}$; oxo (=O), where the ring is at least partially saturated; $C(O)R^{12}$; $C(O)N(R^{12}R^{12a})$; $S(O)_2N(R^{12}R^{12a})$; $S(O)N(R^{12}R^{12a})$; $S(O)_2R^{12}$; $S(O)R^{12}$; $N(R^{12})S(O)_2N(R^{12a}R^{12b})$; $SR^{12}$; $N(R^{12}R^{12a})$; $OC(O)R^{12}$; $N(R^{12})C(O)R^{12a}$; $N(R^{12})S(O)_2R^{12a}$; $N(R^{12})S(O)R^{12a}$; $N(R^{12})C(O)N(R^{12a}R^{12b})$; $N(R^{12})C(O)OR^{12a}$; or $OC(O)N(R^{12}R^{12a})$, wherein $C_{1-6}$ alkyl is optionally substituted with one or more halogen which are the same or different;

$R^{12}$; $R^{12a}$; $R^{12b}$ are independently selected from the group consisting of H; and $C_{1-6}$ alkyl, wherein $C_{1-6}$ alkyl is optionally substituted with one or more halogen, which are the same or different;

$T^2$ is $T^3$; $C(R^{13}R^{13a})$-$T^3$; $C(R^{13}R^{13a})$—$C(R^{13b}R^{13c})$-$T^3$; cis $C(R^{13})$=$C(R^{13b})$-$T^3$; trans $C(R^{13})$=$C(R^{13b})$-$T^3$; or C≡C-$T^3$;

$R^{13}$, $R^{13a}$, $R^{13b}$, $R^{13c}$ independently selected from the group consisting of H; and F;

$T^3$ is heterocyclyl; heterobicyclyl; phenyl; naphthyl; indenyl; or indanyl; wherein $T^3$ is optionally substituted with one or more $R^{14}$;

$R^{14}$ is $C_{1-6}$ alkyl; halogen; CN; $C(O)OR^{15}$; $OR^{15}$; oxo (=O), where the ring is at least partially saturated; $C(O)R^{15}$; $C(O)N(R^{15}R^{15a})$; $S(O)_2N(R^{15}R^{15a})$; $S(O)N(R^{15}R^{15a})$; $S(O)_2R^{15}$; $S(O)R^{15}$; $N(R^{15})S(O)_2N(R^{15a}R^{15b})$; $SR^{15}$; $N(R^{15}R^{15a})$; $OC(O)R^{15}$; $N(R^{15})C(O)R^{15a}$; $N(R^{15})S(O)_2R^{15a}$; $N(R^{15})S(O)R^{15a}$; $N(R^{15})C(O)N(R^{15a}R^{15b})$; $N(R^{15})C(O)OR^{15a}$; or $OC(O)N(R^{15}R^{15a})$, wherein $C_{1-6}$ alkyl is optionally substituted with one or more $R^{16}$;

$R^{15}$, $R^{15a}$, $R^{15b}$ are independently selected from the group consisting of H; and $C_{1-6}$ alkyl, wherein $C_{1-6}$ alkyl is optionally substituted with $R^{17}$;

$R^{16}$, $R^{17}$ are independently selected from the group consisting of halogen; CN; $C(O)OR^{18}$; $OR^{18}$; $C(O)R^{18}$; $C(O)N(R^{18}R^{18a})$; $S(O)_2N(R^{18}R^{18a})$; $S(O)N(R^{18}R^{18a})$; $S(O)_2R^{18}$; $S(O)R^{18}$; $N(R^{18})S(O)_2N(R^{18a}R^{18b})$; $SR^{18}$; $N(R^{18}R^{18a})$; $OC(O)R^{18}$; $N(R^{18})C(O)R^{18a}$; $N(R^{18})S(O)_2R^{18a}$; $N(R^{18})S(O)R^{18a}$; $N(R^{18})C(O)N(R^{18a}R^{18b})$; $N(R^{18})C(O)OR^{18a}$; $OC(O)N(R^{18}R^{18a})$; and $C_{1-6}$ alkyl, wherein $C_{1-6}$ alkyl is optionally substituted with one or more halogen, which are the same or different;

$R^{18}$, $R^{18a}$, $R^{18b}$ are independently selected from the group consisting of H; and $C_{1-6}$ alkyl, wherein $C_{1-6}$ alkyl is optionally substituted with one or more halogen, which are the same or different.

In case a variable or substituent can be selected from a group of different variants and such variable or substituent occurs more than once the respective variants can be the same or different.

Within the meaning of the present invention the terms are used as follows:

"Alkyl" means a straight-chain or branched carbon chain that may contain double or triple bonds. It is generally preferred that alkyl doesn't contain double or triple bonds. Thus, the term "alkyl" includes within the meaning of the present invention alkyl groups as well as alkenyl and alkinyl groups. Each hydrogen of an alkyl carbon may be replaced by a substituent.

"$C_{1-4}$ alkyl" means an alkyl chain having 1-4 carbon atoms, e.g. if present at the end of a molecule: methyl, ethyl, —CH=CH$_2$, —C≡CH, n-propyl, isopropyl, —CH=CH—CH$_3$, —CH$_2$—CH=CH$_2$, n-butyl, isobutyl, —CH=CH—CH$_2$—CH$_3$, —CH=CH—CH=CH$_2$, sec-butyl tert-butyl, or e.g. —CH$_2$—, —CH$_2$—CH$_2$—, —CH=CH—, —CH(CH$_3$)—, —C(CH$_2$)—, —CH$_2$—CH$_2$—CH$_2$—, —CH(C$_2$H$_5$)—, —CH(CH$_3$)$_2$—, when two moieties of a molecule are linked by the alkyl group. Preferably, $C_{1-4}$ alkyl includes methyl, ethyl, n-propyl, isopropyl, n-butyl, isobutyl, sec-butyl and tert-butyl. Each hydrogen of a $C_{1-4}$ alkyl carbon may be replaced by a substituent.

"$C_{1-6}$ alkyl" means an alkyl chain having 1-6 carbon atoms, e.g. if present at the end of a molecule: $C_{1-4}$ alkyl, methyl, ethyl, —CH=CH$_2$, —C≡CH, n-propyl, isopropyl, —CH=CH—CH$_3$, —CH$_2$—CH=CH$_2$, n-butyl, isobutyl, —CH=CH—CH$_2$—CH$_3$,—CH=CH—CH=CH$_2$, sec-butyl; tert-butyl, n-pentyl, n-hexyl, or e.g. —CH$_2$—, —CH$_2$—CH$_2$—, —CH=CH—, —CH(CH$_3$)—, —C(CH$_2$)—, —CH$_2$—CH$_2$—CH$_2$—, —CH(C$_2$H$_5$)—, —CH(CH$_3$)$_2$—, when two moieties of a molecule are linked by the alkyl group. Preferably, $C_{1-6}$ alkyl includes methyl, ethyl, n-propyl, isopropyl, n-butyl, isobutyl, sec-butyl and tert-butyl, n-pentyl, and n-hexyl. Each hydrogen of a $C_{1-6}$ alkyl carbon may be replaced by a substituent.

"$C_{3-7}$ cycloalkyl" or "$C_{3-7}$ cycloalkyl ring" means a cyclic alkyl chain having 3-7 carbon atoms, e.g. cyclopropyl, cyclobutyl, cyclopentyl, cyclohexyl, cyclohexenyl, cycloheptyl. Preferably, $C_{3-7}$ cycloalkyl includes cyclopropyl, cyclobutyl, cyclopentyl, cyclohexyl, and cycloheptyl. Each hydrogen of a cycloalkyl carbon may be replaced by a substituent.

"Halogen" means fluoro, chloro, bromo or iodo. It is generally preferred that halogen is fluoro or chloro.

"Heterocyclyl" or "heterocycle" means a cyclopentane, cyclohexane or cycloheptane ring, preferably a cyclopentane or cyclohexane ring, that may contain up to the maximum number of double bonds (aromatic or non-aromatic ring which is fully, partially or un-saturated) wherein at least one carbon atom up to 4 carbon atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for heterocycles are furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfo lane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, azepine and homopiperazine. "Heterocycle" means also azetidine. Accordingly, a heterocycle may have up to seven ring atoms.

"Aromatic heterocyclyl" or "aromatic heterocycle" means a cyclopentane, cyclohexane or cycloheptane ring, preferably a cyclopentane or cyclohexane ring that contains up to the maximum number of conjugated ring double bonds. Examples for aromatic heterocycles are furan, thiophene, pyrrole, imidazole, pyrazole, oxazole, isoxazole, thiazole, isothiazole, thiadiazole, pyranium, pyridine, pyridazine, pyrazine, pyrimidine, piperazine, triazole, and tetrazole.

"Non-aromatic heterocyclyl" or "non-aromatic heterocycle" means heterocyclyl or heterocycle other than an aromatic heterocyclyl or aromatic heterocycle, especially a fully saturated heterocyclyl or heterocycle.

"Heterobicyclyl" or "heterobicycle" means a heterocycle which is condensed with phenyl, $C_{3-7}$ cycloalkyl or an additional heterocycle to form a bicyclic ring system. "Condensed" to form a bicyclic ring means that two rings are attached to each other by sharing two ring atoms. Examples for heterobicycles are indole, indoline, benzofuran, benzothiophene, benzoxazole, benzisoxazole, benzothiazole, benzisothiazole, benzimidazole, benzimidazoline, benzotriazole, [1,24]triazolo[1,5a]pyridine, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, imidazopyridazine, pyrazolopyrimidine, purine and pteridine. Accordingly, a heterobicycle may have up to 12 ring atoms.

"Aromatic heterobicyclyl" or "aromatic heterobicycle" means an aromatic heterocycle which is condensed with phenyl or an additional aromatic heterocycle to form a bicyclic ring system. "Condensed" to form a bicyclic ring means that two rings are attached to each other by sharing two ring atoms. Examples for aromatic heterobicycles are indole, benzofuran, benzothiophene, benzoxazole, benzisoxazole, benzothiazole, benzisothiazole, benzimidazole, benzotriazole, [1,24]triazolo[1,5a]pyridine, quinoline, isoquinoline, imidazopyridazine, pyrazolopyrimidine, purine and pteridine.

"Non-aromatic heterobicyclyl" or "non-aromatic heterobicycle" means heterobicyclyl or heterobicycle other than an aromatic heterobicyclyl or aromatic heterobicycle.

Preferred compounds of formula (I) are those compounds in which one or more of the residues contained therein have the meanings given below, with all combinations of preferred substituent definitions being a subject of the present invention. With respect to all preferred compounds of the formulae (I) the present invention also includes all tautomeric and stereoisomeric forms and mixtures thereof in all ratios, and their pharmaceutically acceptable salts.

In preferred embodiments of the present invention, the substituents mentioned below independently have the following meaning. Hence, one or more of these substituents can have the preferred or more preferred meanings given below.

Preferred compounds of the present invention are those of formula (Ia) or (Ib)

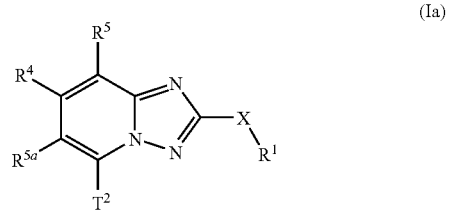

(Ia)

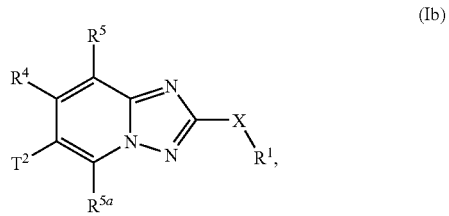

(Ib)

wherein X, $T^2$, $R^1$, $R^4$, $R^5$, $R^{5a}$ have the meaning as indicated above.

Preferably, X is NR⁶.

Preferably, R⁶ is H or CH₃. More preferred is R⁶H.

Preferably, R¹ is C(O)R⁷, C(O)OR⁷, C(O)N(R⁷R⁷ᵃ) or C₁₋₆ alkyl optionally substituted with one or more R⁸.

Preferably, R⁴ and R⁵ are independently H or CH₃. More preferred are R⁴ and R⁵H.

Preferably, R⁵ᵃ is H or C₁₋₆ alkyl. More preferred is R⁵ᵃH or CH₃, even more preferred H.

Preferably, R⁷ is T¹; unsubstituted C₁₋₆ alkyl; or C₁₋₆ alkyl substituted with one R⁸.

Preferably, R⁷ is methyl.

Preferably, R⁸ is T¹; OH; OC₁₋₆ alkyl; (O)O—C₁₋₆ alkyl; C(O)NH₂; C(O)NH—C₁₋₆ alkyl; or C(O)N(C₁₋₆ alkyl)₂.

Preferably, T¹ is unsubstituted C₃₋₇ cycloalkyl; unsubstituted non-aromatic heterocyclyl; or unsubstituted aromatic heterocyclyl.

Preferably, T¹ is cyclopropyl; cyclohexyl; furyl; or pyridyl.

Preferably, R¹³, R¹³ᵃ, R¹³ᵇ, R¹³ᶜ are H.

Preferably, T² is T³.

Preferably, T³ is unsubstituted phenyl; substituted phenyl; unsubstituted heterocyclyl; substituted heterocyclyl; unsubstituted heterobicyclyl; or substituted heterobicyclyl.

Preferably, T³ is unsubstituted or substituted with up to three R¹⁴, which are the same or different.

Preferably, T³ is phenyl; pyrrolyl; furyl; thienyl; oxazolyl; thiazolyl; pyridyl and N-oxide thereof; pyrimidinyl; indolyl; indolinyl; indazolyl; quinolinyl, isoquinolinyl, benzodioxolyl, dihydrobenzofuryl; dihydrobenzoxazinyl; or benzodioxanyl.

Preferably, R¹⁴ is oxo (=O), where the ring is at least partially substituted; F; Cl; N(R¹⁵R¹⁵ᵃ); OR¹⁵; C(O)OR¹⁵; C(O)N(R¹⁵R¹⁵ᵃ); N(R¹⁵)S(O)₂R¹⁵ᵃ; S(O)₂N(R¹⁵R¹⁵ᵃ); S(O)₂R¹⁵; S(O)R¹⁵; N(R¹⁵)C(O)R¹⁵ᵃ; or C₁₋₆ alkyl, which is optionally substituted with one or more R¹⁶.

Preferably, R¹⁵, R¹⁵ᵃ are independently selected from the group consisting of H; CH₃; CH₂CH₃; n-butyl; tert.-butyl; iso-propyl; 2-ethylbutyl; CF₃; CH₂CH₂OH; CH₂CH₂CH₂OH; CH₂C(CH₃)₂CH₂OH; CH₂CH₂OCH₃; CH₂CH₂NH₂; CH₂CH₂CF₃; CH₂CH₂NHCH₃; and CH₂CH₂N(CH₃)₂.

Preferably, R¹⁶ is F; Cl; Br; OH; CH₃; or CH₂CH₃.

Preferably, R¹⁴ is F; Cl; NH₂; NH(CH₃); N(CH₃)₂; NH(CH₂)₂OH; N((CH₂)₂OH)₂; OH; OCH₃; OCF₃; OCH(CH₃)₂; CH₂OH; CH₂OCH₃; CH₂Br; CH₃; CH₂CH₃; CH(CH₃)₂; C(CH₃)₃; CF₃; C(O)OH; C(O)OCH₃; C(O)OCH₂CH₃; C(O)NH₂; C(O)NH(CH₃); C(O)(CH₃)₂; C(O)NHCH₂CH₃; C(O)N(CH₃)CH₂CH₃; C(O)NHCH₂CH₂OH; C(O)N(CH₃)CH₂CH₂OH; C(O)NHCH₂CH₂OCH₃; C(O)N(CH₃)CH₂CH₂OCH₃; C(O)NHCH₂CH₂NH₂; C(O)N(CH₃)CH₂CH₂NH₂; C(O)NHCH₂CH₂NHCH₃; C(O)N(CH₃)CH₂CH₂NHCH₃; C(O)NHCH₂CH₂N(CH₃)₂; C(O)N(CH₃)CH₂CH₂N(CH₃)₂; HNC(O)H₃; S(O)₂CH₃; S(O)CH₃; S(O)₂NH₂; S(O)₂NHC(CH₃)₃; S(O)₂NHCH₂CH(CH₂CH₃)₂; S(O)₂NH(CH₂)₂OH; S(O)₂NH(CH₂)₂CF₃; S(O)₂NH(CH₂)₃OH; S(O)₂NHCH₂C(CH₃)₂CH₂OH; S(O)₂NH(CH₂)₂OCH₃; or NHS(O)₂CH₃.

Compounds of formula (I) in which some or all of the above-mentioned groups have the preferred meanings are also an object of the present invention.

Preferred compounds of the present invention are those which are selected from the group consisting of Cyclopropanecarboxylic acid [5-(2-dimethylamino-phenyl)-[1,2,4]triazolo[1,5-a]pyridin-2-yl]-amide;

Cyclopropanecarboxylic acid [5-(3-chloro-4-fluoro-phenyl)-[1,2,4]triazolo[1,5-a]pyridin-2-yl]-amide;

Cyclopropanecarboxylic acid (5-phenyl-[1,2,4]triazolo[1,5-a]pyridin-2-yl)-amide;

Cyclopropanecarboxylic acid [5-(3-trifluoromethoxy-phenyl)-[1,2,4]triazolo[1,5-a]pyridin-2-yl]-amide;

Cyclopropanecarboxylic acid [5-((E)-styryl)-[1,2,4]triazolo[1,5-a]pyridin-2-yl]-amide;

Cyclopropanecarboxylic acid [5-(3-chloro-phenyl)-[1,2,4]triazolo[1,5-a]pyridin-2-yl]-amide;

Cyclopropanecarboxylic acid (5-thiophen-3-yl-[1,2,4]triazolo[1,5-a]pyridin-2-yl)-amide;

Cyclopropanecarboxylic acid [5-(4-methoxy-phenyl)-[1,2,4]triazolo[1,5-a]pyridin-2-yl]-amide;

3-Cyclohexyl-N-[5-(4-hydroxy-3,5-dimethyl-phenyl)-[1,2,4]triazolo[1,5-a]pyridin-2-yl]-propionamide;

Cyclohexanecarboxylic acid (5-thiophen-3-yl-[1,2,4]triazolo[1,5-a]pyridin-2-yl)-amide;

Furan-2-carboxylic acid [5-(3-fluoro-phenyl)-[1,2,4]triazolo[1,5-a]pyridin-2-yl]-amide;

Furan-2-carboxylic acid [5-(4-hydroxy-3,5-dimethyl-phenyl)-[1,2,4]triazolo[1,5-a]pyridin-2-yl]-amide;

3-Methoxy-N-(5-thiophen-3-yl-[1,2,4]triazolo[1,5-a]pyridin-2-yl)-propionamide;

N-[6-(3-Hydroxymethyl-phenyl)-[1,2,4]triazolo[1,5-a]pyridin-2-yl]-3,3-dimethyl-butyramide;

Cyclopropanecarboxylic acid [6-(2-dimethylamino-phenyl)-[1,2,4]triazolo[1,5-a]pyridin-2-yl]-amide;

N-[6-(4-Hydroxy-phenyl)-[1,2,4]triazolo[1,5-a]pyridin-2-yl]-acetamide;

4-[2-(Cyclopropanecarbonyl-amino)-[1,2,4]triazolo[1,5-a]pyridin-5-yl]-N-(2-dimethylamino-ethyl)-benzamide;

4-[2-(Cyclopropanecarbonyl-amino)-[1,2,4]triazolo[1,5-a]pyridin-5-yl]-N-(2-hydroxy-ethyl)-benzamide;

Cyclopropanecarboxylic acid (5-furan-3-yl-[1,2,4]triazolo[1,5-a]pyridin-2-yl)-amide;

N-[5-(3-Amino-phenyl)-[1,2,4]triazolo[1,5-a]pyridin-2-yl]-3-pyridin-3-yl-propionamide;

Cyclopropanecarboxylic acid [5-(3-methanesulfonylamino-phenyl)-[1,2,4]triazolo[1,5-a]pyridin-2-yl]-amide;

3-[2-(Cyclopropanecarbonyl-amino)-[1,2,4]triazolo[1,5-a]pyridin-6-yl]-N,N-dimethylbenzamide;

N-[6-(3-Methanesulfonylphenyl)-[1,2,4]triazolo[1,5-a]pyridin-2-yl]acetamide;

N-[6-(3-Acetylaminophenyl)-[1,2,4]triazolo[1,5-a]pyridin-2-yl]acetamide;

N-[6-(4-Methoxyphenyl)-[1,2,4]triazolo[1,5-a]pyridin-2-yl]acetamide;

N-[6-(1H-Indol-5-yl)-[1,2,4]triazolo[1,5-a]pyridin-2-yl]acetamide;

N-[6-(1H-Indol-4-yl)-[1,2,4]triazolo[1,5-a]pyridin-2-yl]acetamide;

N-[6-(2,3-Dihydrobenzofuran-5-yl)-[1,2,4]triazolo[1,5-a]pyridin-2-yl]acetamide;

N-[6-(2,4-Dimethoxyphenyl)-[1,2,4]triazolo[1,5-a]pyridin-2-yl]acetamide;

N-(6-Pyridin-3-yl-[1,2,4]triazolo[1,5-a]pyridin-2-yl)acetamide;

N-[6-(5-Methoxypyridin-3-yl)-[1,2,4]triazolo[1,5-a]pyridin-2-yl]acetamide;

N-[6-(4-Methoxy-3-trifluoromethylphenyl)-[1,2,4]triazolo[1,5-a]pyridin-2-yl]acetamide;

N-(6-Pyridin-4-yl-[1,2,4]triazolo[1,5-a]pyridin-2-yl)acetamide;

N-[6-(6-Aminopyridin-3-yl)-[1,2,4]triazolo[1,5-a]pyridin-2-yl]acetamide;

N-[6-(2,3-Dihydrobenzo[1,4]dioxin-6-yl)-[1,2,4]triazolo[1,5-a]pyridin-2-yl]acetamide;

N-[6-(3,4-Dichloro-phenyl)-[1,2,4]triazolo[1,5-a]pyridin-2-yl]-acetamide;

5-(2-Acetylamino-[1,2,4]triazolo[1,5-a]pyridin-6-yl)-2-fluoro-N-(2-hydroxy-ethyl)-benzamide;
N-[6-(3-Dimethylsulfamoyl-phenyl)-[1,2,4]triazolo[1,5-a]pyridin-2-yl]-acetamide;
N-[6-(2,5-Dimethoxy-phenyl)-[1,2,4]triazolo[1,5-a]pyridin-2-yl]-acetamide;
N-[6-(3,4,5-Trimethoxy-phenyl)-[1,2,4]triazolo[1,5-a]pyridin-2-yl]-acetamide;
N-{6-[3-(2-Hydroxy-ethylsulfamoyl)-phenyl]-[1,2,4]triazolo[1,5-a]pyridin-2-yl}-acetamide;
N-[6-(3-Hydroxy-phenyl)-[1,2,4]triazolo[1,5-a]pyridin-2-yl]-acetamide;
N-[6-(2-Methoxy-phenyl)-[1,2,4]triazolo[1,5-a]pyridin-2-yl]-3-methyl-butyramide;
2-Cyclohexyl-N-[6-(2-methoxy-phenyl)-[1,2,4]triazolo[1,5-a]pyridin-2-yl]-acetamide;
2-Methoxy-N-[6-(2-methoxy-phenyl)-[1,2,4]triazolo[1,5-a]pyridin-2-yl]-acetamide;
Furan-2-carboxylic acid [6-(2-methoxy-phenyl)-[1,2,4]triazolo[1,5-a]pyridin-2-yl]-amide;
Isoxazole-5-carboxylic acid [6-(2-methoxy-phenyl)-[1,2,4]triazolo[1,5-a]pyridin-2-yl]amide;
N-[6-(2-Methoxy-phenyl)-[1,2,4]triazolo[1,5-a]pyridin-2-yl]-3-phenyl-propionamide;
N-[6-(6-Methoxy-pyridin-3-yl)-[1,2,4]triazolo[1,5-a]pyridin-2-yl]-acetamide;
N-[6-(5-Methanesulfonyl-pyridin-3-yl)-[1,2,4]triazolo[1,5-a]pyridin-2-yl]-acetamide;
N-[6-(3-Methanesulfonyl-phenyl)-[1,2,4]triazolo[1,5-a]pyridin-2-yl]-2-methoxy-acetamide;
N-[6-(3-Methanesulfonyl-phenyl)-[1,2,4]triazolo[1,5-a]pyridin-2-yl]-propionamide;
Furan-2-carboxylic acid [6-(3-methanesulfonyl-phenyl)-[1,2,4]triazolo[1,5-a]pyridin-2-yl]-amide;
N-[6-(3,4-Dimethoxy-phenyl)-[1,2,4]triazolo[1,5-a]pyridin-2-yl]-acetamide;
N-[6-(3-Methoxyphenyl)-[1,2,4]triazolo[1,5-a]pyridin-2-yl)acetamide;
N-[6-(3-Sulfamoylphenyl)-[1,2,4]triazolo[1,5-a]pyridin-2-yl)acetamide;
3-[2-Acetylamino-[1,2,4]triazolo[1,5-a]pyridin-6-yl)benzamide;
3-[2-Acetylamino-[1,2,4]triazolo[1,5-a]pyridin-6-yl)-N-methylbenzamide;
5-[2-Acetylamino-[1,2,4]triazolo[1,5-a]pyridin-6-yl)-N,N-dimethylbenzamide;
4-[2-Acetylamino-[1,2,4]triazolo[1,5-a]pyridin-6-yl)benzamide;
N-[6-(3-Methylsulfamoylphenyl)-[1,2,4]triazolo[1,5-a]pyridin-2-yl]acetamide;
N-[6-(3-Isopropylsulfamoylphenyl)-[1,2,4]triazolo[1,5-a]pyridin-2-yl]acetamide;
N-[6-(3-tertButylsulfamoylphenyl)-[1,2,4]triazolo[1,5-a]pyridin-2-yl]acetamide;
N-[6-(3-Butylsulfamoylphenyl)-[1,2,4]triazolo[1,5-a]pyridin-2-yl]acetamide;
N-(6-Isoquinolin-6-yl)-[1,2,4]triazolo[1,5-a]pyridin-2-yl)acetamide;
N-[6-(4-Hydroxy-3,5-dimethyl-phenyl)-[1,2,4]triazolo[1,5-a]pyridin-2-yl]-acetamide;
N-[6-(4-Hydroxy-3-methoxy-phenyl)-[1,2,4]triazolo[1,5-a]pyridin-2-yl]-acetamide;
N-[6-(2-Methoxy-phenyl)-[1,2,4]triazolo[1,5-a]pyridin-2-yl]-acetamide;
Cyclopropanecarboxylic acid [6-(6-amino-pyridin-3-yl)-[1,2,4]triazolo[1,5-a]pyridin-2-yl]-amide;
N-[6-(4-Hydroxy-3-methoxy-phenyl)-[1,2,4]triazolo[1,5-a]pyridin-2-yl]-3,3-dimethyl-butyramide;
N-[6-(3-Methanesulfonylamino-phenyl)-[1,2,4]triazolo[1,5-a]pyridin-2-yl]-acetamide;
N-[6-(4-Fluoro-phenyl)-[1,2,4]triazolo[1,5-a]pyridin-2-yl]-acetamide;
N-[6-(3-Methanesulfonyl-phenyl)-[1,2,4]triazolo[1,5-a]pyridin-2-yl]-butyramide;
N-(6-Pyrimidin-5-yl-[1,2,4]triazolo[1,5-a]pyridin-2-yl)-acetamide;
N-[6-(5-Methoxy-pyridin-3-yl)-[1,2,4]triazolo[1,5-a]pyridin-2-yl]-acetamide;
N-[6-(3-Fluoro-phenyl)-[1,2,4]triazolo[1,5-a]pyridin-2-yl]-acetamide;
N-[6-(3,5-Difluoro-phenyl)-[1,2,4]triazolo[1,5-a]pyridin-2-yl]-acetamide;
N-[6-(3-Trifluoromethyl-phenyl)-[1,2,4]triazolo[1,5-a]pyridin-2-yl]-acetamide;
N-{6-[5-(2-Hydroxy-ethylsulfamoyl)-pyridin-3-yl]-[1,2,4]triazolo[1,5-a]pyridin-2-yl}-acetamide;
N-(6-Thiophen-3-yl-[1,2,4]triazolo[1,5-a]pyridin-2-yl)-acetamide;
N-(8-Methyl-6-pyridin-3-yl-[1,2,4]triazolo[1,5-a]pyridin-2-yl)-acetamide;
N-[6-(3-Methanesulfonyl-phenyl)-8-methyl-[1,2,4]triazolo[1,5-a]pyridin-2-yl]-acetamide;
N-[6-(3-Hydroxy-4-methoxy-phenyl)-[1,2,4]triazolo[1,5-a]pyridin-2-yl]-acetamide;
N-[6-(5-Trifluoromethyl-pyridin-3-yl)-[1,2,4]triazolo[1,5-a]pyridin-2-yl]-acetamide;
N-[6-(6-Trifluoromethyl-pyridin-3-yl)-[1,2,4]triazolo[1,5-a]pyridin-2-yl]-acetamide;
N-[6-(4-Chloro-3-methanesulfonyl-phenyl)-[1,2,4]triazolo[1,5-a]pyridin-2-yl]-acetamide;
N-[6-(3-Aminophenyl)-[1,2,4]triazolo[1,5-a]pyridin-2-yl]acetamide;
N-{6-[3-(Methanesulfonylmethylamino)phenyl]-[1,2,4]triazolo[1,5-a]pyridin-2-yl}acetamide;
N-[6-(6-Aminopyridin-3-yl)-[1,2,4]triazolo[1,5-a]pyridin-2-yl]-N-benzamide;
Cyclohexanecarboxylic acid [6-(3-methanesulfonylaminophenyl)-[1,2,4]triazolo[1,5-a]pyridin-2-yl]-amide;
Cyclopropanecarboxylic acid [6-(3-methanesulfonylaminophenyl)-[1,2,4]triazolo[1,5-a]pyridin-2-yl]-amide;
N-[6-(5-(Methanesulfonylaminopyridin-3-yl)-[1,2,4]triazolo[1,5-a]pyridin-2-yl]-N-acetamide;
N-[6-(6-Chloro-5-(Methanesulfonylaminopyridin-3-yl)-[1,2,4]triazolo[1,5-a]pyridin-2-yl]-N-acetamide;
N-[6-(5-Butylsulfamoylpyridin-3-yl)-[1,2,4]triazolo[1,5-a]pyridin-2-yl]acetamide;
3-(2-acetamido-[1,2,4]triazolo[1,5-a]pyridin-6-yl)benzoic acid;
N-(6-(4-(trifluoromethoxy)phenyl)-[1,2,4]triazolo[1,5-a]pyridin-2-yl)acetamide;
N-(6-(3,4-difluorophenyl)-[1,2,4]triazolo[1,5-a]pyridin-2-yl)acetamide;
N-(6-(benzo[d][1,3]dioxol-5-yl)-[1,2,4]triazolo[1,5-a]pyridin-2-yl)acetamide;
4-(2-acetamido-[1,2,4]triazolo[1,5-a]pyridin-6-yl)-N-(2-hydroxyethyl)benzamide;
N-(6-(4-fluoro-3-(trifluoromethyl)phenyl)-[1,2,4]triazolo[1,5-a]pyridin-2-yl)acetamide;
N-(6-(3-fluoro-4-(trifluoromethyl)phenyl)-[1,2,4]triazolo[1,5-a]pyridin-2-yl)acetamide;
N-(6-(3,4-dimethoxy-2-methylphenyl)-[1,2,4]triazolo[1,5-a]pyridin-2-yl)acetamide;

N-(6-(3-isopropoxy-4-methoxyphenyl)-[1,2,4]triazolo[1,5-a]pyridin-2-yl)acetamide;
N-(6-(4-(trifluoromethoxy)-3-(trifluoromethyl)phenyl)-[1,2,4]triazolo[1,5-a]pyridin-2-yl)acetamide;
N-[6-(4-Chloro-2-trifluoromethyl-phenyl)-[1,2,4]triazolo[1,5-a]pyridin-2-yl]-acetamide;
N-[6-(4-Fluoro-3-methoxy-phenyl)-[1,2,4]triazolo[1,5-a]pyridin-2-yl]-acetamide;
N-[6-(3-Methoxy-pyridin-4-yl)-[1,2,4]triazolo[1,5-a]pyridin-2-yl]-acetamide;
N-(6-Isoquinolin-4-yl-[1,2,4]triazolo[1,5-a]pyridin-2-yl)-acetamide;
N-(6-Quinolin-3-yl-[1,2,4]triazolo[1,5-a]pyridin-2-yl)-acetamide;
N-[6-(6-Fluoro-pyridin-3-yl)-[1,2,4]triazolo[1,5-a]pyridin-2-yl]-acetamide;
N-{6-[3-(2-Methoxy-ethylsulfamoyl)-phenyl]-[1,2,4]triazolo[1,5-a]pyridin-2-yl}-acetamide;
N-{6-[3-(3-Hydroxy-propylsulfamoyl)-phenyl]-[1,2,4]triazolo[1,5-a]pyridin-2-yl}-acetamide;
N-(6-{3-[Bis-(2-hydroxy-ethyl)-sulfamoyl]-phenyl}-[1,2,4]triazolo[1,5-a]pyridin-2-yl)-acetamide;
N-{6-[3-(3-Hydroxy-2,2-dimethyl-propylsulfamoyl)-phenyl]-[1,2,4]triazolo[1,5-a]pyridin-2-yl}-acetamide;
N-[6-(5-Sulfamoyl-pyridin-3-yl)-[1,2,4]triazolo[1,5-a]pyridin-2-yl]-acetamide;
N-{6-[5-(3,3,3-Trifluoro-propylsulfamoyl)-pyridin-3-yl]-[1,2,4]triazolo[1,5-a]pyridin-2-yl}-acetamide;
N-[6-(5-tert-Butylsulfamoyl-pyridin-3-yl)-[1,2,4]triazolo[1,5-a]pyridin-2-yl]-acetamide;
N-{6-[5-(2-Ethyl-butylsulfamoyl)-pyridin-3-yl]-[1,2,4]triazolo[1,5-a]pyridin-2-yl}-acetamide;
2-[6-(3,4-Dimethoxy-phenyl)-[1,2,4]triazolo[1,5-a]pyridin-2-ylamino]-ethanol;
N-(5-methyl-6-(5-(methylsulfonyl)pyridin-3-yl)-[1,2,4]triazolo[1,5-a]pyridin-2-yl)acetamide;
N-(8-methyl-6-(5-(methylsulfonyl)pyridin-3-yl)-[1,2,4]triazolo[1,5-a]pyridin-2-yl)acetamide;
N,N-dimethyl-6-(5-(methylsulfonyl)pyridin-3-yl)-[1,2,4]triazolo[1,5-a]pyridin-2-amine;
N-(6-(3,4-dimethoxyphenyl)-5-methyl-[1,2,4]triazolo[1,5-a]pyridin-2-yl)acetamide;
N-(6-(3,4-dimethoxyphenyl)-8-methyl-[1,2,4]triazolo[1,5-a]pyridin-2-yl)acetamide;
1-(2-hydroxyethyl)-3-(6-(5-(methylsulfonyl)pyridin-3-yl)-[1,2,4]triazolo[1,5-a]pyridin-2-yl)urea;
1-(6-(3,4-dimethoxyphenyl)-[1,2,4]triazolo[1,5-a]pyridin-2-yl)-3-(2-hydroxyethyl)urea;
1-(6-(3,4-dimethoxyphenyl)-[1,2,4]triazolo[1,5-a]pyridin-2-yl)-3-methylurea;
6-(3,4-dimethoxyphenyl)-N-methyl-[1,2,4]triazolo[1,5-a]pyridin-2-amine;
Methyl 6-(3,4-dimethoxyphenyl)-[1,2,4]triazolo[1,5-a]pyridin-2-ylcarbamate; and
N-(6-(4-hydroxyphenyl)-[1,2,4]triazolo[1,5-a]pyridin-2-yl)acetamide.

Prodrugs of the compounds of the present invention are also within the scope of the present invention.

"Prodrug" means a derivative that is converted into a compound according to the present invention by a reaction with an enzyme, gastric acid or the like under a physiological condition in the living body, e.g. by oxidation, reduction, hydrolysis or the like, each of which is carried out enzymatically. Examples of a prodrug are compounds, wherein the amino group in a compound of the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods.

Metabolites of compounds of formula (I) are also within the scope of the present invention.

The term "metabolites" refers to all molecules derived from any of the compounds according to the present invention in a cell or organism, preferably mammal.

Preferably the term relates to molecules which differ from any molecule which is present in any such cell or organism under physiological conditions The structure of the metabolites of the compounds according to the present invention will be obvious to any person skilled in the art, using the various appropriate methods.

Where tautomerism, like e.g. keto-enol tautomerism, of compounds of general formula (I) may occur, the individual forms, like e.g. the keto and enol form, are comprised separately and together as mixtures in any ratio. Same applies for stereoisomers, like e.g. enantiomers, cis/trans isomers, conformers and the like.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of formula (I) may be obtained from stereoselective synthesis using optically pure starting materials.

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means approved by a regulatory agency such as the EMEA (Europe) and/or the FDA (US) and/or any other national regulatory agency for use in animals, preferably in humans.

The present invention furthermore includes all solvates of the compounds according to the invention.

The present invention provides compounds of formula (I) as kinase inhibitors, especially as Itk or PI3K inhibitors. The compounds of formula (I) may inhibit one or both of these kinases, optionally in addition to other kinases mentioned above without being limited by theory.

Accordingly, the compounds of the present invention are useful for the prevention or treatment of immunological disorders (e.g. immune or autoimmune diseases), inflammatory disorders or allergic disorders.

Thus, another object of the present invention is a compound of the present invention or a pharmaceutically acceptable salt thereof for use as a medicament.

Yet another object of the present invention is the use of a compound of the present invention or a pharmaceutically acceptable salt thereof for the manufacture of a medicament for the treatment or prophylaxis of diseases and disorders associated with Itk or PI3K, preferably PI3Kγ.

"Itk", "Itk kinase" or "It kinase" means Interleukin-2 (IL-2)-inducible T-cell kinase (also known as Emt or Tsk).

According to the present invention "PI3K" or "PI3 kinase" includes all members of the PI3K family comprising class IA (e.g. PI3K alpha, beta and delta), class IB (e.g. PI3K gamma), class II (e.g. PI3KC2 alpha, beta and gamma) and class III (e.g. Vps34 yeast homologue).

"PI3Kγ" means PI3Kγ protein, the only member of PI3K class IB (also referred to as p110-gamma). A human cDNA encoding the PI3Kγ protein of a predicted 120 kD 1050 amino acid residue long polypeptide was described (Stoyanow et al., 1995, Science 269:690-693). The human PI3Kγ protein is encoded by the PI3KCG gene which comprises 10 exons and is located on chromosome 7q22 (Kratz et al., 2002, Blood 99:372-374).

"PI3Kδ" means PI3Kδ protein, a member of PI3K class class IA (also referred to as p110-delta). A human cDNA encoding the PI3Kδ protein of 1,044 amino acids was reported (Vanhaesebroeck et al., 1997, Proc. Natl. Acad. Sci. 94:4330-4335). The human PI3Kδ protein is encoded by the PI3KCD gene which was mapped to chromosome 1p3.2 (Seki et al., 1997, DNA Research 4:355-358).

Yet another object of the present invention is the use of a compound of the present invention or a pharmaceutically acceptable salt thereof for the manufacture of a medicament for the treatment or prophylaxis of immunological, inflammatory or allergic disorders.

More specifically, preferred disorders are autoimmune diseases; organ and bone marrow transplant rejection; graft-versus-host disease; acute or chronic inflammation; contact dermatitis; psoriasis; rheumatoid arthritis; multiple sclerosis; type I diabetes; inflammatory bowel disease; Crohn's disease; ulcerative colitis; graft versus host disease; lupus erythematosus; asthma; chronic obstructive pulmonary disease (COPD); acute respiratory distress syndrome (ARDS); bronchitis; conjunctivitis; dermatitis; or allergic rhinitis.

Quite more preferred are rheumatoid arthritis (RA), systemic lupus erythematosus (SLE), psoriasis, multiple sclerosis (MS), asthma and chronic obstructive pulmonary disease (COPD).

Rheumatoid arthritis (RA) is a chronic progressive, debilitating inflammatory disease that affects approximately 1% of the world's population. RA is a symmetric polyarticular arthritis that primarily affects the small joints of the hands and feet. In addition to inflammation in the synovium, the joint lining, the aggressive front of tissue called pannus invades and destroys local articular structures (Firestein 2003, Nature 423:356-361).

Systemic lupus erythematosus (SLE) is a chronic inflammatory disease generated by T cell-mediated B-cell activation, which results in glomerulonephritis and renal failure. Human SLE is characterized at early stages by the expansion of long-lasting autoreactive CD4$^+$ memory cells (D'Cruz et al., 2007, Lancet 369(9561):587-596).

Psoriasis is a chronic inflammatory dermatosis that affects approximately 2% of the population. It is characterized by red, scaly skin patches that are usually found on the scalp, elbows, and knees, and may be associated with severe arthritis. The lesions are caused by abnormal keratinocyte proliferation and infiltration of inflammatory cells into the dermis and epidermis (Schon et al., 2005, New Engl. J. Med. 352: 1899-1912).

Multiple sclerosis (MS) is an inflammatory and demyelating neurological disease. It has bee considered as an autoimmune disorder mediated by CD4+ type 1 T helper cells, but recent studies indicated a role of other immune cells (Hemmer et al., 2002, Nat. Rev. Neuroscience 3, 291-301).

Asthma is a complex syndrome with many clinical phenotypes in both adults and children. Its major characteristics include a variable degree of air flow obstruction, bronchial hyperresponsiveness, and airway inflammation (Busse and Lemanske, 2001, N. Engl. J. Med. 344:350-362).

Chronic obstructive pulmonary disease (COPD) is characterized by inflammation, airflow limitation that is not fully reversible, and a gradual loss of lung function. In COPD, chronic inhalation of irritants causes an abnormal inflammatory response, remodeling of the airways, and restriction of airflow in the lungs. The inhaled irritant is usually tobacco smoke, but occupational dust and environmental pollution are variably implicated (Shapiro 2005, N. Engl. J. med. 352, 2016-2019).

Diseases and disorders associated especially with PI3K are cancer and cardiovascular disorders.

Yet another aspect of the present invention is the use of a compound of the present invention or a pharmaceutically acceptable salt thereof for the manufacture of a medicament for the treatment or prophylaxis of cancer or cardiovascular disorders, more specifically myocardial infarction, stroke, ischemia or atherosclerosis.

Cancer comprises a group of diseases characterized by uncontrolled growth and spread of abnormal cells. All types of cancers generally involve some abnormality in the control of cell growth, division and survival, resulting in the malignant growth of cells. Key factors contributing to said malignant growth of cells are independence from growth signals, insensitivity to anti-growth signals, evasion of apoptosis, limitless replicative potential, sustained angiogenesis, tissue invasion and metastasis, and genome instability (Hanahan and Weinberg, 2000. The Hallmarks of Cancer. Cell 100, 57-70).

Typically, cancers are classified as hematological cancers (for example leukemias and lymphomas) and solid cancers such as sarcomas and carcinomas (for example cancers of the brain, breast, lung, colon, stomach, liver, pancreas, prostate, ovary).

Another object of the present invention is a method for treating, controlling, delaying or preventing in a mammalian patient in need of the treatment of one or more conditions selected from the group consisting of diseases and disorders associated with Itk; and PI3K, wherein the method comprises the administration to said patient a therapeutically effective amount of a compound according to present invention or a pharmaceutically acceptable salt thereof.

Yet another object is a method for treating, controlling, delaying or preventing in a mammalian patient in need of the treatment of one or more conditions selected from the group consisting of immunological; inflammatory; and allergic disorders, wherein the method comprises the administration to said patient a therapeutically effective amount of a compound according to the present invention or a pharmaceutically acceptable salt thereof.

More specifically the one or more conditions are selected from the group consisting of autoimmune diseases; organ and bone marrow transplant rejection; graft-versus-host disease; acute or chronic inflammation; contact dermatitis; psoriasis; rheumatoid arthritis; multiple sclerosis; type I diabetes; inflammatory bowel disease; Crohn's disease; ulcerative colitis; graft versus host disease; lupus erythematosus; asthma; chronic obstructive pulmonary disease (COPD); acute respiratory distress syndrome (ARDS); bronchitis; conjunctivitis; dermatitis; and allergic rhinitis.

More preferred are rheumatoid arthritis (RA), systemic lupus erythematosus (SLE), psoriasis, multiple sclerosis (MS), asthma and chronic obstructive pulmonary disease (COPD).

Yet another object of the present invention is a method for treating, controlling, delaying or preventing in a mammalian patient in need of the treatment of one or more conditions selected from the group consisting of cancer; and cardiovascular disorders, more specifically myocardial infarction, stroke, ischemia or atherosclerosis, wherein the method comprises the administration to said patient a therapeutically effective amount of a compound according to the present invention or a pharmaceutically acceptable salt thereof.

As used herein, the term "treating" or "treatment" is intended to refer to all processes, wherein there may be a slowing, interrupting, arresting, or stopping of the progression of a disease, but does not necessarily indicate a total elimination of all symptoms.

Without intending to be limited by theory, the compounds of the invention modulate T cell and mast cell activation via inhibition of Itk. The inhibition of T cell activation is therapeutically useful for suppressing immune functions. Therefore the inhibition of Itk is useful for preventing and treating a variety of immune disorders, including autoimmune diseases, organ and bone marrow transplant rejection, graft-versus-host disease, and inflammatory diseases.

In particular, the compounds of the invention may be used to prevent or treat acute or chronic inflammation, allergies, contact dermatitis, psoriasis, rheumatoid arthritis, multiple sclerosis, type I diabetes, inflammatory bowel disease, Crohn's disease, ulcerative colitis, graft versus host disease and lupus erythematosus.

Inhibitors of mast cell activation and degranulation prevent the release of proinflammatory mediators and cytokines. Thus inhibition of Itk may be used to prevent and treat inflammatory and allergic disorders, including asthma, chronic obstructive pulmonary disease (COPD), acute respiratory distress syndrome (ARDS), bronchitis, conjunctivitis, dermatitis and allergic rhinitis. Other disorders mediated by T cells or mast cells will be known to those of ordinary skill in the art and can also be treated with the compounds of the invention.

Without intending to be limited by theory, the compounds of the invention may also modulate in addition or alternatively immune cell activation via inhibition of PI3K. Especially the important roles of PI3Kδ and PI3Kγ in signaling and other functions of T cells, B cells, neutrophils, macrophages and mast cells indicate that these kinases are valid therapeutic targets for several inflammation-mediated diseases. These diseases comprise rheumatoid arthritis (in which T cells, B cells and neutrophils are involved), systemic lupus erythematosus (in which neutrophils are involved), psoriasis (in which T cells, neutrophils and macrophages are engaged), multiple sclerosis (in which T cells, B cells and mast cells are implicated), asthma (for which T cell and mast cells are important), and chronic obstructive pulmonary disease (which involves neutrophils, macrophages and T cells) (Rommel et al., 2007, Nat. Rev. Immunology 7:191-201).

In some cases, the link between PI3Kδ and PI3Kγ as potential drug targets for specific diseases has been experimentally established by testing the respective PI3K-null mice in animal disease models. Additional pharmacological confirmation was obtained by using small molecule PI3K inhibitors in wild-type mice in which inflammatory diseases were experimentally induced.

Camps and colleagues used structure-based drug design to develop a potent small molecule inhibitor of PIK3γ referred to as AS-605240 (Nat. Med. 2005, 11(9):936-43). It was observed that Pik3cg-null mice were protected against arthritis induced by collagen II-specific antibodies, a murine model of lymphocyte-independent rheumatoid arthritis ($R^{-4}$) associated with neutrophil activation. The effect was associated with impaired neutrophil chemotaxis. Treatment of wildtype mice with oral AS-605420 resulted in reduced clinical and histologic signs of collagen II-antibody-induced arthritis, similar to that seen in the Pik3cg-null mice. Oral AS-605240 also resulted in decreased joint inflammation and damage in a distinct mouse model of lymphocyte-dependent rheumatoid arthritis induced by direct collagen II injection. The authors concluded that PIK3CG inhibition operates on both the neutrophil and lymphocyte arms of chemokine signaling pathways, and thus may be of therapeutic value in various chronic inflammatory diseases.

In the MRL-1pr mouse model of systemic lupus erythematosus (SLE) it was found that intraperitoneal administration of the pharmacologic PI3Kγ inhibitor AS-605240 reduced CD4+ T-cell populations, reduced glomerulonephritis, and prolonged life span (Barber et al., 2005, Nat. Med. 11(9):933-935).

The involvement of PI3 kinases in allergic inflammatory diseases such as asthma was demonstrated through pharmacological inhibition by non-selective PI3K inhibitors such as wortmannin and LY294002. However, these compounds were not selective enough to discriminate between distinct PI3K isoforms (Walker et al., 2006, Drug Discovery Today: Disease Mechanisms, 3(1):63-69).

In another study it was shown that ablation of PI3Kγ in mice (Pi3kcg-/- mice) reduces the severity of experimentally induced acute pancreatitis (Lupia et al., 2004, Am. J. Pathol. 165(6):2003-11).

Using selective PI3Kδ inhibitors it was demonstrated that PI3Kδ plays a role in neutrophil inflammatory responses. Inhibition of PI3Kδ blocked both fMLP- and TNF1α-induced neutrophil superoxide generation and elastase exocytosis (Sadhu et al., 2003, Biochem. Biophys. Res. Commun. 2003 Sep. 5; 308(4):764-769).

The essential role of PI3Kδ in allergic responses was demonstrated by genetic and pharmacological inactivation of PI3Kδ in mast cells. This inhibition leads to to defective SCF-mediated in vitro proliferation, adhesion and migration, and to impaired allergen-IgE-induced degranulation and cytokine release. Moreover, inactivation of PI3Kδ protects mice against anaphylactic allergic responses. Taken together, these studies suggest PI3Kδ as a target for therapeutic intervention in allergy and mast-cell-related diseases (Ali et al., 2004, Nature 423:1007-1011).

Recently, the effect of genetic inactivation of the Pi3kcg gene in mice on systemic cytokine and chemokine responses and allergic airway inflammation was reported. Type 2 cytokine responses (IL-4, IL-5, and IL-13) were significantly decreased in PI3Kδ mutants, whereas type 1 cytokine responses (IFN-γ CXCL10) were robust. For example, induction of respiratory hyper-responsiveness to inhaled methacholine, a hallmark of asthma, was attenuated in PI3Kδ null mice. In summary, these data suggest PI3Kδ as a new target for TH2-mediated airway diseases (Nashed et al., 2007, Eur. J. Immunol. 37:416-424).

Accordingly, diseases and disorders are preferred which are associated with PI3K delta and/or PI3K gamma. Especially preferred are inflammatory and immunoregulatory disorders rheumatoid arthritis, systemic lupus erythematosus, psoriasis, multiple sclerosis, asthma and chronic obstructive pulmonary disease.

As mentioned above, PI3K also plays a role with regard to cancer and cardiovascular disorders.

This may be based on the fact that signaling through PI3Kγ plays an important role for leucocyte, platelet and cardovascular stress sensing. The concerted activation of leukocytes and vessels influences may physiological and pathological responses usually leading to the production of intracellular second messenger molecules such as phosphatidylinositol(3,4,5)-trisphosphate (PIP3), which is produced by PI3Kγ, a crucial signal in both vascular and white blood cells. The study of mice lacking PI3Kγ revealed that the PIP3 signaling pathway controls immune cell and vascular functions such as respiratory burst, cell recruitment, mast cell reactivity, platelet aggregation, endothelial activation and smooth muscle cell contractility. The specificity of these events suggests that inhibition of PI3Kγ may be beneficial for major cardiovascular disorders such as hypertension (Hirsch et al., 2006, Thromb. Haemost. 95(1):29-35).

Myocardial infarction (MI) results from a biphasic ischemia/reperfusion (I/R) injury to the heart, initiating with cardiomyocyte apoptosis (Crow et al., 2004, Circ. Res. 95(10):957-970) and then proceeding to a second wave of inflammation-based tissue damage (Frangogiannis et al., 2002, Cardiovasc. Res. 53 (1):31-47). Recently, it was reported that a small molecule inhibitor of PI3K gamma and delta provided cardioprotection in an animal model of myocardial infarction. This compound, TG100-115, potently inhibits edema and inflammation in response to multiple mediators known to play a role in myocardial infarction. Importantly, this was achieved when dosing after myocardial reperfusion (up to 3 hours after), the same time period when patients are most accessible for therapeutic intervention (Doukas et al., 2006, PNAS 103(52):19866-19871; Doukas et al., 2007, Biochem. Soc. Trans. 35(Pt2):204-206).

The first study to describe point mutations of the PIK3CA gene, which encodes the p110α catalytic subunit, in colorectal, brain, gastric, breast and lung cancers, was reported in 2004 (Samuels et al., 2004, Science 304:554). Subsequently, several additional point mutations were identified in other cancer types (reviewed by Bader et al., 2005, Nat. Rev. Cancer 5(12): 921-929). It was demonstrated that PIK3CA mutants promote cell growth and invasion of human cancer cells and that treatment with the non-selective PI3K inhibitor LY294002 abrogated PIK3A signaling and preferentially inhibited growth of PI3KCA mutant cells (Samuels et al., 2005, Cancer Cell 7(6):561-573), thus suggesting PI3K proteins as promising drug targets for cancer therapy (Hennessy et al., 2005, Nat. Rev. Drug Discovery 4(12):988-1004).

Recently, it was reported that the overexpression of the wild-type PI3K isoforms PI3KIβ (p110β), PI3Kγ (p110δ) or PI3Kδ (p110δ) is sufficient to induce an oncogenic phenotype in cultured cells (Kang et al., 2006, PNAS 103(5): 1289-1294). This oncogenic potential required kinase activity suggesting that inhibitors of this activity may block the transforming capacity. The role of the non-α class I PI3K isoforms in human cancer has not been fully explored but there are reports of elevated expression of PI3Kβ and PI3Kδ in various human cancers (Benistant et al., 2000, Oncogene 19(44): 5083-5090; Knobbe and Reifenberger, 2003, Brain Pathol. 13(4):507-518). In another study it was demonstrated that a selective inhibitor of PI3Kδ (p110delta) inhibited the proliferation and survival of acute myeloid leukemia (AML) cells and increased the cytotoxic effects of a topoisomerase II inhibitor suggesting PI3Kδ as a potential therapeutic target in AML (Billottet et al., 2006, 25(50):6648-6659).

The present invention provides pharmaceutical compositions comprising a compound of formula (I) or a pharmaceutically acceptable salt thereof as active ingredient together with a pharmaceutically acceptable carrier, optionally in combination with one or more other pharmaceutical compositions.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

A pharmaceutical composition of the present invention may comprise one or more additional compounds as active ingredients like one or more compounds of formula (I) not being the first compound in the composition or other Itk or PI3K inhibitors.

Other active ingredients for use in combination with other therapies for the treatment of immune, inflammatory, allergic disorders and may include steroids, leukotriene antagonists, anti-histamines, cyclosporine or rapamycin.

The pharmaceutical compositions of the present invention include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula (I) can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally, for example, as liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula (I) may also be administered parenterally. Solutions or suspensions of these active compounds can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of formula (I) are administered orally.

The effective dosage of active ingredient employed may vary depending on the particular compound employed, the mode of administration, the condition being treated and the severity of the condition being treated. Such dosage may be ascertained readily by a person skilled in the art.

Methods for the synthesis of the compounds of the present invention are described e.g., in Houben-Weyl, Methoden der Organischen Chemie (Methods of Organic Chemistry), Thieme-Verlag, Stuttgart, or Organic Reactions, John Wiley & Sons, New York.

Depending on the circumstances of the individual case, in order to avoid side reactions during the synthesis of a compound of formula (I), it can be necessary or advantageous to temporarily block functional groups by introducing protective groups and to deprotect them in a later stage of the synthesis, or introduce functional groups in the form of precursor groups which in a later stage are converted into the desired functional groups. Such synthesis strategies and protective groups and precursor groups which are suitable in an individual case are known to the person skilled in the art.

If desired, the compounds of the formula (I) can be purified by customary purification procedures, for example by distillation, recrystallization or chromatography. The starting compounds for the preparation of the compounds of the formula (I) are commercially available or can be prepared according to or analogously to literature procedures.

A general route for the synthesis of compounds or formula (I) may start with triazoles of formula (II) which are readily available by conventional methods for the preparation of this type of heterocycle. Such methods are well known for the person skilled in the art.

According to scheme 1 triazole of formula (II), wherein one of $R^{2'}$, $R^{3'}$ is Br and the other is $R^{5a}$, and X, $R^4$, $R^5$ have the meaning as indicated above may react in a first step with $R^1$—X', wherein X' is a suitable leaving group for the substitution reaction with the residue XH and $R^1$ has the meaning as indicated above to yield triazole of formula (III). Suitable groups X' may be selected from the group consisting of halogen; OH; O—$C_{1-6}$ alkyl; O-benzyl; SH; and $NH_2$.

scheme 1

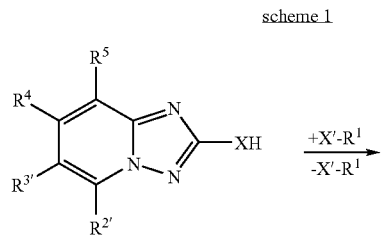

II

III

In a second step Suzuki reaction of triazole (III) with boronic acid $T^2$-$B(OH)_2$ may give compounds of formula (I).

$R^1$—X' and $T^2$-$B(OH)_2$ as suitable starting materials for the synthesis of preferred compounds of the present invention may be purchased from commercially available sources such as Array, Sigma Aldrich, Fluka, ABCR or be synthesized by one skilled in the art.

In a preferred embodiment of the present invention the preparation of triazoles of formula (II), wherein X is NH may start with a pyridine of formula (IV) which is reacted with ethoxycarbonyl isothiocyanate to yield after cyclisation in the presence of hydroxylamine the triazoles of formula (II) as outlined in scheme 2.

scheme 2

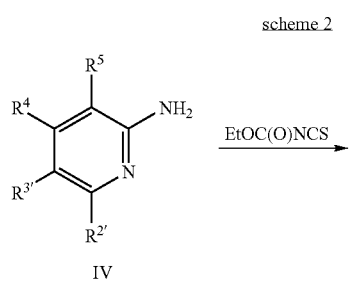

IV

II

In another preferred embodiment of the present invention the preparation of triazoles of formula (III), wherein X is NH and $R^1$ is $C(O)R^7$ may start with a triazole of formula (II) which is reacted with acid chloride $R^7$—C(O)Cl to yield after optional partial hydrolysis of the respective bis-acylated by-product a triazole of formula (III).

EXAMPLES

Analytical Methods

NMR spectra were obtained on a Bruker dpx400. LCMS was carried out on an Agilent 1100 using a ZORBAX® SB-C18, 4.6×150 mm, 5 microns or ZORBAX® SB-C18, 4.6×75 mm, 3.5 micron column. Column flow was 1 ml/min and solvents used were water and acetonitrile (0.1% formic acid) with an injection volume of 10 ul. Wavelengths were 254 and 210 nm. Methods are described below.

Method A

Column: ZORBAX® SB-C18, 4.6×150 mm, 5 microns

| Time (min) | Water | Acetonitrile |
|---|---|---|
| 0 | 95 | 5 |
| 11 | 5 | 95 |
| 13 | 5 | 95 |
| 13.01 | 95 | 5 |
| 14.00 | STOP | |

Method B

Column: ZORBAX® SB-C18, 4.6×75 mm, 3.5 microns

| Time (min) | Water | Acetonitrile |
|---|---|---|
| 0 | 70 | 30 |
| 1.5 | 5 | 95 |
| 4.5 | 5 | 95 |
| 4.51 | 70 | 30 |
| 5.00 | STOP | |

Method C

Column: Gemini C18, 3×30 mm, 3 microns Flow rate: 1.2 ml/min

| Time (min) | Water | Acetonitrile |
|---|---|---|
| 0 | 95 | 5 |
| 3 | 5 | 95 |
| 4.5 | 5 | 95 |
| 4.6 | 95 | 5 |
| 5.00 | STOP | |

Abbreviations

| | |
|---|---|
| DCM | Dichloromethane |
| $Et_3N$ | Triethyl amine |
| $CH_3CN$ | Acetonitrile |
| MeOH | Methanol |
| EtOH | Ethanol |
| $^iPr_2NEt$ | Diisopropylethylamine |
| $NH_2OH$•HCl | Hydroxylaminehydrochloride |
| $PdP(Ph_3)_2Cl_2$ | Bistriphenylphosphino-palladium(II)chloride |

| | |
|---|---|
| CsF | Caesium fluoride |
| DMF | N,N-Dimethylformamide |
| DME | 1,2-Dimethoxyethane |
| HOBt | 1-hydroxybenzotriazole |
| EDC | N-Ethyl-N'-(3-dimethylaminopropyl)carbodiimide hydrochloride |
| $H_2O$ | Water |
| s | singlet |
| d | Doublet |
| dd | Doubledoublet |
| br | Broad |
| t | Triplet |
| m | Multiplet |
| dm | Doublet of multiplets |
| tm | Triplet of multiplets |

Example 1

Preparation of Preferred Compounds of the Present Invention

In a general procedure for the preparation of preferred compounds of the present invention reaction of commercially available 2-amino-6-bromopyridine or 2-amino-5-bromopyridine with ethoxycarbonyl isothiocyanate in DCM at 20° C. affords a thiourea derivative as intermediate product which is subjected to a cyclisation procedure, employing hydroxylamine in a protic solvent ($NH_2OH.HCl$, $^iPr_2NEt$, EtOH/MeOH, $\Delta$), to yield key intermediate 2-amino-5-bromo-[1,2,4]triazolo[1,5-a]pyridine or 2-amino-6-bromo-[1,2,4]triazolo[1,5-a]pyridine. Subsequent acylation of the pyridine using the respective alkyl and aryl acid chloride in the presence of $Et_3N$ in $CH_3CN$ at 20° C. generally gives a bis-acylated product which requires hydrolysis to the mono-acylated product using methanolic ammonia solution at 20° C. The preferred compounds of the present invention are synthesised by coupling of the mono-acylated products with the respective aryl boronic acids or esters under Suzuki reaction conditions using $PdP(Ph_3)_2Cl_2$ as catalyst and CsF as base in $DMF/H_2O$ at 80° C.

The following preferred compounds of the present invention are prepared using the general procedure:

Cyclopropanecarboxylic acid [5-(2-dimethylamino-phenyl)-[1,2,4]triazolo[1,5-a]pyridin-2-yl]-amide;
Cyclopropanecarboxylic acid [5-(3-chloro-4-fluoro-phenyl)-[1,2,4]triazolo[1,5-a]pyridin-2-yl]-amide;
Cyclopropanecarboxylic acid (5-phenyl-[1,2,4]triazolo[1,5-a]pyridin-2-yl)-amide;
Cyclopropanecarboxylic acid [5-(3-trifluoromethoxy-phenyl)-[1,2,4]triazolo[1,5-a]pyridin-2-yl]-amide;
Cyclopropanecarboxylic acid [5-((E)-styryl)-[1,2,4]triazolo[1,5-a]pyridin-2-yl]-amide;
Cyclopropanecarboxylic acid [5-(3-chloro-phenyl)-[1,2,4]triazolo[1,5-a]pyridin-2-yl]-amide;
Cyclopropanecarboxylic acid (5-thiophen-3-yl-[1,2,4]triazolo[1,5-a]pyridin-2-yl)-amide;
Cyclopropanecarboxylic acid [5-(4-methoxy-phenyl)-[1,2,4]triazolo[1,5-a]pyridin-2-yl]-amide;
3-Cyclohexyl-N-[5-(4-hydroxy-3,5-dimethyl-phenyl)-[1,2,4]triazolo[1,5-a]pyridin-2-yl]-propionamide;
Cyclohexanecarboxylic acid (5-thiophen-3-yl-[1,2,4]triazolo[1,5-a]pyridin-2-yl)-amide;
Furan-2-carboxylic acid [5-(3-fluoro-phenyl)-[1,2,4]triazolo[1,5-a]pyridin-2-yl]-amide;
Furan-2-carboxylic acid [5-(4-hydroxy-3,5-dimethyl-phenyl)-[1,2,4]triazolo[1,5-a]pyridin-2-yl]-amide;
3-Methoxy-N-(5-thiophen-3-yl-[1,2,4]triazolo[1,5-a]pyridin-2-yl)-propionamide;
N-[6-(3-Hydroxymethyl-phenyl)-[1,2,4]triazolo[1,5-a]pyridin-2-yl]-3,3-dimethyl-butyramide;
Cyclopropanecarboxylic acid [6-(2-dimethylamino-phenyl)-[1,2,4]triazolo[1,5-a]pyridin-2-yl]-amide;
N-[6-(4-Hydroxy-phenyl)-[1,2,4]triazolo[1,5-a]pyridin-2-yl]-acetamide;
4-[2-(Cyclopropanecarbonyl-amino)-[1,2,4]triazolo[1,5-a]pyridin-5-yl]-N-(2-dimethylamino-ethyl)-benzamide;
4-[2-(Cyclopropanecarbonyl-amino)-[1,2,4]triazolo[1,5-a]pyridin-5-yl]-N-(2-hydroxy-ethyl)-benzamide;
Cyclopropanecarboxylic acid (5-furan-3-yl-[1,2,4]triazolo[1,5-a]pyridin-2-yl)-amide;
N-[5-(3-Amino-phenyl)-[1,2,4]triazolo[1,5-a]pyridin-2-yl]-3-pyridin-3-yl-propionamide;
Cyclopropanecarboxylic acid [5-(3-methanesulfonylamino-phenyl)-[1,2,4]triazolo[1,5-a]pyridin-2-yl]-amide; and
3-[2-(Cyclopropanecarbonyl-amino)-[1,2,4]triazolo[1,5-a]pyridin-6-yl]-N,N-dimethylbenzamide.

Example 2

Synthesis of Further Compounds According to the Present Invention

According to the general protocol the following compounds are prepared.

N-[6-(3-Methanesulfonylphenyl)-[1,2,4]triazolo[1,5-a]pyridin-2-yl]acetamide

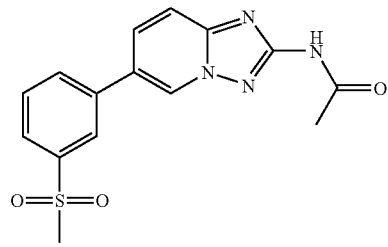 [SMILES: CC(=O)Nc1nc2ccc(-c3cccc(S(C)(=O)=O)c3)cn2n1]

$^1$H NMR ($d_6$-DMSO) δ 10.88 (br s, 1H), 9.45-9.46 (m, 1H), 8.31 (t, 1H), 8.20-8.15 (m, 1H), 8.09 (dd, 1H), 7.96-7.92 (m, 1H), 7.83-7.75 (m, 2H), 3.33 (s, 3H), 2.16 (br s, 3H); LCMS method (A), (MH+) 331, RT=5.99 min.

N-[6-(3-Acetylaminophenyl)-[1,2,4]triazolo[1,5-a]pyridin-2-yl]acetamide

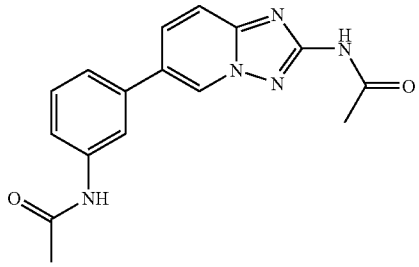 [SMILES: CC(=O)Nc1cccc(-c2ccc3nc(NC(C)=O)nn3c2)c1]

¹H NMR (d₆-DMSO) δ 10.84 (br s, 1H), 10.09 (s, 1H), 9.12-9.10 (m, 1H), 7.97-7.94 (m, 1H), 7.86 (dd, 1H), 7.77 (dd, 1H), 7.61-7.57 (m, 1H), 7.46-7.39 (m, 2H), 2.15 (br s, 3H), 2.08 (s, 3H); LCMS method (A), (MH+) 310, RT=5.90 min.

N-[6-(4-Methoxyphenyl)-[1,2,4]triazolo[1,5-a]pyridin-2-yl]acetamide

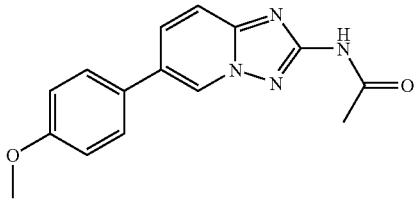 [SMILES: COc1ccc(-c2ccc3nc(NC(C)=O)nn3c2)cc1]

¹H NMR (d₆-DMSO) δ 10.81 (r s, 1H), 9.17-9.15 (m, 1H), 7.95 (dd, 1H), 7.76-7.70 (m, 3H), 7.09-7.04 (m, 2H), 3.81 (s, 3H), 2.15 (br s, 3H); LCMS method (A), (MH+) 283, RT=7.23 min.

N-[6-(1H-Indol-5-yl)-[1,2,4]triazolo[1,5-a]pyridin-2-yl]acetamide

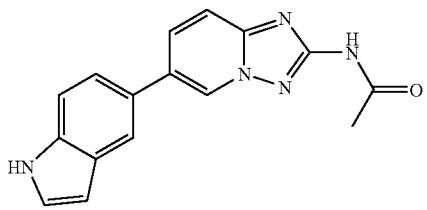 [SMILES: CC(=O)Nc1nc2ccc(-c3ccc4[nH]ccc4c3)cn2n1]

¹H NMR (d₆-DMSO) δ 11.31 (br s, 1H), 10.86 (br s, 1H), 9.18 (br s, 1H), 8.08 (d, 1H), 8.02 (br s, 1H), 7.81 (d, 1H), 7.58 (br s, 2H), 7.50 (br s, 1H), 6.59 (br s, 1H), 2.23 (br s, 3H); LCMS method (A), (MH+) 292, RT=6.92 min.

N-[6-(1H-Indol-4-yl)-[1,2,4]triazolo[1,5-a]pyridin-2-yl]acetamide

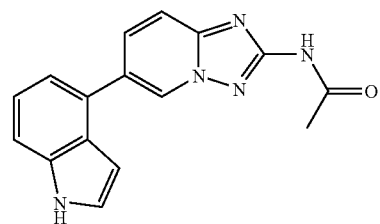 [SMILES: CC(=O)Nc1nc2ccc(-c3cccc4[nH]ccc34)cn2n1]

¹H NMR (d₆-DMSO) δ 11.55 (br s, 1H), 10.98 (br s, 1H), 9.17-9.15 (m, 1H), 8.11 (dd, 1H), 7.94 (dd, 1H), 7.65-7.62 (m, 2H), 7.40-7.33 (m, 2H), 6.76-7.73 (m, 1H), 2.31 (br s, 3H); (MH+) 292, RT=6.85 min.

N-[6-(2,3-Dihydrobenzofuran-5-yl)-[1,2,4]triazolo[1,5-a]pyridin-2-yl]acetamide

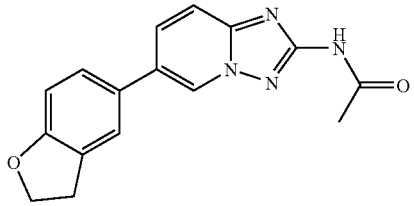 [SMILES: CC(=O)Nc1nc2ccc(-c3ccc4c(c3)CCO4)cn2n1]

¹H NMR (d₆-DMSO) δ 10.79 (br s, 1H), 9.10-9.08 (m, 1H), 7.91 (dd, 1H), 7.70 (d, 1H), 7.68-7.66 (m, 1H), 7.51 (dd, 1H), 6.87 (d, 1H), 4.59 (t, 2H), 3.25 (t, 2H), 2.14 (br s, 3H); LCMS method (A), (MH+) 295, RT=7.18 min.

N-[6-(2,4-Dimethoxyphenyl)-[1,2,4]triazolo[1,5-a]pyridin-2-yl]acetamide

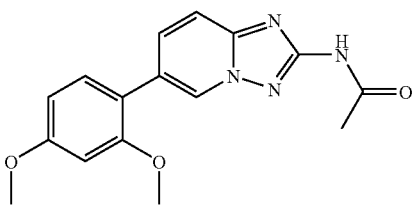 [SMILES: COc1ccc(-c2ccc3nc(NC(C)=O)nn3c2)c(OC)c1]

¹H NMR (d₆-DMSO) δ 10.77 (br s, 1H), 8.86-8.84 (m, 1H), 7.73 (dd, 1H), 7.66, (dd, 1H), 7.38 (d, 1H), 6.72 (d, 1H), 6.66 (dd, 1H), 3.82 (s, 3H), 3.82 (s, 3H), 2.14 (br s, 1H); LCMS method (A), (MH+) 313, RT=7.52 min.

N-(6-Pyridin-3-yl-[1,2,4]triazolo[1,5-a]pyridin-2-yl)acetamide

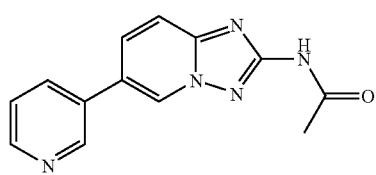 [SMILES: CC(=O)Nc1nc2ccc(-c3cccnc3)cn2n1]

LCMS method (A), (MH+) 254, RT=4.26 min.

N-[6-(5-Methoxypyridin-3-yl)-[1,2,4]triazolo[1,5-a]pyridin-2-yl]acetamide

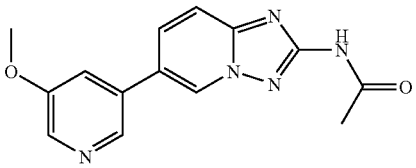 [SMILES: COc1cncc(-c2ccc3nc(NC(C)=O)nn3c2)c1]

¹H NMR (d₆-DMSO) δ 10.83 (br s, 1H), 9.28-9.26 (m, 1H), 8.61 (d, 1H), 8.15 (dd, 1H), 7.98 (dd, 1H), 7.76 (d, 1H), 6.66 (d, 1H), 3.91 (s, 3H), 2.15 (br s, 3H); LCMS method (A), (MH+) 284, RT=6.32 min.

N-[6-(4-Methoxy-3-trifluoromethylphenyl)-[1,2,4]triazolo[1,5-a]pyridin-2-yl]acetamide

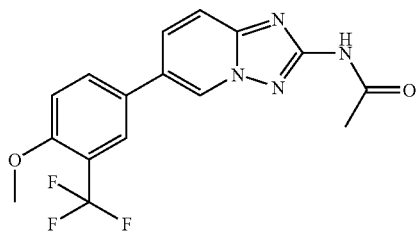 [SMILES: COc1ccc(-c2ccc3nc(NC(C)=O)nn3c2)cc1C(F)(F)F]

¹H NMR (d₆-DMSO) δ 10.83 (br s, 1H), 9.32-9.30 (m, 1H), 8.07 (dd, 1H), 8.04-7.99 (m, 2H), 7.74 (dd, 1H), 7.40 (d, 1H), 3.95 (s, 3H), 2.15 (br s, 3H); LCMS method (A), (MH+) 351, RT=8.38 min.

N-(6-Pyridin-4-yl-[1,2,4]triazolo[1,5-a]pyridin-2-yl)acetamide

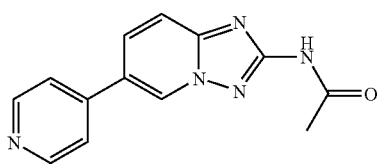 [SMILES: CC(=O)Nc1nc2ccc(-c3ccncc3)cn2n1]

¹H NMR (d₆-DMSO) δ 10.90 (br s, 1H), 9.51-9.49 (m, 1H), 8.69-8.66 (m, 2H), 8.11 (dd, 1H), 7.89-7.86 (m, 2H), 7.81 (dd, 1H), 2.16 (br s, 3H); LCMS method (A), (MH+) 254, RT=4.00 min.

N-[6-(6-Aminopyridin-3-yl)-[1,2,4]triazolo[1,5-a]pyridin-2-yl]acetamide

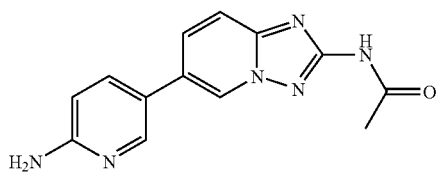 [SMILES: CC(=O)Nc1nc2ccc(-c3ccc(N)nc3)cn2n1]

¹H NMR (d₆-DMSO) δ 10.77 (br s, 1H), 9.10-9.08 (m, 1H), 8.34 (d, 1H), 7.90 (dd, 1H), 7.80 (dd, 1H), 7.69 (d, 1H), 6.53 (d, 1H), 6.19 (br s, 2H), 2.14 (br s, 3H); LCMS method (A), (MH+) 269, RT=4.14 min.

N-[6-(2,3-Dihydrobenzo[1,4]dioxin-6-yl)-[1,2,4]triazolo[1,5-a]pyridin-2-yl]acetamide

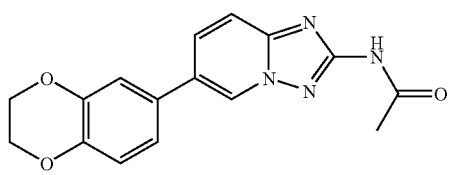 [SMILES: CC(=O)Nc1nc2ccc(-c3ccc4c(c3)OCCO4)cn2n1]

¹H NMR (d₆-DMSO) δ 10.80 (br s, 1H), 9.14-9.12 (m, 1H), 7.92 (dd, 1H), 7.69 (d, 1H), 7.32 (d, 1H), 7.26 (dd, 1H), 6.97 (d, 1H), 4.29 (s, 4H), 2.14 (br s, 3H); LCMS method (A), (MH+) 311, RT=7.10 min.

N-[6-(3,4-Dichloro-phenyl)-[1,2,4]triazolo[1,5-a]pyridin-2-yl]-acetamide

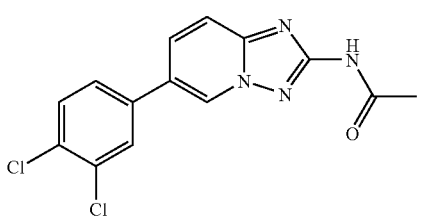 [SMILES: CC(=O)Nc1nc2ccc(-c3ccc(Cl)c(Cl)c3)cn2n1]

¹H NMR (d₆-DMSO) δ 10.90 (br, s, 1H), 9.37 (m, 1H), 8.14 (d, 1H), 8.04 (dd, 1H), 7.82 (dd, 1H), 7.77 (m, 1H), 7.75 (m, 1H), 2.15 (br, s, 3H); LCMS method (A), (MH+) 323/321 RT=8.73 min 5-(2-Acetylamino-[1,2,4]triazolo[1,5-a]pyridin-6-yl)-2-fluoro-N-(2-hydroxy-ethyl)-benzamide

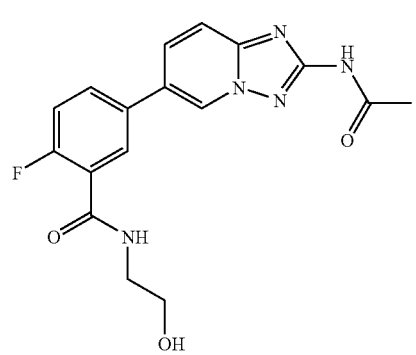 [SMILES: CC(=O)Nc1nc2ccc(-c3ccc(F)c(C(=O)NCCO)c3)cn2n1]

¹H NMR (d₆-DMSO) δ 10.85 (br, s, 1H), 9.29 (m, 1H), 8.43 (t, 1H), 7.98-8.03 (m, 2H), 7.93 (m, 1H), 7.77 (d, 1H), 7.42 (dd, 1H), 4.79 (t, 1H), 3.53 (q, 2H), 3.35 (m, 2H), 2.15 (br, s, 3H); LCMS method (A), (MH+) 358, (MH+22) 380 RT=5.07 min N-[6-(3-Dimethylsulfamoyl-phenyl)-[1,2,4]triazolo[1,5-a]pyridin-2-yl]-acetamide

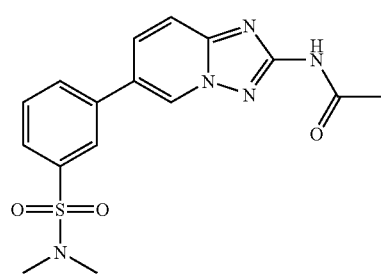 [SMILES: CC(=O)Nc1nc2ccc(-c3cccc(S(=O)(=O)N(C)C)c3)cn2n1]

¹H NMR (d₆-DMSO) δ 10.88 (br, s, 1H), 9.41 (m, 1H), 8.15 (t, 1H), 8.04-8.06 (m, 2H), 7.78 (dm, 3H), 2.67 (s, 6H), 2.15 (br, s, 3H); LCMS method (A), (MH+) 360, (MH+22) 382 RT=6.85 min

N-[6-(2,5-Dimethoxy-phenyl)-[1,2,4]triazolo[1,5-a]pyridin-2-yl]-acetamide

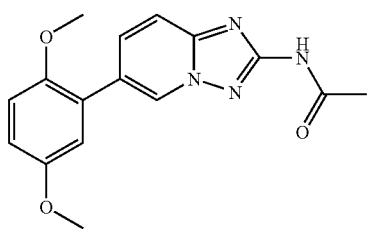 [SMILES: COc1ccc(OC)c(-c2ccc3nc(NC(C)=O)nn3c2)c1]

¹HNMR (d₆-DMSO) δ 10.80 (br, s, 1H), 8.95 (m, 1H), 7.83 (dd, 1H), 7.68 (dd, 1H), 7.10 (d, 1H), 7.05 (d, 1H), 6.97 (dd, 1H), 3.77 (s, 3H), 3.76 (s, 3H), 2.15 (br, s, 3H); LCMS method (A), (MH+) 313, (MH+22) 335 RT=7.42 min.

N-[6-(3,4,5-Trimethoxy-phenyl)-[1,2,4]triazolo[1,5-a]pyridin-2-yl]-acetamide

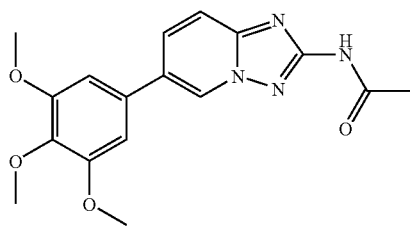 [SMILES: COc1cc(-c2ccc3nc(NC(C)=O)nn3c2)cc(OC)c1OC]

¹H NMR (d₆-DMSO) δ 10.82 (br, s, 1H), 9.33 (m, 1H), 8.05 (dd, 1H), 7.73 (d, 1H), 7.07 (s, 2H), 3.89 (s, 6H), 3.69 (s, 3H), 2.15 (br, s, 3H); LCMS method (A), (MH+) 343, (MH+22) 365 RT=6.82 min.

N-{6-[3-(2-Hydroxy-ethylsulfamoyl)-phenyl]-[1,2,4]triazolo[1,5-a]pyridin-2-yl}-acetamide

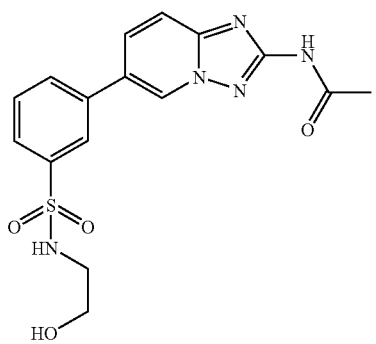 [SMILES: CC(=O)Nc1nc2ccc(-c3cccc(S(=O)(=O)NCCO)c3)cn2n1]

¹H NMR (d₆-DMSO) δ 10.88 (br, s, 1H), 9.34 (m, 1H), 8.17 (m, 1H), 8.07 (dm, 1H), 8.02 (dd, 1H), 7.82 (m, 2H), 7.72 (m, 1H), 7.66 (m, 1H), 4.74 (m, 1H), 3.40 (m, 2H), 2.85 (m, 2H), 2.16 (br, s, 3H); LCMS method (A), (MH+) 376, (MH+22) 398 RT=5.41 min.

N-[6-(3-Hydroxy-phenyl)-[1,2,4]triazolo[1,5-a]pyridin-2-yl]-acetamide

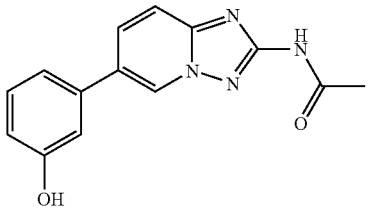 [SMILES: CC(=O)Nc1nc2ccc(-c3cccc(O)c3)cn2n1]

¹H NMR (d₆-DMSO) δ 9.08 (br, s, 1H), 7.88 (dm, 1H), 7.72 (dm, 1H), 7.25 (t, 1H), 7.12 (dm, 1H), 7.07 (m, 1H), 6.79 (dm, 1H), 2.15 (br, s, 3H); LCMS method (A), (MH+) 269, (MH+22) 291 RT=6.08 min.

N-[6-(2-Methoxy-phenyl)-[1,2,4]triazolo[1,5-a]pyridin-2-yl]-3-methyl-butyramide

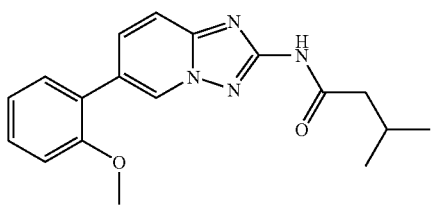 [SMILES: COc1ccccc1-c1ccc2nc(NC(=O)CC(C)C)nn2c1]

¹H NMR (d₆-DMSO) δ 10.74 (br s, 1H), 8.92 (s, 1H), 7.78 (dd, 1H), 7.68 (d, 1H), 7.40-7.47 (m, 2H), 7.17 (d, 1H), 7.06-7.16 (m, 1H), 3.82 (s, 3H), 2.30-2.33 (br s, 2H), 2.05-2.13 (m, 1H), 0.95 (s, 3H), 0.93 (s, 3H); LCMS method B, (MH+) 325, RT=2.72 min.

2-Cyclohexyl-N-[6-(2-methoxy-phenyl)-[1,2,4]triazolo[1,5-a]pyridin-2-yl]-acetamide

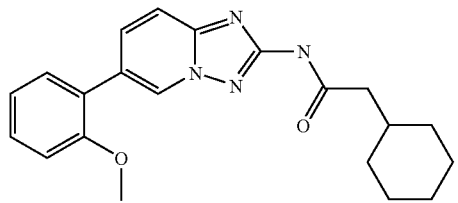 [SMILES: COc1ccccc1-c1ccc2nc(NC(=O)CC3CCCCC3)nn2c1]

¹H NMR (d₄-CD₃OD) δ 8.78 (br s, 1H), 7.83 (d, 1H), 7.61 (d, 1H), 7.38-7.42 (m, 2H), 7.12 (d, 1H), 7.05-7.08 (m, 1H), 3.85 (s, 3H), 2.29-2.35 (m, 2H), 1.55-1.94 (m, 6H), 0.89-1.37 (m, 5H); LCMS method B, (MH+) 365, RT=3.08 min.

2-Methoxy-N-[6-(2-methoxy-phenyl)-[1,2,4]triazolo[1,5-a]pyridin-2-yl]-acetamide

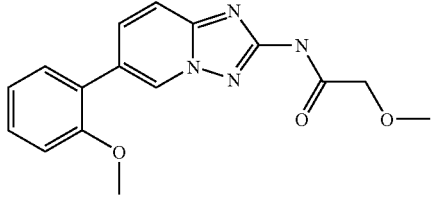 [SMILES: COCC(=O)Nc1nc2ccc(-c3ccccc3OC)cn2n1]

¹H NMR (d₆-DMSO) δ 10.68 (br s, 1H), 8.95 (s, 1H), 7.79 (dd, 1H), 7.71 (d, 1H), 7.40-7.47 (m, 2H), 7.17 (d, 1H), 7.06-7.16 (m, 1H), 4.15 (br s, 2H), 3.82 (s, 3H), 3.36 (s, 3H); LCMS method B, (MH+) 313, RT=2.33 min.

33

Furan-2-carboxylic acid [6-(2-methoxy-phenyl)-[1,2,4]triazolo[1,5-a]pyridin-2-yl]-amide

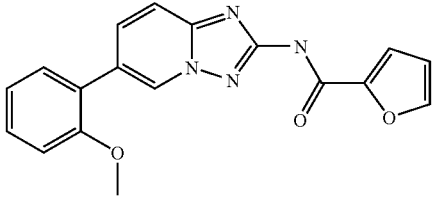 [SMILES: COc1ccccc1-c1ccc2nc(NC(=O)c3ccco3)nn2c1]

$^1$H NMR (d$_4$-CD$_3$OD) δ 8.76 (s, 1H), 7.79 (dd, 1H), 7.74 (d, 1H), 7.59 (d, 1H), 7.33-7.38 (m, 2H), 7.07 (d, 1H), 7.01 (t, 1H), 6.61 (dd, 1H), 3.80 (s, 3H); LCMS method B, (MH+) 335, RT=2.54 min.

Isoxazole-5-carboxylic acid [6-(2-methoxy-phenyl)-[1,2,4]triazolo[1,5-a]pyridin-2-yl]amide

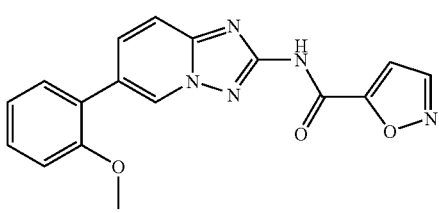 [SMILES: COc1ccccc1-c1ccc2nc(NC(=O)c3ccno3)nn2c1]

$^1$H NMR (d$_6$-DMSO) δ 9.02 (s, 1H), 8.85 (d, 1H), 7.85 (dd, 1H), 7.80 (dd, 1H), 7.41-7.49 (m, 3H), 7.05-7.20 (m, 2H), 3.83 (s, 3H); LCMS method B, (MH+) 336, RT=2.46 min.

N-[6-(2-Methoxy-phenyl)-[1,2,4]triazolo[1,5-a]pyridin-2-yl]-3-phenyl-propionamide

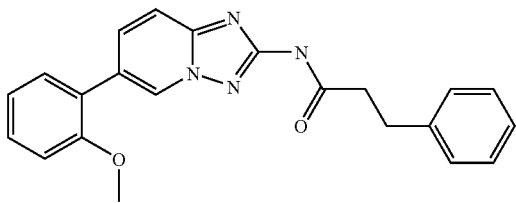 [SMILES: COc1ccccc1-c1ccc2nc(NC(=O)CCc3ccccc3)nn2c1]

$^1$H NMR (d$_6$-DMSO) δ 10.72 (br s, 1H), 8.80 (s, 1H), 7.66 (dd, 1H), 7.57 (dd, 1H), 7.33 (dd, 1H), 7.29 (dd, 1H), 6.92-7.18 (m, 7H), 3.70 (s, 3H), 2.78 (t, 2H), 2.62-2.68 (m, 2H); LCMS method B, (MH+) 373, RT=2.89 min.

N-[6-(6-Methoxy-pyridin-3-yl)-[1,2,4]triazolo[1,5-a]pyridin-2-yl]-acetamide

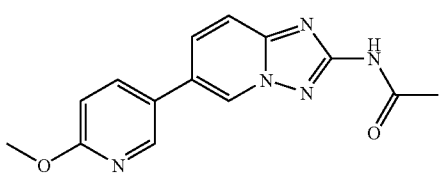 [SMILES: COc1ccc(-c2ccc3nc(NC(C)=O)nn3c2)cn1]

$^1$H NMR (d$_6$-DMSO) δ 10.38 (br s, 1H), 9.27 (s, 1H), 8.61 (d, 1H), 8.15 (dd, 1H), 7.98 (dd, 1H), 7.76 (d, 1H), 6.96 (d, 1H), 3.91 (s, 3H), 2.15 (br s, 3H); LCMS method B, (MH+) 284, RT=1.56 min.

34

N-[6-(5-Methanesulfonyl-pyridin-3-yl)-[1,2,4]triazolo[1,5-a]pyridin-2-yl]-acetamide

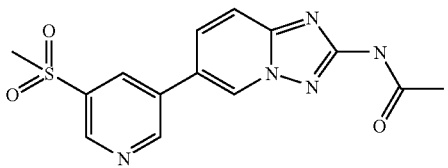 [SMILES: CC(=O)Nc1nc2ccc(-c3cncc(S(C)(=O)=O)c3)cn2n1]

$^1$H NMR (d$_6$-DMSO) δ 10.92 (br s, 1H), 9.57 (s, 1H), 9.36 (d, 1H), 9.07 (d, 1H), 8.71 (dd, 1H), 8.17 (dd, 1H), 7.85 (d, 1H), 3.43 (s, 3H), 2.17 (br s, 3H); LCMS method B, (MH+) 332, RT=1.05 min.

N-[6-(3-Methanesulfonyl-phenyl)-[1,2,4]triazolo[1,5-a]pyridin-2-yl]-2-methoxy-acetamide

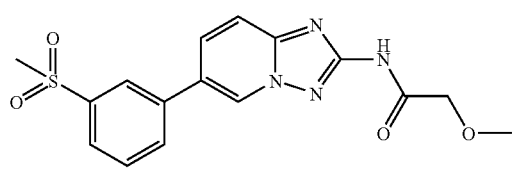 [SMILES: COCC(=O)Nc1nc2ccc(-c3cccc(S(C)(=O)=O)c3)cn2n1]

$^1$H NMR (d$_6$-DMSO) δ 10.78 (br s, 1H), 9.47 (s, 1H), 8.31 (t, 1H), 8.18 (dd, 1H), 8.11 (dd, 1H), 7.95 (dd, 1H), 7.77-7.84 (m, 2H), 4.16 (br s, 2H), 3.37 (s, 3H), 3.33 (br s, 1H); LCMS method B, (MH+) 361, RT=1.48 min.

N-[6-(3-Methanesulfonyl-phenyl)-[1,2,4]triazolo[1,5-a]pyridin-2-yl]-propionamide

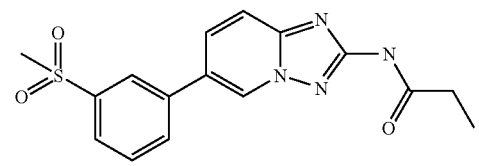 [SMILES: CCC(=O)Nc1nc2ccc(-c3cccc(S(C)(=O)=O)c3)cn2n1]

$^1$H NMR (d$_6$-DMSO) δ 10.83 (br s, 1H), 9.45 (s, 1H), 8.31 (s, 1H), 8.17 (d, 1H), 8.10 (dd, 1H), 7.95 (d, 1H), 7.77-7.82 (m, 2H), 3.34 (s, 3H), 2.45-2.50 (m, 2H), 1.09 (t, 3H); LCMS method B, (MH+) 345, RT=1.57 min.

Furan-2-carboxylic acid [6-(3-methanesulfonyl-phenyl)-[1,2,4]triazolo[1,5-a]pyridin-2-yl]-amide

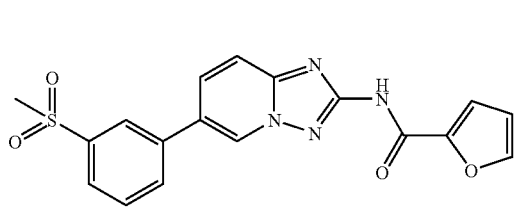 [SMILES: CS(=O)(=O)c1cccc(-c2ccc3nc(NC(=O)c4ccco4)nn3c2)c1]

$^1$H NMR (d$_6$-DMSO) δ 11.26 (br s, 1H), 9.51-9.52 (m, 1H), 8.33 (t, 1H), 8.18-8.20 (m, 1H), 8.13 (dd, 1H), 7.95-7.98 (m, 2H), 7.87 (d, 1H), 7.80 (t, 1H), 7.58 (d, 1H), 6.72 (dd, 1H), 3.34 (s, 3H); LCMS method B, (MH+) 383, RT=2.04 min.

35

N-[6-(3,4-Dimethoxy-phenyl)-[1,2,4]triazolo[1,5-a]pyridin-2-yl]-acetamide

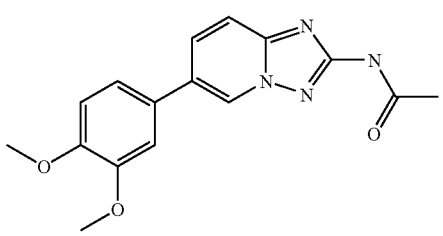 [SMILES: COc1ccc(-c2ccc3nc(NC(C)=O)nn3c2)cc1OC]

¹H NMR (d₆-DMSO) δ 10.80 (br s, 1H), 9.24 (s, 1H), 8.00 (dd, 1H), 7.72 (d, 1H), 7.31-7.38 (m, 2H), 7.06 (d, 1H), 3.87 (s, 3H), 3.80 (s, 3H), 2.14 (br s, 3H); LCMS method B, (MH+) 313, RT=1.77 min.

N-[6-(3-Methoxyphenyl)-[1,2,4]triazolo[1,5-a]pyridin-2-yl)acetamide

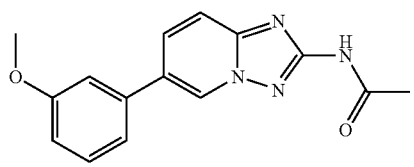 [SMILES: COc1cccc(-c2ccc3nc(NC(C)=O)nn3c2)c1]

¹H NMR (d₆-DMSO) δ 10.83 (br s, 1H), 9.27 (br s, 1H), 7.99 (dd, 1H), 7.73 (d, 1H), 7.41 (t, 1H), 7.37-7.35 (m, 2H), 6.99-6.97 (m, 1H), 3.85 (s, 3H), 2.15 (br s, 3H); LCMS method B, (MH+) 283, RT=2.27 min.

N-[6-(3-Sulfamoylphenyl)-[1,2,4]triazolo[1,5-a]pyridin-2-yl)acetamide

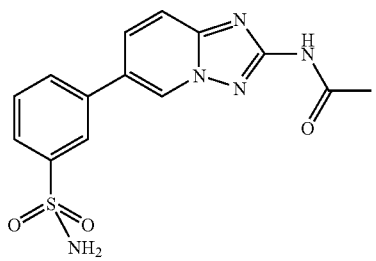 [SMILES: CC(=O)Nc1nc2ccc(-c3cccc(S(N)(=O)=O)c3)cn2n1]

¹H NMR (d₆-DMSO) δ 9.31 (br s, 1H), 8.21 (br s, 1H), 8.04 (br d, 1H), 7.99 (dd, 1H), 7.86-7.81 (m, 2H), 7.70 (t, 1H), 2.16 (br s, 3H); LCMS method B, (MH+) 296, RT=1.04 min.

3-[2-Acetylamino-[1,2,4]triazolo[1,5-a]pyridin-6-yl)benzamide

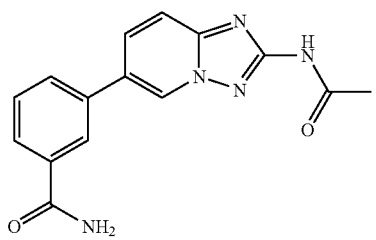 [SMILES: CC(=O)Nc1nc2ccc(-c3cccc(C(N)=O)c3)cn2n1]

¹H NMR (d₆-DMSO) δ 10.85 (br s, 1H), 9.34 (br s, 1H), 8.28-8.26 (m, 1H), 8.13 (br s, 1H), 8.07 (dd, 1H), 7.96 (br d, 1H), 7.89 (br d, 1H), 7.79 (d, 1H), 7.59 (t, 1H), 7.51 (br s, 1H), 2.16 (br s, 3H); LCMS method B, (MH+) 296, RT=1.04 min.

36

3-[2-Acetylamino-[1,2,4]triazolo[1,5-a]pyridin-6-yl)-N-methylbenzamide

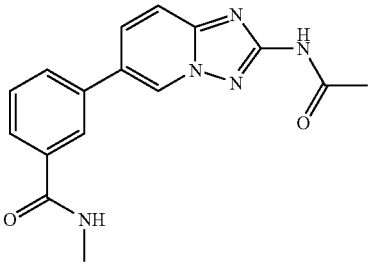 [SMILES: CNC(=O)c1cccc(-c2ccc3nc(NC(C)=O)nn3c2)c1]

¹H NMR (d₆-DMSO) δ 10.86 (br s, 1H), 9.32 (br s, 1H), 8.61-8.58 (m, 1H), 8.23-8.22 (m, 1H), 8.06 (dd, 1H), 7.95 (br d, 1H), 7.86 (br d, 1H), 7.79 (d, 1H), 7.60 (t, 1H), 2.83 (d, 3H), 2.16 (br s, 3H); LCMS method B, (MH+) 310, RT=1.45 min.

5-[2-Acetylamino-[1,2,4]triazolo[1,5-a]pyridin-6-yl)-N,N-dimethylbenzamide

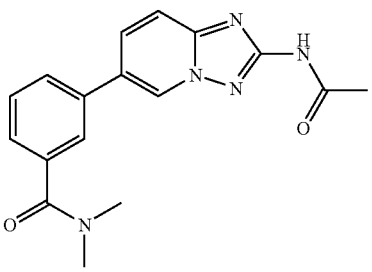 [SMILES: CC(=O)Nc1nc2ccc(-c3cccc(C(=O)N(C)C)c3)cn2n1]

¹H NMR (d₄-MeOH) δ 8.97 (br s, 1H), 7.98 (dd, 1H), 7.81 (d, 1H), 7.77-7.76 (m, 1H), 7.69 (d, 1H), 7.60 (t, 1H), 7.49-7.43 (m, 1H), 3.13 (s, 3H), 3.05 (s, 3H), 2.23 (br s, 3H); LCMS method B, (MH+) 324, RT=1.22 min.

4-[2-Acetylamino-[1,2,4]triazolo[1,5-a]pyridin-6-yl)benzamide

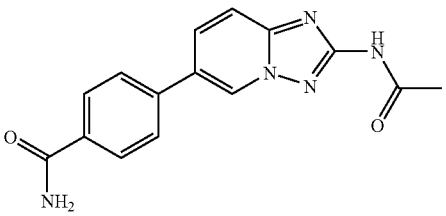 [SMILES: CC(=O)Nc1nc2ccc(-c3ccc(C(N)=O)cc3)cn2n1]

¹H NMR (d₆-DMSO) δ 10.86 (br s, 1H), 9.34 (br s, 1H), 8.08-8.04 (m, 2H), 8.09 (d, 2H), 7.90 (d, 2H), 7.77 (d, 1H), 7.48 (br s, 1H), 2.16 (br s, 3H); LCMS method B, (MH+) 296, RT=1.05 min.

N-[6-(3-Methylsulfamoylphenyl)-[1,2,4]triazolo[1,5-a]pyridin-2-yl]acetamide

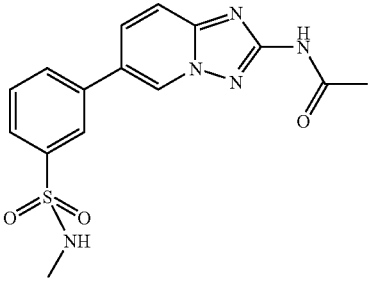 [SMILES: CNS(=O)(=O)c1cccc(-c2ccc3nc(NC(C)=O)nn3c2)c1]

¹H NMR (d₆-DMSO) δ 9.33 (br s, 1H), 8.11 (t, 1H), 8.07 (dt, 1H), 8.00 (dd, 1H), 7.81-7.79 (m, 2H), 7.73 (t, 1H), 2.46 (s, 3H), 2.16 (br s, 3H); LCMS method B, (MH+) 346, RT=1.45 min.

N-[6-(3-Isopropylsulfamoylphenyl)-[1,2,4]triazolo[1,5-a]pyridin-2-yl]acetamide

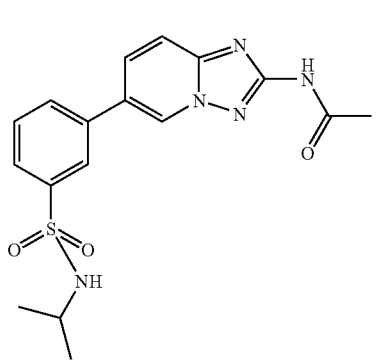 [SMILES: CC(=O)Nc1nc2ccc(-c3cccc(S(=O)(=O)NC(C)C)c3)cn2n1]

¹H NMR (d₆-DMSO) δ 10.88 (br s, 1H), 9.33 (br s, 1H), 8.18 (br s, 1H), 8.06 (d, 1H), 8.00 (dd, 1H), 7.85-7.80 (m, 2H), 7.72 (t, 1H), 7.62 (br s, 1H), 3.32 (septet, 1H), 2.16 (br s, 3H), 0.96 (d, 6H); LCMS method B, (MH+) 374, RT=2.18 min.

N-[6-(3-tertButylsulfamoylphenyl)-[1,2,4]triazolo[1,5-a]pyridin-2-yl]acetamide

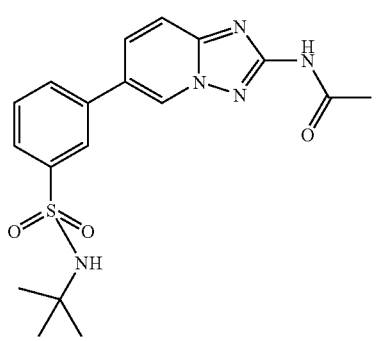 [SMILES: CC(=O)Nc1nc2ccc(-c3cccc(S(=O)(=O)NC(C)(C)C)c3)cn2n1]

¹H NMR (d₆-DMSO) δ 10.90 (br s, 1H), 9.32 (br s, 1H), 8.23 (t, 1H), 8.03 (d, 1H), 7.99 (dd, 1H), 7.85 (d, 1H), 7.81 (d, 1H), 7.70 (t, 1H), 7.57 (br s, 1H), 2.16 (br s, 3H), 1.12 (s, 9H); LCMS method B, (MH+) 388, RT=2.34 min.

N-[6-(3-Butylsulfamoylphenyl)-[1,2,4]triazolo[1,5-a]pyridin-2-yl]acetamide

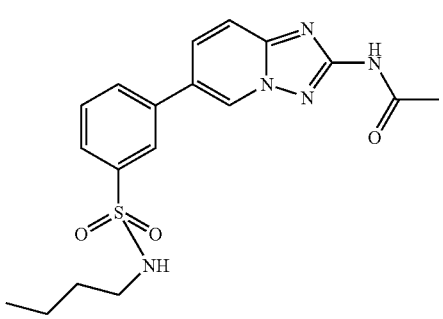 [SMILES: CCCCNS(=O)(=O)c1cccc(-c2ccc3nc(NC(C)=O)nn3c2)c1]

¹H NMR (d₆-DMSO) δ 9.33 (br s, 1H), 8.14 (t, 1H), 8.06 (d, 1H), 8.00 (dd, 1H), 7.82-7.80 (m, 2H), 7.72 (t, 1H), 2.77 (t, 2H), 2.16 (br s, 3H), 1.36 (quintet, 2H), 1.23 (sextet, 2H), 0.79 (t, 3H); LCMS method B, (MH+) 388, RT=2.38 min.

N-(6-Isoquinolin-6-yl)-[1,2,4]triazolo[1,5-a]pyridin-2-yl)acetamide

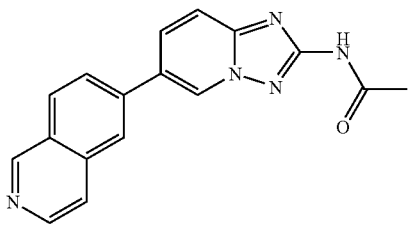 [SMILES: CC(=O)Nc1nc2ccc(-c3ccc4cnccc4c3)cn2n1]

¹H NMR (d₆-DMSO)N/A; LCMS method B, (MH+) 304, RT=4.78 min.

N-[6-(4-Hydroxy-3,5-dimethyl-phenyl)-[1,2,4]triazolo[1,5-a]pyridin-2-yl]-acetamide

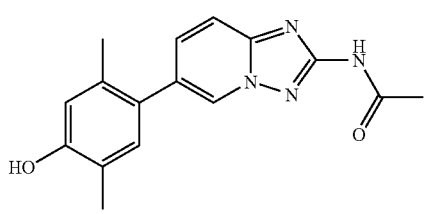 [SMILES: CC(=O)Nc1nc2ccc(-c3cc(C)c(O)cc3C)cn2n1]

N-[6-(4-Hydroxy-3-methoxy-phenyl)-[1,2,4]triazolo[1,5-a]pyridin-2-yl]-acetamide

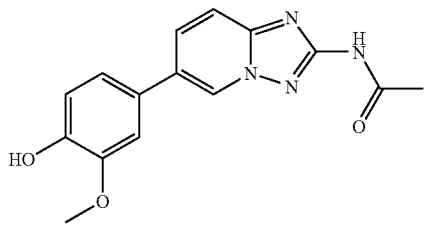 [SMILES: COc1cc(-c2ccc3nc(NC(C)=O)nn3c2)ccc1O]

¹H NMR (d₄-MeOH) δ 8.63 (s, 1H), 7.75 (dd, 1H), 7.46 (d, 1H), 7.05 (d, 1H), 6.96 (dd, 1H), 6.74 (d, 1H), 3.77 (s, 3H), 2.08 (s, 3H); LCMS method B, (MH+) 299, RT=1.26 min.

N-[6-(2-Methoxy-phenyl)-[1,2,4]triazolo[1,5-a]pyridin-2-yl]-acetamide

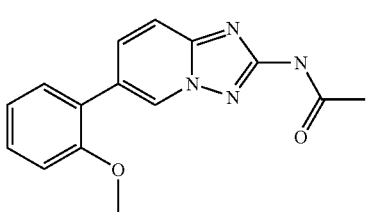 [SMILES: COc1ccccc1-c1ccc2nc(NC(C)=O)nn2c1]

39

Cyclopropanecarboxylic acid [6-(6-amino-pyridin-3-yl)-[1,2,4]triazolo[1,5-a]pyridin-2-yl]-amide

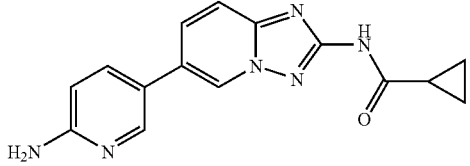 [SMILES: Nc1ccc(-c2ccc3nc(NC(=O)C4CC4)nn3c2)cn1]

N-[6-(4-Hydroxy-3-methoxy-phenyl)-[1,2,4]triazolo[1,5-a]pyridin-2-yl]-3,3-dimethyl-butyramide

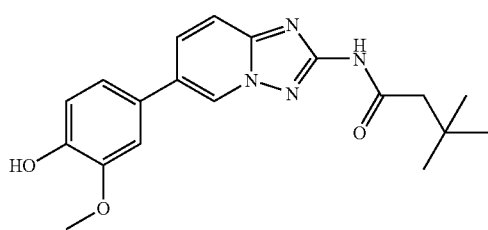 [SMILES: COc1cc(-c2ccc3nc(NC(=O)CC(C)(C)C)nn3c2)ccc1O]

N-[6-(3-Methanesulfonylamino-phenyl)-[1,2,4]triazolo[1,5-a]pyridin-2-yl]-acetamide

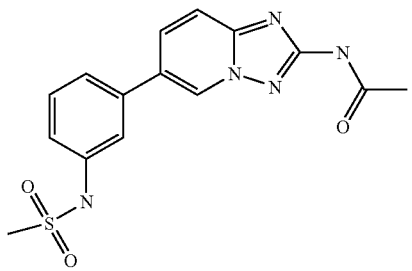 [SMILES: CC(=O)Nc1nc2ccc(-c3cccc(NS(C)(=O)=O)c3)cn2n1]

$^1$H NMR (d$_6$-DMSO) δ 10.83 (brs, 1H), 9.91 (s, 1H), 9.18 (s, 1H), 7.88 (dd, 1H), 7.77 (d, 1H), 7.23-7.79 (m, 4H), 2.96 (s, 3H), 2.15 (s, 3H); LCMS method B, (MH+) 346, RT=1.39 min.

N-[6-(4-Fluoro-phenyl)-[1,2,4]triazolo[1,5-a]pyridin-2-yl]-acetamide

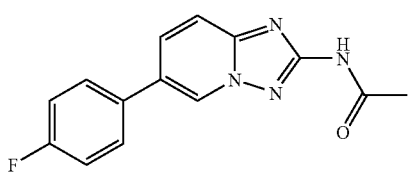 [SMILES: CC(=O)Nc1nc2ccc(-c3ccc(F)cc3)cn2n1]

$^1$H NMR (d$_6$-DMSO) δ 10.84 (brs, 1H), 9.23 (s, 1H), 7.96 (dd, 1H), 7.82-7.86 (m, 2H), 7.74 (d, 1H), 7.32-7.37 (m, 2H), 2.15 (brs, 3H); LCMS method B, (MH+) 271, RT=2.22 min.

40

N-[6-(3-Methanesulfonyl-phenyl)-[1,2,4]triazolo[1,5-a]pyridin-2-yl]-butyramide

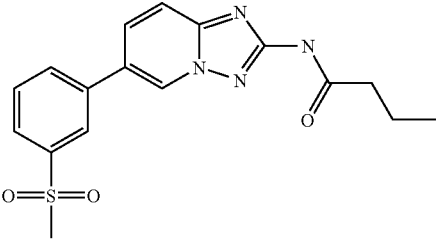 [SMILES: CCCC(=O)Nc1nc2ccc(-c3cccc(S(C)(=O)=O)c3)cn2n1]

$^1$H NMR (d$_6$-DMSO) δ 9.33 (s, 1H), 8.28 (d, 1H), 8.12 (d, 1H), 8.05 (dd, 1H), 7.96 (d, 1H), 7.74-7.79 (m, 2H), 3.28 (s, 3H), 2.42-2.44 (m, 2H), 1.61-1.67 (m, 2H), 0.93 (t, 3H); LCMS method B, (MH+) 359, RT=2.17 min.

N-(6-Pyrimidin-5-yl-[1,2,4]triazolo[1,5-a]pyridin-2-yl)-acetamide

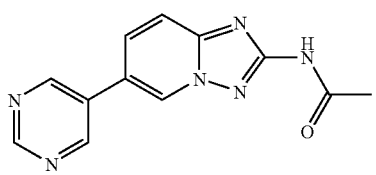 [SMILES: CC(=O)Nc1nc2ccc(-c3cncnc3)cn2n1]

$^1$H NMR (d$_6$-DMSO) δ 10.92 (brs, 1H), 9.49 (s, 1H), 9.27 (s, 2H), 9.23 (s, 1H), 8.11 (d, 1H), 7.83 (d, 1H), 2.16 (brs, 3H); LCMS method B, (MH+) 254, RT=1.03 min.

N-[6-(5-Methoxy-pyridin-3-yl)-[1,2,4]triazolo[1,5-a]pyridin-2-yl]-acetamide

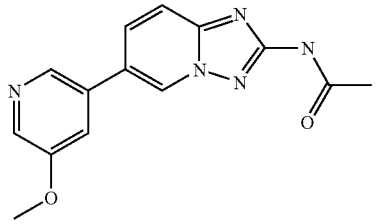 [SMILES: COc1cncc(-c2ccc3nc(NC(C)=O)nn3c2)c1]

$^1$H NMR (d$_6$-DMSO) δ 9.43 (s, 1H), 8.62 (d, 1H), 8.33 (d, 2H), 8.09 (dd, 1H), 7.78-7.82 (m, 2H), 3.93 (s, 3H), 2.16 (brs, 3H); LCMS method B, (MH+) 284, RT=1.18 min.

N-[6-(3-Fluoro-phenyl)-[1,2,4]triazolo[1,5-a]pyridin-2-yl]-acetamide

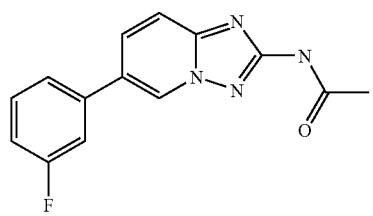 [SMILES: CC(=O)Nc1nc2ccc(-c3cccc(F)c3)cn2n1]

$^1$H NMR (d$_6$-DMSO) δ 10.87 (brs, 1H), 9.33 (s, 1H), 8.04 (dd, 1H), 7.66-7.78 (m, 3H), 7.52-7.58 (m, 1H), 7.24-7.28 (m, 1H), 2.16 (brs, 3H); LCMS method B, (MH+) 271, RT=2.30 min.

41

N-[6-(3,5-Difluoro-phenyl)-[1,2,4]triazolo[1,5-a]pyridin-2-yl]-acetamide

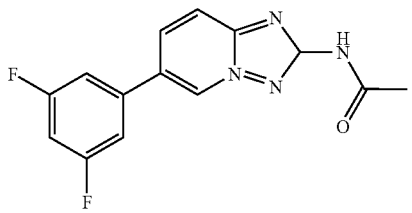

$^1$H NMR (d$_6$-DMSO) δ 10.88 (brs, 1H), 9.40 (d, 1H), 8.07 (dd, 1H), 7.77 (d, 1H), 7.63-7.68 (m, 2H), 7.28-7.33 (m, 1H), 2.16 (brs, 3H); LCMS method B, (MH+) 289, RT=2.37 min.

N-[6-(3-Trifluoromethyl-phenyl)-[1,2,4]triazolo[1,5-a]pyridin-2-yl]-acetamide

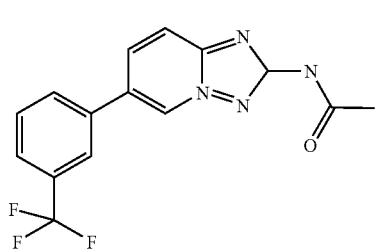

$^1$H NMR (d$_6$-DMSO) δ 10.88 (brs, 1H), 9.28 (s, 1H), 8.06-8.16 (m, 3H), 7.71-7.79 (m, 3H), 2.16 (brs, 3H); LCMS method B, (MH+) 321, RT=2.57 min.

N-{6-[5-(2-Hydroxy-ethylsulfamoyl)-pyridin-3-yl]-[1,2,4]triazolo[1,5-a]pyridin-2-yl}-acetamide

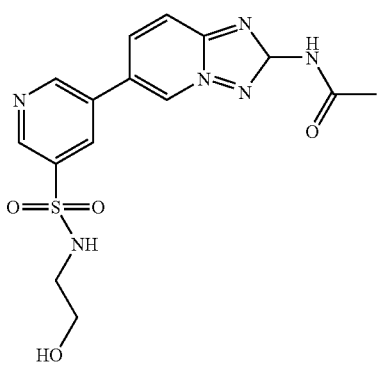

$^1$H NMR (d$_6$-DMSO) δ 9.14 (s, 1H), 9.09 (d, 1H), 8.92 (d, 1H), 8.47 (d, 1H), 7.96 (dd, 1H), 7.69 (d, 1H), 3.42-3.45 (m, 2H), 2.94-2.97 (m, 2H), 2.16 (brs, 3H); LCMS method B, (MH+) 377, RT=1.21 min.

42

N-(6-Thiophen-3-yl-[1,2,4]triazolo[1,5-a]pyridin-2-yl)-acetamide

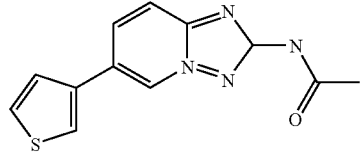

LCMS method B, (MH+) 259, RT=2.0 min.

N-(8-Methyl-6-pyridin-3-yl-[1,2,4]triazolo[1,5-a]pyridin-2-yl)-acetamide

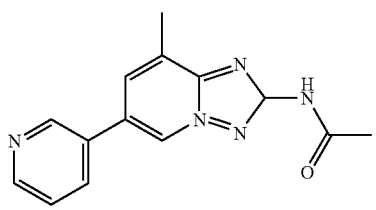

LCMS method B, (MH+) 268, RT=1.32 min.

N-[6-(3-Methanesulfonyl-phenyl)-8-methyl-[1,2,4]triazolo[1,5-a]pyridin-2-yl]-acetamide

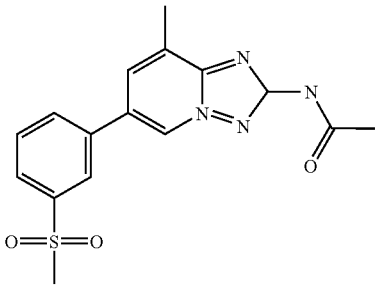

LCMS method B, (MH+) 345, RT=1.6 min.

N-[6-(3-Hydroxy-4-methoxy-phenyl)-[1,2,4]triazolo[1,5-a]pyridin-2-yl]-acetamide

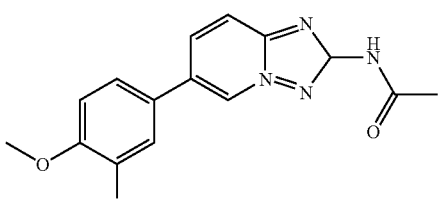

$^1$H NMR (d$_6$-DMSO) δ 10.80 (br, s, 1H), 9.20 (br, s, 1H), 9.04 (br, m, 1H), 7.87 (dd, 1H), 7.69 (dm, 1H), 7.15-7.19 (m,

1H), 7.03 (d, 1H), 3.82 (s, 3H), 2.14 (br, s, 3H); LCMS method (A), (MH+) 299, (MH+22) 321 RT=6.06 min.

N-[6-(5-Trifluoromethyl-pyridin-3-yl)-[1,2,4]triazolo[1,5-a]pyridin-2-yl]-acetamide

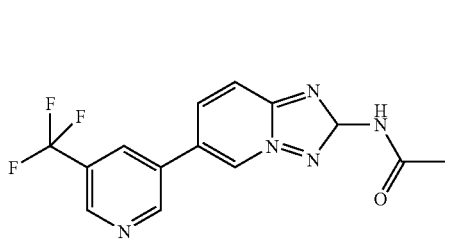

$^1$H NMR (d$_6$-DMSO) δ 10.90 (br, s, 1H), 9.54 (m, 1H), 9.34 (m, 1H), 9.02 (m, 1H), 8.66 (m, 1H), 8.17 (dd, 1H), 7.82 (d, 1H), 2.16 (br, s, 3H); LCMS method (B), (MH+) 322, (MH+22) 341 RT=2.04 min.

N-[6-(6-Trifluoromethyl-pyridin-3-yl)-[1,2,4]triazolo[1,5-a]pyridin-2-yl]-acetamide

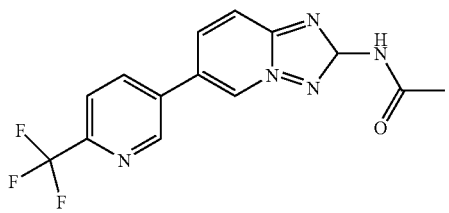

$^1$H NMR (d$_6$-DMSO) δ 10.91 (br, s, 1H), 9.52 (m, 1H), 9.23 (m, 1H), 8.52 (dm, 1H), 8.13 (dd, 1H), 8.05 (d, 1H), 7.84 (d, 1H), 2.16 (br, s, 3H); LCMS method (A), (MH+) 322, (MH+22) 341 RT=7.00 min.

N-[6-(4-Chloro-3-methanesulfonyl-phenyl)-[1,2,4]triazolo[1,5-a]pyridin-2-yl]-acetamide

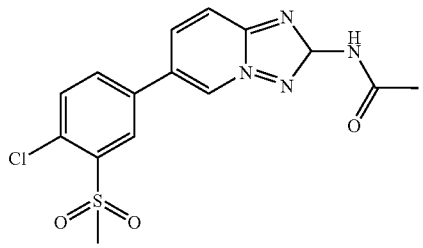

$^1$HNMR (d$_6$-DMSO) δ 10.89 (br, s, 1H), 9.39 (m, 1H), 8.30 (d, 1H), 8.15 (dd, 1H), 8.01 (dd, 1H), 7.89 (d, 1H), 7.80 (dm, 1H), 3.44 (s, 3H), 2.16 (br, s, 3H); LCMS method (A), (MH+) 365, (MH+22) 387 RT=6.47 min.

N-[6-(3-Aminophenyl)-[1,2,4]triazolo[1,5-a]pyridin-2-yl]acetamide

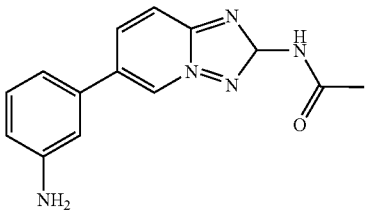

$^1$H NMR (d$_6$-DMSO) δ 10.81 (br s, 1H), 9.00 (dd, 1H), 7.84 (dd, 1H), 7.72 (dd, 1H), 7.13 (t, 1H), 6.89-6.86 (m, 2H), 6.60 (dq, 1H), 5.24 (s, 2H), 2.14 (br s, 3H); LCMS method (A), (MH+) 268, RT=4.85 min.

N-{6-[3-(Methanesulfonylmethylamino)phenyl]-[1,2,4]triazolo[1,5-a]pyridin-2-yl}acetamide

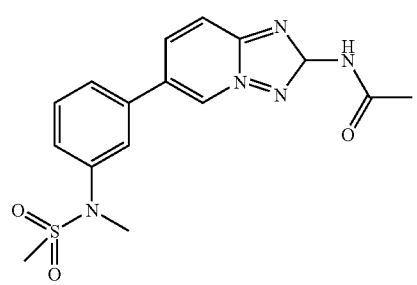

$^1$H NMR (d$_6$-DMSO) δ 10.85 (br s, 1H), 9.32 (br s, 1H), 8.01 (dd, 1H), 7.84 (t, 1H), 7.77 (dd, 1H), 7.75-7.73 (m, 1H), 7.53 (t, 1H), 7.43 (dq, 1H), 3.32 (s, 3H), 3.01 (s, 3H), 2.15 (br s, 3H); LCMS method (B), (MH+) 360, RT=2.02 min.

N-[6-(6-Aminopyridin-3-yl)-[1,2,4]triazolo[1,5-a]pyridin-2-yl]-N-benzamide

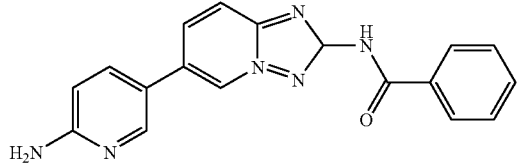

$^1$H NMR (d$_6$-DMSO) δ 8.90 (br s, 1H), 8.26 (br s, 1H), 8.03-8.01 (m, 2H), 7.92 (dd, 1H), 7.83 (dd, 1H), 7.72 (d, 1H), 7.65-7.61 (m, 1H), 7.57-7.53 (m, 2H), 6.71 (d, 1H); LCMS method (B), (MH+) 331, RT=1.67 min.

Cyclohexanecarboxylic acid [6-(3-methanesulfonylaminophenyl)-[1,2,4]triazolo[1,5-a]pyridin-2-yl]-amide

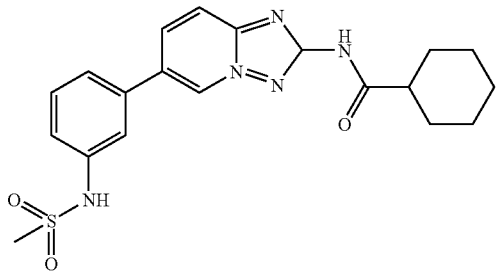

$^1$H NMR (d$_6$-DMSO) δ 10.73 (br s, 1H), 9.92 (br s, 1H), 9.16 (br s, 1H), 7.88 (dd, 1H), 7.76 (d, 1H), 7.52-7.45 (m, 3H), 7.26-7.23 (m, 1H), 3.08 (s, 3H), 1.83-1.63 (m, 5H), 1.44-1.14 (m, 6H); LCMS method (B), (MH+) 414, RT=2.49 min.

Cyclopropanecarboxylic acid [6-(3-methanesulfonylaminophenyl)-[1,2,4]triazolo[1,5-a]pyridin-2-yl]-amide

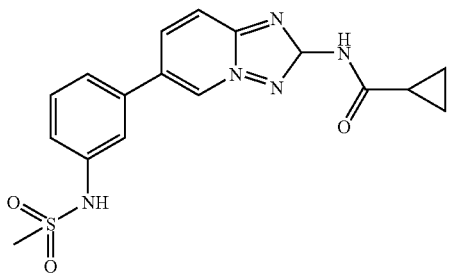

$^1$H NMR (d$_6$-DMSO) δ 11.11 (br s, 1H), 9.91 (br s, 1H), 9.16 (br s, 1H), 7.88 (dd, 1H), 7.77 (d, 1H), 7.52-7.45 (m, 3H), 7.26-7.23 (m, 1H), 3.08 (s, 3H), 2.07 (br s, 1H), 0.84-0.83 (m, 4H); LCMS method (B), (MH+) 372, RT=1.92 min.

Example 3

Preparation of Further Preferred Compounds of the Present Invention

Substituted 2-amino-6-bromo-[1,2,4]triazolo[1,5-a]pyridines are prepared in a method analogous to the above using appropriately substituted 2-amino-5-bromopyridines.

The preferred examples of the invention can also be synthesised by reaction of N-(6-bromo-[1,2,4]triazolo[1,5-a]pyridin-2-yl)acetamide with 4,4,4',4',5,5,5',5'-octamethyl-2,2'-bi(1,3,2-dioxaborolane) in DMF with a base such as sodium carbonate in the presence of Pd(PPh$_3$)$_2$Cl$_2$ as catalyst to afford N-(6-(4,4,5,5-tetramethyl-1,3,2-dioxaborolan-2-yl)-[1,2,4]triazolo[1,5-a]pyridin-2-yl)acetamide. The boronic ester can then be coupled with an aryl bromide under Suzuki reaction conditions using Pd(PPh$_3$)$_2$Cl$_2$ as catalyst and sodium carbonate as base in DME/H$_2$O/EtOH at 100° C. to afford the desired products. The aryl bromides were either selected from those commercially available or synthesised by elaboration of commercially available aryl bromides with other functional groups such as amines, carboxylic acids or sulfonyl chlorides.

3-bromo-N-(2-hydroxyethyl)benzamide is prepared by reaction of 3-bromobenzoic acid with 2-aminoethanol in DMF with HOBt and EDC.

5-bromo-N-(2-methoxyethyl)pyridine-3-sulfonamide is prepared by reaction of 5-bromopyridine-3-sulfonyl chloride with 2-methoxyethylamine in pyridine at 40° C. Other sulfonamides were prepared in analogous way using different amines.

N-(5-bromo-2-chloropyridin-3-yl)methanesulfonamide is prepared by reaction of 5-bromopyridin-3-amine with methanesulfonylchloride in pyridine at 60° C. Other sulfonamides were prepared using an analogous method with different sulfonyl chlorides either at room temperature or 60° C.

N-alkyl-6-aryl-[1,2,4]triazolo[1,5-a]pyridin-2-amines were prepared by treatment of 6-aryl-[1,2,4]triazolo[1,5-a]pyridin-2-amines with the appropriate alkylhalide in a suitable solvent such as DCM with an organic base such as $^i$Pr$_2$NEt.

N-methyl-6-aryl-[1,2,4]triazolo[1,5-a]pyridin-2-amines was prepared by reaction of 6-bromo-[1,2,4]triazolo[1,5-a]pyridin-2-amine with trimethylorthoformate followed by addition of sulfuric acid and heating to 100° C. The aryl ring was then introduced at C-6 using the Suzuki conditions described above.

1-substituted-3-(6-aryl-[1,2,4]triazolo[1,5-a]pyridin-2-yl) ureas were prepared from the corresponding 2-isocyanato-6-aryl-[1,2,4]triazolo[1,5-a]pyridine by treatment of crude reaction mixture with amines. The isocyanates were prepared from 6-bromo-[1,2,4]triazolo[1,5-a]pyridin-2-amines by treatment with triphosgene in anhydrous THF in the presence of pyridine. The aryl ring was then introduced at C-6 using the Suzuki conditions described above.

Methyl 6-(3,4-dimethoxyphenyl)-[1,2,4]triazolo[1,5-a]pyridin-2-ylcarbamate was prepared from 6-(3,4-dimethoxyphenyl)-[1,2,4]triazolo[1,5-a]pyridin-2-amine by treatment with methylchloroformate in THF in the presence of Et$_3$N.

The following compounds are prepared as outlined above and according to the general procedure of example 1.

N-[6-(5-(Methanesulfonylaminopyridin-3-yl)-[1,2,4]triazolo[1,5-a]pyridin-2-yl]-N-acetamide

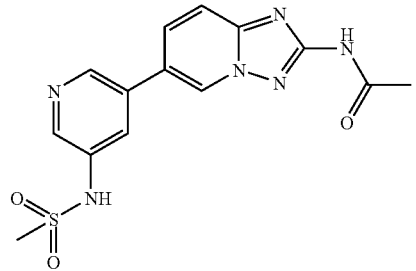 [SMILES: CC(=O)Nc1nc2ccc(-c3cncc(NS(C)(=O)=O)c3)cn2n1]

$^1$H NMR (d$_6$-DMSO) δ 10.88 (br s, 1H), 8.72 (s, 1H), 8.43 (s, 1H), 7.96 (dd, 1H), 7.88 (t, 1H), 7.80 (d, 1H), 3.16 (s, 3H), 2.16 (br s, 3H); LCMS method B, (MH+) 347, RT=0.99 min.

N-[6-(6-Chloro-5-(Methanesulfonylaminopyridin-3-yl)-[1,2,4]triazolo[1,5-a]pyridin-2-yl]-N-acetamide

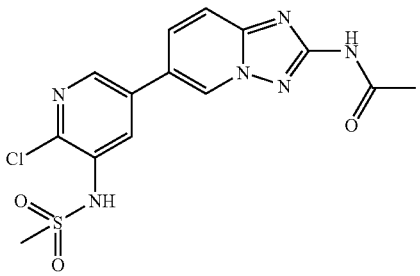 [SMILES: CC(=O)Nc1nc2ccc(-c3cnc(Cl)c(NS(C)(=O)=O)c3)cn2n1]

¹H NMR (d₆-DMSO) δ 10.88 (br s, 1H), 9.88 (s, 1H), 9.40 (s, 1H), 8.17-8.12 (m, 2H), 8.00 (d, 1H), 7.80 (d, 1H), 3.16 (s, 3H), 2.15 (br s, 3H); LCMS method C, (MH+) 381, RT=1.43 min.

N-[6-(5-Butylsulfamoylpyridin-3-yl)-[1,2,4]triazolo[1,5-a]pyridin-2-yl]acetamide

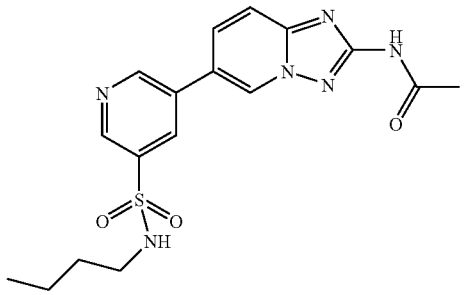 [SMILES: CCCCNS(=O)(=O)c1cncc(-c2ccc3nc(NC(C)=O)nn3c2)c1]

¹H NMR (d₆-DMSO) δ 10.83 (br s, 1H), 9.07 (dd, 1H), 8.01-8.00 (m, 2H), 7.83 (dd, 1H), 7.74 (dd, 1H), 7.45 (t, 1H), 2.76-2.72 (m, 2H), 2.15 (br s, 3H), 1.64-1.56 (m, 2H), 1.32 (sextet, 2H), 0.83 (t, 3H); LCMS method (C), (MH+) 389, RT=1.44 min.

3-(2-acetamido-[1,2,4]triazolo[1,5-a]pyridin-6-yl)benzoic acid

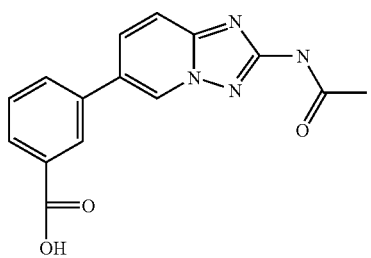 [SMILES: CC(=O)Nc1nc2ccc(-c3cccc(C(=O)O)c3)cn2n1]

¹H NMR (d₆-DMSO) δ 10.89 (brs, 1H), 9.14 (s, 1H), 8.19 (s, 1H), 7.95 (dd, 1H), 7.89 (d, 1H), 7.75 (d, 1H), 7.69 (d, 1H), 7.40 (t, 1H), 2.16 (brs, 3H); LCMS method B, (MH+) 297, RT=1.26 min.

N-(6-(4-(trifluoromethoxy)phenyl)-[1,2,4]triazolo[1,5-a]pyridin-2-yl)acetamide

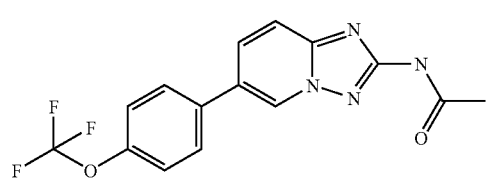 [SMILES: CC(=O)Nc1nc2ccc(-c3ccc(OC(F)(F)F)cc3)cn2n1]

¹H NMR (d₆-DMSO) δ 10.86 (brs, 1H), 9.30 (d, 1H), 8.00 (dd, 1H), 7.92-7.95 (m, 2H), 7.78 (d, 1H), 7.50-7.52 (m, 2H), 2.16 (brs, 3H); LCMS method B, (MH+) 337, RT=2.63 min.

N-(6-(3,4-difluorophenyl)-[1,2,4]triazolo[1,5-a]pyridin-2-yl)acetamide

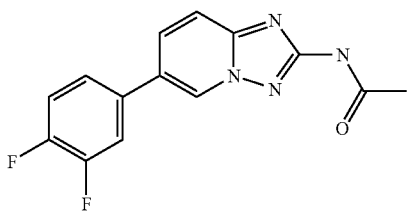 [SMILES: CC(=O)Nc1nc2ccc(-c3ccc(F)c(F)c3)cn2n1]

¹H NMR (d₆-DMSO) δ 10.86 (brs, 1H), 9.31 (s, 1H), 7.95-8.03 (m, 2H), 7.76 (dd, 1H), 7.68-7.71 (m, 1H), 7.54-7.62 (m, 1H), 2.16 (brs, 3H); LCMS method B, (MH+) 289, RT=2.28 min.

N-(6-(benzo[d][1,3]dioxol-5-yl)-[1,2,4]triazolo[1,5-a]pyridin-2-yl)acetamide

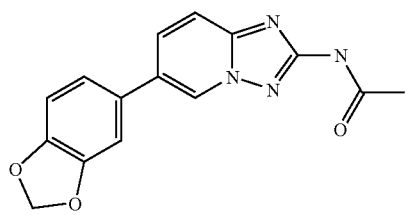 [SMILES: CC(=O)Nc1nc2ccc(-c3ccc4c(c3)OCO4)cn2n1]

¹H NMR (d₆-DMSO) δ 10.81 (brs, 1H), 9.15-9.16 (m, 1H), 7.94 (dd, 1H), 7.70-7.72 (m, 1H), 7.43 (d, 1H), 7.28 (dd, 1H), 7.04 (d, 1H), 6.09 (s, 2H), 2.15 (brs, 3H); LCMS method B, (MH+) 297, RT=2.12 min.

4-(2-acetamido-[1,2,4]triazolo[1,5-a]pyridin-6-yl)-N-(2-hydroxyethyl)benzamide

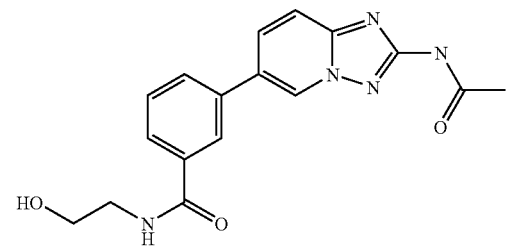 [SMILES: CC(=O)Nc1nc2ccc(-c3cccc(C(=O)NCCO)c3)cn2n1]

¹H NMR (d₄-MeOH) δ 8.99 (s, 1H), 8.19 (t, 1H), 8.03 (dd, 1H), 7.88-7.92 (m, 2H), 7.72 (d, 1H), 7.62 (t, 1H), 3.77 (t, 2H), 3.57 (t, 2H), 2.26 (brs, 3H); LCMS method B, (MH+) 340, RT=1.36 min.

N-(6-(4-fluoro-3-(trifluoromethyl)phenyl)-[1,2,4]triazolo[1,5-a]pyridin-2-yl)acetamide

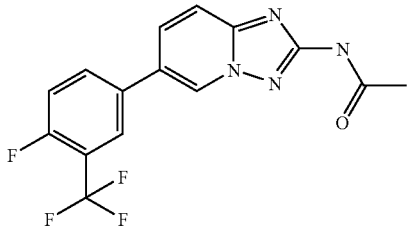 [SMILES: CC(=O)Nc1nc2ccc(-c3ccc(F)c(C(F)(F)F)c3)cn2n1]

¹H NMR (d₆-DMSO) δ 10.87 (brs, 1H), 9.40 (s, 1H), 8.16-8.20 (m, 2H), 8.06 (dd, 1H), 7.77 (d, 1H), 7.65-7.70 (m, 1H), 2.16 (brs, 3H); LCMS method B, (MH+) 339, RT=2.14 min.

N-(6-(3-fluoro-4-(trifluoromethyl)phenyl)-[1,2,4]triazolo[1,5-a]pyridin-2-yl)acetamide

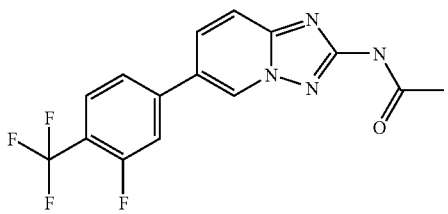 [SMILES: CC(=O)Nc1nc2ccc(-c3ccc(C(F)(F)F)c(F)c3)cn2n1]

¹H NMR (d₆-DMSO) δ 10.94 (brs, 1H), 9.47 (s, 1H), 8.05-8.11 (m, 2H), 7.89-7.91 (m, 2H), 7.81 (d, 1H), 2.16 (brs, 3H); LCMS method B, (MH+) 339, RT=2.18 min.

N-(6-(3,4-dimethoxy-2-methylphenyl)-[1,2,4]triazolo[1,5-a]pyridin-2-yl)acetamide

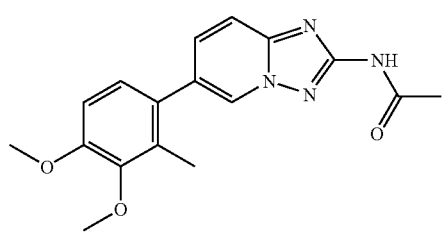 [SMILES: COc1ccc(-c2ccc3nc(NC(C)=O)nn3c2)c(C)c1OC]

¹H NMR (d₄-MeOH) δ 8.60 (brs, 1H), 7.62 (brs, 2H), 7.03 (d, 1H), 6.96 (d, 1H), 3.88 (s, 3H), 3.81 (s, 3H), 2.24 (brs, 3H), 2.19 (s, 3H); LCMS method B, (MH+) 327, RT=1.65 min.

N-(6-(3-isopropoxy-4-methoxyphenyl)-[1,2,4]triazolo[1,5-a]pyridin-2-yl)acetamide

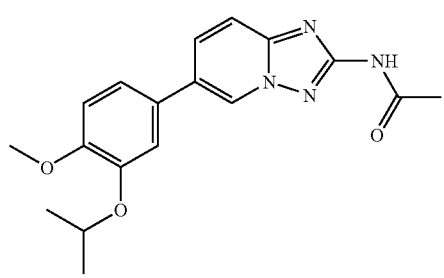 [SMILES: COc1ccc(-c2ccc3nc(NC(C)=O)nn3c2)cc1OC(C)C]

¹H NMR (d₆-DMSO) δ 10.80 (brs, 1H), 9.21 (s, 1H), 7.97 (dd, 1H), 7.71 (d, 1H), 7.38 (d, 1H), 7.32 (dd, 1H), 7.07 (d, 1H), 4.75-4.79 (m, 1H), 3.80 (s, 3H), 2.15 (brs, 3H), 1.30 (s, 3H), 1.28 (s, 2H); LCMS method (C), (MH+) 341, RT=2.25 min N-(6-(4-(trifluoromethoxy)-3-(trifluoromethyl)phenyl)-[1,2,4]triazolo[1,5-a]pyridin-2-yl)acetamide

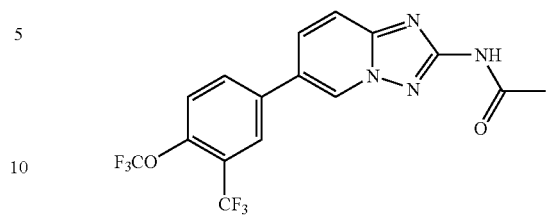

¹H NMR (d₆-DMSO) δ 10.88 (brs, 1H), 9.46 (s, 1H), 8.29 (s, 1H), 8.25 (d, 1H), 8.09 (dd, 1H), 7.80 (dd, 2H), 2.16 (brs, 3H); LCMS Method B, (MH+) 405, RT=2.69 min.

N-[6-(4-Chloro-2-trifluoromethyl-phenyl)-[1,2,4]triazolo[1,5-a]pyridin-2-yl]-acetamide

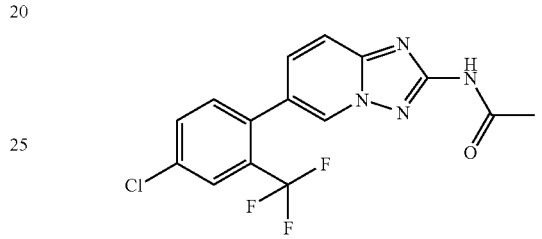

¹H NMR (d₆-DMSO) δ 10.86 (br, s, 1H), 8.95 (m, 1H), 7.99 (d, 1H), 7.89 (dd, 1H), 7.74 (d, 1H), 7.61 (d, 1H), 7.58 (d, 1H), 2.14 (br, s, 3H); LCMS method (A), (MH+) 355, (MH+22) 377, RT=8.74 min N-[6-(4-Fluoro-3-methoxy-phenyl)-[1,2,4]triazolo[1,5-a]pyridin-2-yl]-acetamide

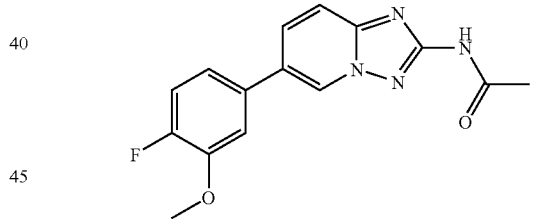

¹H NMR (d₆-DMSO) δ 10.83 (br, s, 1H), 9.32 (m, 1H), 8.01 (dd, 1H), 7.75 (d, 1H), 7.57 (dd, 1H), 7.32-7.35 (m, 2H), 3.96 (s, 3H), 2.15 (br, s, 3H); LCMS method (A), (MH+) 301, (MH+22) 323, RT=7.42 min N-[6-(3-Methoxy-pyridin-4-yl)-[1,2,4]triazolo[1,5-a]pyridin-2-yl]-acetamide

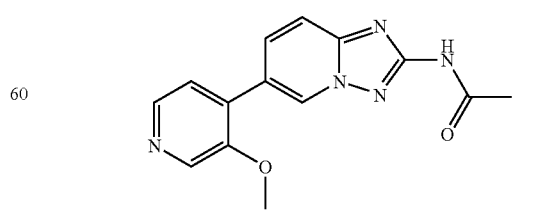

¹H NMR (d₆-DMSO) δ 9.05 (br, s, 1H), 8.49 (br, s, 1H), 8.31 (br, s, 1H), 7.86 (br, m, 1H), 7.67 (br, m, 1H), 7.51 (br, m,

1H), 3.94 (s, 3H), 2.15 (br, s, 3H); LCMS method (A), (MH+) 284, RT=4.36 min

N-(6-Isoquinolin-4-yl-[1,2,4]triazolo[1,5-a]pyridin-2-yl)-acetamide

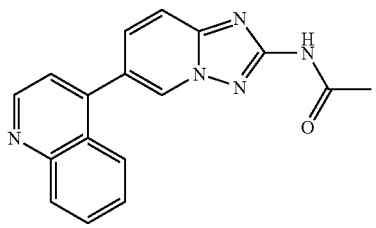

¹H NMR (d₆-DMSO) δ 10.88 (br, s, 1H), 9.43 (br, s, 1H), 9.13 (m, 1H), 8.57 (s, 1H), 8.27 (dm, 1H) 7.89 (dm, 1H), 7.81-7.86 (m, 3H), 7.76-7.80 (m, 1H), 2.17 (br, s, 3H); LCMS method (A), (MH+) 304, RT=5.26 min N-(6-Quinolin-3-yl-[1,2,4]triazolo[1,5-a]pyridin-2-yl)-acetamide

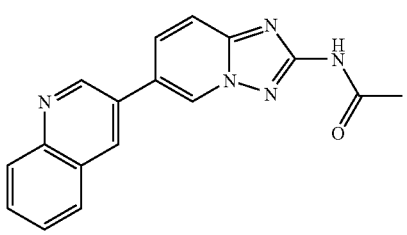 [SMILES: CC(=O)Nc1nc2ccc(-c3cnc4ccccc4c3)cn2n1]

¹H NMR (d₆-DMSO) δ 10.89 (br, s, 1H), 9.53 (m, 1H), 9.37 (d, 1H), 8.81 (d, 1H), 8.20 (dd, 1H) 8.07 (tm, 2H), 7.85 (dd, 1H), 7.81 (tm, 1H), 7.68 (tm, 1H), 2.17 (br, s, 3H); LCMS method (A), (MH+) 304, RT=6.19 min N-[6-(6-Fluoro-pyridin-3-yl)-[1,2,4]triazolo[1,5-a]pyridin-2-yl]-acetamide

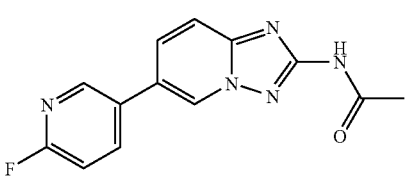 [SMILES: CC(=O)Nc1nc2ccc(-c3ccc(F)nc3)cn2n1]

¹H NMR (d₆-DMSO) δ 10.87 (br, s, 1H), 9.37 (m, 1H), 8.69 (br, s, 1H), 8.43 (br, t, 1H), 8.03 (d, 1H) 7.79 (d, 1H), 7.35 (dm, 1H), 2.15 (br, s, 3H); LCMS method (A), (MH+) 272, (MH+22), 294, RT=5.89 min N-{6-[3-(2-Methoxy-ethylsulfamoyl)-phenyl]-[1,2,4]triazolo[1,5-a]pyridin-2-yl}-acetamide

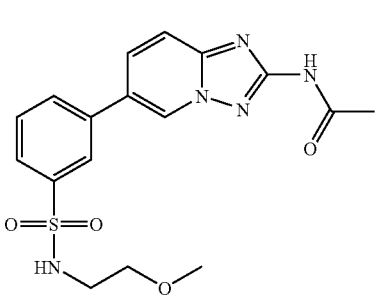 [SMILES: COCCNS(=O)(=O)c1cccc(-c2ccc3nc(NC(C)=O)nn3c2)c1]

¹H NMR (d₆-DMSO) δ 10.92 (br, s, 1H), 9.34 (s, 1H), 8.17 (s, 1H), 8.06 (d, 1H), 8.02 (d, 1H) 7.80-7.83 (m, 2H), 7.72 (t, 1H), 3.31 (t, 2H), 3.15 (s, 3H), 2.96 (t, 2H), 2.16 (br, s, 3H); LCMS method (A), (MH+) 390, RT=6.33 min N-{6-[3-(3-Hydroxy-propylsulfamoyl)-phenyl]-[1,2,4]triazolo[1,5-a]pyridin-2-yl}-acetamide

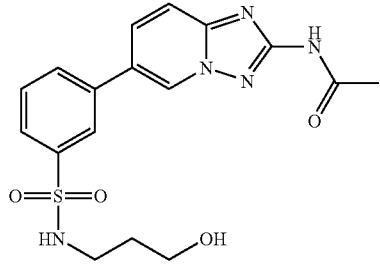 [SMILES: CC(=O)Nc1nc2ccc(-c3cccc(S(=O)(=O)NCCCO)c3)cn2n1]

¹H NMR (d₆-DMSO) δ 8.80 (br, s, 1H), 8.00 (br, m, 1H), 7.81 (d, 1H), 7.76 (dm, 1H) 7.71 (d, 1H), 7.55-7.59 (br, m, 2H), 3.56 (t, 2H), 3.43 (br, s, 3H), 2.97 (t, 2H), 2.19 (br, s, 3H), 1.61 (m, 2H); LCMS method (A), (MH+) 390, RT=3.13 min.

N-(6-{3-[Bis-(2-hydroxy-ethyl)-sulfamoyl]-phenyl}-[1,2,4]triazolo[1,5-a]pyridin-2-yl)-acetamide

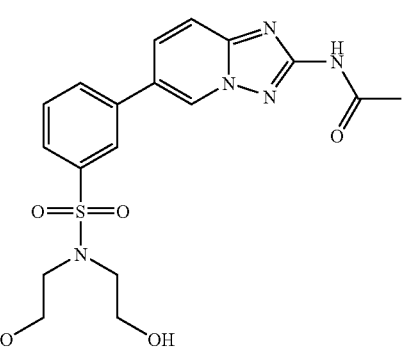

¹H NMR (d₆-DMSO) δ 8.77 (br, s, 1H), 7.95 (br, s, 1H), 7.71-7.76 (m, 3H), 7.54-7.59 (m, 2H) 3.69 (m, 4H), 3.20-3.26 (m, 6H), 2.15 (br, s, 3H); LCMS method (A), (MH+) 420, RT=3.16 min N-{6-[3-(3-Hydroxy-2,2-dimethyl-propylsulfamoyl)-phenyl]-[1,2,4]triazolo[1,5-a]pyridin-2-yl}-acetamide

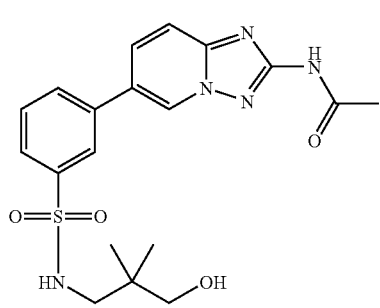 [SMILES: CC(=O)Nc1nc2ccc(-c3cccc(S(=O)(=O)NCC(C)(C)CO)c3)cn2n1]

¹H NMR (d₆-DMSO) δ 8.84 (br, s, 1H), 8.03 (m, 1H), 7.84 (dm, 1H), 7.78 (dd, 1H) 7.73 (dm, 1H), 7.58-7.62 (m, 2H), 3.30 (2H under H2O peak), 3.15 (br, s, 1H), 2.71 (s, 2H), 2.22 (br, s, 3H), 0.82 (s, 6H); LCMS method (A), (MH+) 418, RT=3.82 min N-[6-(5-Sulfamoyl-pyridin-3-yl)-[1,2,4]triazolo[1,5-a]pyridin-2-yl]-acetamide

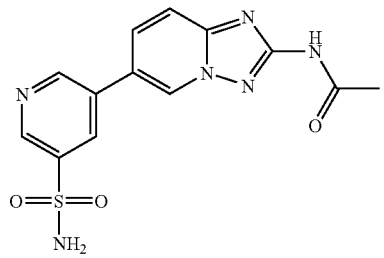 [SMILES: CC(=O)Nc1nc2ccc(-c3cncc(S(N)(=O)=O)c3)cn2n1]

$^1$H NMR (d$_6$-DMSO) δ 10.92 (br, s, 1H), 9.46 (m, 1H), 9.25 (m, 1H), 9.00 (m, 1H), 8.56 (m, 1H), 8.06 (d, 1H), 7.86 (d, 1H), 7.67 (br, s, 2H), 2.17 (br, s, 3H); LCMS method (A), (MH+) 333, RT=2.96 min N-{6-[5-(3,3,3-Trifluoro-propylsulfamoyl)-pyridin-3-yl]-[1,2,4]triazolo[1,5-a]pyridin-2-yl}-acetamide

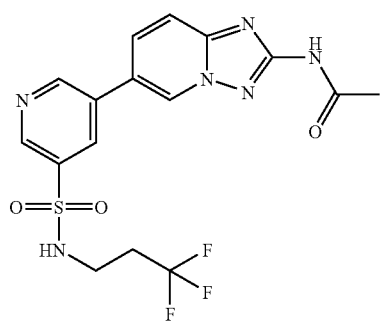 [SMILES: CC(=O)Nc1nc2ccc(-c3cncc(S(=O)(=O)NCCC(F)(F)F)c3)cn2n1]

$^1$H NMR (d$_6$-DMSO) δ 10.91 (br, s, 1H), 9.50 (m, 1H), 9.27 (d, 1H), 8.97 (d, 1H), 8.53 (t, 1H), 8.10 (dd, 1H), 7.84 (d, 1H), 3.11 (t, 2H), 2.46 (m, 2H), 2.16 (br, s, 3H); LCMS method (A), (MH+) 429, RT=4.04 min N-[6-(5-tert-Butylsulfamoyl-pyridin-3-yl)-[1,2,4]triazolo[1,5-a]pyridin-2-yl]-acetamide

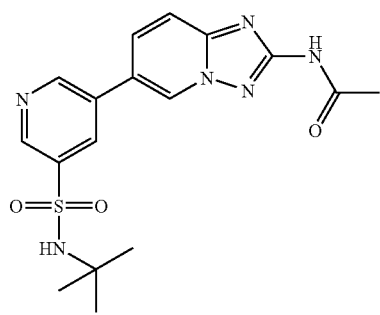 [SMILES: CC(=O)Nc1nc2ccc(-c3cncc(S(=O)(=O)NC(C)(C)C)c3)cn2n1]

$^1$H NMR (d$_6$-DMSO) δ 9.46 (m, 1H), 9.21 (d, 1H), 8.98 (d, 1H), 8.55 (t, 1H), 8.05 (dd, 1H), 7.83 (dd, 1H), 2.16 (br, s, 3H), 1.14 (s, 9H); LCMS method (A), (MH+) 389, RT=3.84 min N-{6-[5-(2-Ethyl-butylsulfamoyl)-pyridin-3-yl]-[1,2,4]triazolo[1,5-a]pyridin-2-yl}-acetamide

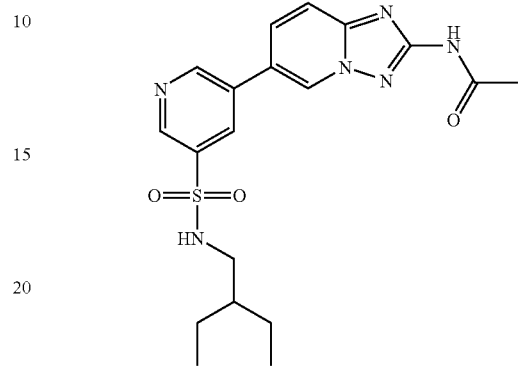

$^1$H NMR (d$_6$-DMSO) δ 9.46 (br, m, 1H), 9.21 (m, 1H), 8.93 (m, 1H), 8.48 (m, 1H), 8.06 (dd, 1H), 7.84 (dd, 1H), 2.74 (m, 2H), 2.15 (br, s, 3H), 1.24 (br, m, 4H), 0.78 (t, 6H); LCMS method (A), (MH+) 417, RT=4.97 min 2-[6-(3,4-Dimethoxy-phenyl)-[1,2,4]triazolo[1,5-a]pyridin-2-ylamino]-ethanol

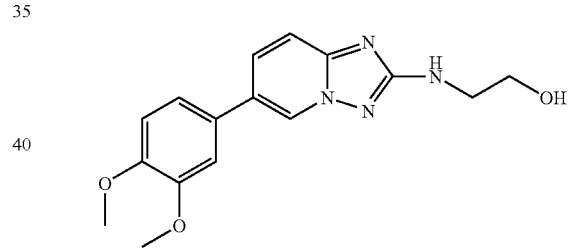

$^1$H NMR (CDCl$_3$) δ 8.47 (m, 1H), 7.61 (dm, 1H), 7.42 (dm, 1H), 7.09 (dm, 1H), 7.02 (m, 1H), 6.97 (dm, 1H), 4.94 (br, t, 2H), 3.95 (s, 3H), 3.94 (s, 3H), 3.90 (br, s, 3H), 3.61 (br, m, 2H), 3.25 (br, s, 1H); LCMS method (A), (MH+) 315, RT=3.51 min N-(5-methyl-6-(5-(methylsulfonyl)pyridin-3-yl)-[1,2,4]triazolo[1,5-a]pyridin-2-yl)acetamide

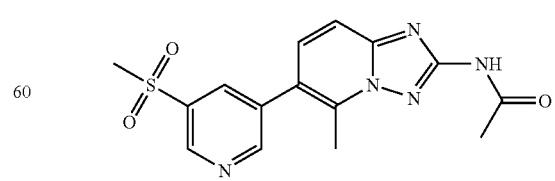

LCMS method (C), (MH+) 346, RT=1.66 min

55

N-(8-methyl-6-(5-(methylsulfonyl)pyridin-3-yl)-[1,2,4]triazolo[1,5-a]pyridin-2-yl)acetamide

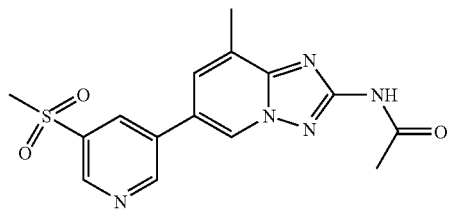 [SMILES: CC(=O)Nc1nc2c(C)cc(-c3cncc(S(C)(=O)=O)c3)cn2n1]

LCMS method (C), (MH+) 346, RT=1.75 min

N,N-dimethyl-6-(5-(methylsulfonyl)pyridin-3-yl)-[1,2,4]triazolo[1,5-a]pyridin-2-amine

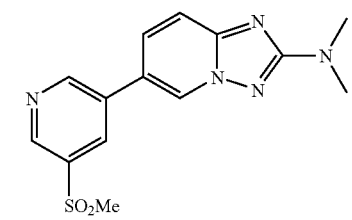 [SMILES: CN(C)c1nc2ccc(-c3cncc(S(C)(=O)=O)c3)cn2n1]

LCMS method (C), (MH+) 318, RT=1.93 min

N-(6-(3,4-dimethoxyphenyl)-5-methyl-[1,2,4]triazolo[1,5-a]pyridin-2-yl)acetamide

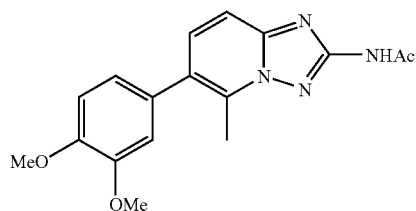 [SMILES: COc1ccc(-c2ccc3nc(NC(C)=O)nn3c2C)cc1OC]

LCMS method (C), (MH+) 327, RT=2.06 min

N-(6-(3,4-dimethoxyphenyl)-8-methyl-[1,2,4]triazolo[1,5-a]pyridin-2-yl)acetamide

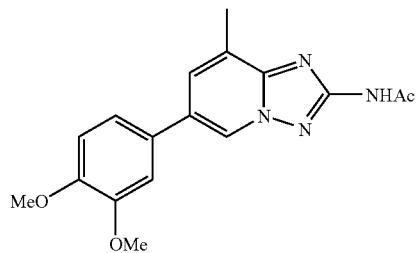 [SMILES: COc1ccc(-c2cc(C)c3nc(NC(C)=O)nn3c2)cc1OC]

LCMS method (C), (MH+) 327, RT=2.12 min

56

1-(2-hydroxyethyl)-3-(6-(5-(methylsulfonyl)pyridin-3-yl)-[1,2,4]triazolo[1,5-a]pyridin-2-yl)urea

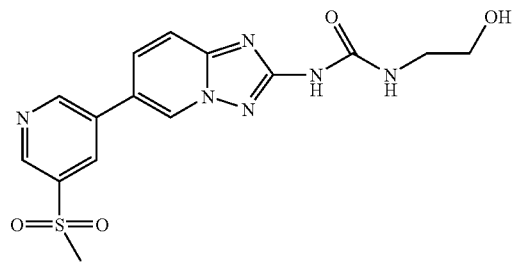 [SMILES: CS(=O)(=O)c1cncc(-c2ccc3nc(NC(=O)NCCO)nn3c2)c1]

LCMS method (C), (MH+) 377, (MNa+) 399, RT=1.69 min 1-(6-(3,4-dimethoxyphenyl)-[1,2,4]triazolo[1,5-a]pyridin-2-yl)-3-(2-hydroxyethyl)urea

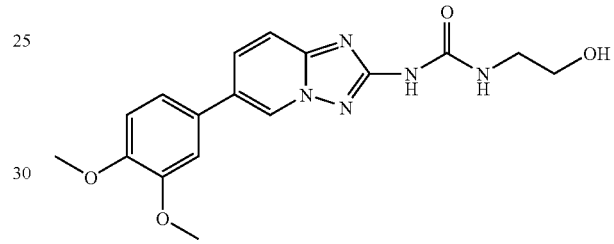

LCMS method (C), (MH+) 358, RT=2.04 min 1-(6-(3,4-dimethoxyphenyl)-[1,2,4]triazolo[1,5-a]pyridin-2-yl)-3-methylurea

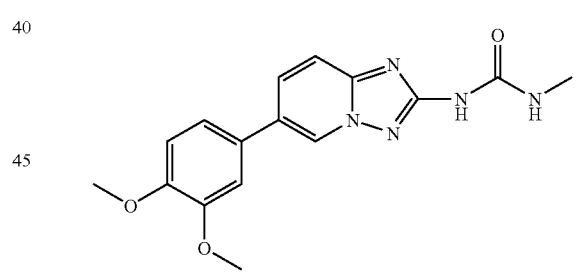

LCMS method (C), (MH+) 328, RT=2.20 min 6-(3,4-dimethoxyphenyl)-N-methyl-[1,2,4]triazolo[1,5-a]pyridin-2-amine

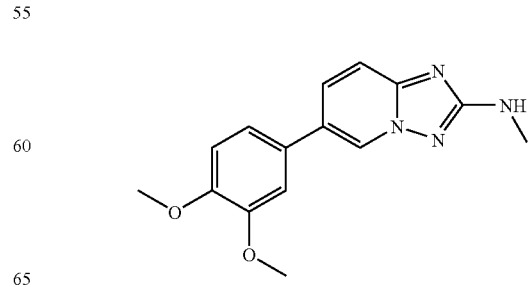

LCMS method (C), (MH+) 304, RT=1.71 min

Methyl 6-(3,4-dimethoxyphenyl)-[1,2,4]triazolo[1,5-a]pyridin-2-ylcarbamate

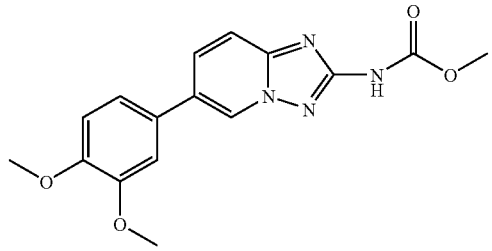

LCMS method (C), (MH+) 329, RT=2.10 min

N-(6-(4-hydroxyphenyl)-[1,2,4]triazolo[1,5-a]pyridin-2-yl)acetamide

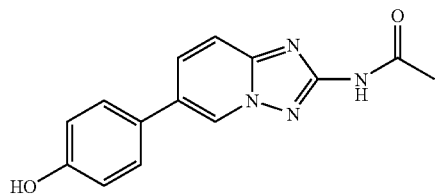 [SMILES: CC(=O)Nc1nc2ccc(-c3ccc(O)cc3)cn2n1]

Example 4

Determination of the Effect of the Compounds According to the Invention on Itk

Kinase activity and compound inhibition of Itk (recombinant human Itk, GST-tagged; catalogue number V4193, Invitrogen, Carlsbad, Calif., USA) is determined using the Z'-LYTE Kinase assay kit-Tyr 1 peptide (catalogue number PV3190) according to the manufacturer's instructions (Invitrogen, Carlsbad, Calif., USA).

The Z'-LYTE biochemical assay uses a fluorescence resonance energy transfer (FRET)-based coupled enzyme format that is based on the differential sensitivity of phosphorylated and non-phosphorylated peptides to proteolytic cleaveage. The peptide substrate is labeled with two fluorophores constituting a FRET pair. In the primary reaction, the kinase transfers the gamma-phosphate of ATP to a tyrosine residue in the synthetic peptide substrate. In the secondary development reaction, a site-specific protease cleaves non-phosphorylated peptides. Cleavage disrupts FRET between the donor and acceptor fluorophores on the peptide, whereas uncleaved phosphorylated peptides maintain FRET.

Calculation of the ratio of donor emission to acceptor emission (after excitation of the donor at 400 nm) quantifies the reaction progress (Rodems et al., 2002, Assay Drug Dev. Technol. 1, 9-19).

Stock solutions of compounds (1.6 mM in DMSO) are diluted in 2% DMSO so that final concentrations of 8 µM and 0.8 µM are achieved in the assay.

In general, compounds of the invention as described in example 1 are effective for the inhibition of Itk.

Example 5

Determination of the Effect of the Compounds according to the Invention on PI3K

The compounds of the present invention as described in example 2 and 3 are tested in the PI3K kinobeads assay as described (EP06016205.4). Briefly, test compounds (at various concentrations) and the affinity matrix with the immobilized phenylthiazole ligand 1 are added to cell lysate aliquots and allowed to bind to the proteins in the lysate sample. After the incubation time the beads with captured proteins are separated from the lysate. Bound proteins are then eluted and the presence of PI3K gamma is detected and quantified using a specific antibody in a dot blot procedure and the Odyssey infrared detection system.

In general, compounds of the invention as described in examples 2 and 3 are effective for the inhibition of PI3K gamma, with an $IC_{50}$ of <100 µM.

The invention claimed is:
1. A compound of formula (I)

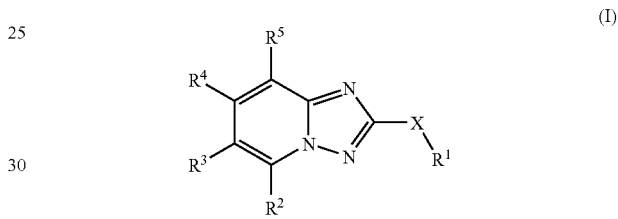

or a pharmaceutically acceptable salt, or prodrug thereof, wherein
X is O; S or $NR^6$;
$R^1$ is $T^1$; $C_{1-6}$ alkyl; $C(O)OR^7$; $C(O)R^7$; $C(O)N(R^7R^{7a})$; $S(O)_2N(R^7R^{7a})$; $S(O)N(R^7R^{7a})$; $S(O)_2R^7$; or $S(O)R^7$, wherein $C_{1-6}$ alkyl is optionally substituted with one or more $R^8$;
One of $R^2$, $R^3$ is $T^2$ and the other is $R^{5a}$;
$R^4$, $R^5$, are independently selected from the group consisting of H and $CH_3$;
$R^{5a}$ is H or $C_{1-6}$ alkyl;
$R^6$, $R^{7a}$ are independently selected from the group consisting of H; and $C_{1-6}$ alkyl, wherein $C_{1-6}$ alkyl is optionally substituted with one or more halogen, which are the same or different;
$R^7$ is $T^1$; or $C_{1-6}$ alkyl, wherein $C_{1-6}$ alkyl is optionally substituted with one or more $R^8$;
$R^8$ is $T^1$; $C_{1-6}$ alkyl; halogen; CN; $C(O)OR^{11}$; $OR^{11}$; $C(O)R^{11}$; $C(O)N(R^{11}R^{11a})$; $S(O)_2N(R^{11}R^{11a})$; $S(O)N(R^{11}R^{11a})$; $S(O)_2R^{11}$; $S(O)R^{11}$; $N(R^{11})S(O)_2N(R^{11a}R^{11b})$; $SR^{11}$; $N(R^{11}R^{11a})$; $OC(O)R^{11}$; $N(R^{11})C(O)R^{11a}$; $N(R^{11})S(O)_2R^{11a}$; $N(R^{11})S(O)R^{11a}$; $N(R^{11})C(O)N(R^{11a}R^{11b})$; $N(R^{11})C(O)OR^{11a}$; or $OC(O)N(R^{11}R^{11a})$, wherein $C_{1-6}$ alkyl is optionally substituted with one or more halogen which are the same or different;
$T^1$ is $C_{3-7}$ cycloalkyl; heterocyclyl; or phenyl, wherein $T^1$ is optionally substituted with one or more $R^{10}$;
$R^{11}$, $R^{11a}$, $R^{11b}$, are independently selected from the group consisting of H; and $C_{1-6}$ alkyl, wherein $C_{1-6}$ alkyl is optionally substituted with one or more halogen, which are the same or different;
$R^{10}$ is $C_{1-6}$ alkyl; halogen; CN; $C(O)OR^{12}$; $OR^{12}$; oxo (=O), where the ring is at least partially saturated; C(O)

$R^{12}$; $C(O)N(R^{12}R^{12a})$; $S(O)_2N(R^{12}R^{12a})$; $S(O)N(R^{12}R^{12a})$; $S(O)_2R^{12}$; $S(O)R^{12}$; $N(R^{12})S(O)_2N(R^{12a}R^{12b})$; $SR^{12}$; $N(R^{12}R^{12a})$; $OC(O)R^{12}$; $N(R^{12})C(O)R^{12a}$; $N(R^{12})S(O)_2R^{12a}$; $N(R^{12})S(O)R^{12a}$; $N(R^{12})C(O)N(R^{12a}R^{12b})$; $R^{12}C(O)OR^{12a}$; or $OC(O)N(R^{12}R^{12a})$, wherein $C_{1-6}$ alkyl is optionally substituted with one or more halogen which are the same or different;

$R^{12}$, $R^{12a}$, $R^{12b}$ are independently selected from the group consisting of H; and $C_{1-6}$ alkyl, wherein $C_{1-6}$ alkyl is optionally substituted with one or more halogen, which are the same or different;

$T^2$ is $T^3$; $C(R^{13}R^{13a})$-$T^3$; $C(R^{13}R^{13a})$—$C(R^{13b}R^{13c})$-$T^3$; cis $C(R^{13})$=$C(R^{13b})$-$T^3$; trans $C(R^{13})$=$C(R^{13b})$-$T^3$; or C≡C-$T^3$;

$R^{13}$, $R^{13a}$, $R^{13b}$, $R^{13c}$ are independently selected from the group consisting of H; and F;

$T^3$ is phenyl; pyrrolyl; furyl; thienyl; oxazolyl; thiazolyl; pyrimidinyl; indolyl; indolinyl; indazolyl; quinolinyl; isoquinolinyl, benzodioxolyl, dihydrobenzofuryl; dihydrobenzoxazinyl; or benzodioxanyl optionally substituted with one or more $R^{14}$;

$R^{14}$ is $C_{1-6}$ alkyl; halogen; CN; $C(O)OR^{15}$; $OR^{15}$; oxo (=O), where the ring is at least partially saturated; $C(O)R^{15}$; $C(O)N(R^{15}R^{15a})$; $S(O)_2N(R^{15}R^{15a})$; $S(O)N(R^{15}R^{15a})$; $S(O)_2R^{15}$; $S(O)R^{15}$; $N(R^{15})S(O)_2N(R^{15a}R^{15b})$; $SR^{15}$; $N(R^{15}R^{15a})$; $OC(O)R^{15}$; $N(R^{15})C(O)R^{15a}$; $N(R^{15})S(O)_2R^{15a}$; $N(R^{15})S(O)R^{15a}$; $N(R^{15})C(O)N(R^{15a}R^{15b})$, $N(R^{15})C(O)OR^{15a}$; or $OC(O)N(R^{15}R^{15a})$, wherein $C_{1-6}$ alkyl is optionally substituted with one or more $R^{16}$;

$R^{15}$, $R^{15a}$, $R^{15b}$ are independently selected from the group consisting of H; and $C_{1-6}$ alkyl, wherein $C_{1-6}$ alkyl is optionally substituted with $R^{17}$;

$R^{16}$, $R^{17}$ are independently selected from the group consisting of halogen; CN; $C(O)OR^{18}$; $OR^{18}$; $C(O)R^{18}$; $C(O)N(R^{18}R^{18a})$; $S(O)_2N(R^{18}R^{18a})$; $S(O)N(R^{18}R^{18a})$; $S(O)_2R^{18}$; $S(O)R^{18}$; $N(R^{18})S(O)_2N(R^{18a}R^{18b})$; $SR^{18}$; $N(R^{18}R^{18a})$; $OC(O)R^{18}$; $N(R^{18})C(O)R^{18a}$; $N(R^{18})S(O)_2R^{18a}$; $N(R^{18})S(O)R^{18a}$; $N(R^{18})C(O)N(R^{18a}R^{18b})$; $N(R^{18})C(O)OR^{18a}$; $OC(O)N(R^{18}R^{18a})$; and $C_{1-6}$ alkyl, wherein $C_{1-6}$ alkyl is optionally substituted with one or more halogen, which are the same or different;

$R^{18}$, $R^{18a}$, $R^{18b}$ are independently selected from the group consisting of H; and $C_{1-6}$ alkyl, wherein $C_{1-6}$ alkyl is optionally substituted with one or more halogen, which are the same or different.

2. A compound according to claim 1, wherein of formula (Ia)

(Ia)

wherein X, $T^2$, $R^1$, $R^4$, $R^5$, Rya have the meaning as indicated in claim 1.

3. A compound according to claim 1, wherein of formula (Ib)

(Ib)

wherein X, $T^2$, $R^1$, $R^4$, $R^5$, $R^{5a}$ have the meaning as indicated in claim 1.

4. A compound according to claim 1, wherein X is $NR^6$.

5. A compound according to claim 1, wherein $R^6$ is H or $CH_3$.

6. A compound according to claim 1, wherein $R^1$ is $C(O)R^7$, $C(O)OR^7$, $C(O)N(R^7R^{7a})$ or $C_{1-6}$ alkyl optionally substituted with one or more $R^8$.

7. A compound according to claim 1, wherein $R^7$ is $T^1$; unsubstituted $C_{1-6}$ alkyl; or $C_{1-6}$ alkyl substituted with one $R^8$.

8. A compound according to claim 1, wherein $R^7$ is methyl.

9. A compound according to claim 1, wherein $R^8$ is $T^1$; OH; $OC_{1-6}$ alkyl; $C(O)O$—$C_{1-6}$ alkyl; $C(O)NH_2$; $C(O)NH$—$C_{1-6}$ alkyl; or $C(O)N(C_{1-6}$ alkyl$)_2$.

10. A compound according to claim 1, wherein $T^1$ is unsubstituted $C_{3-7}$ cycloalkyl; unsubstituted non-aromatic heterocyclyl; or unsubstituted aromatic heterocyclyl.

11. A compound according to claim 1, wherein $T^1$ is cyclopropyl; cyclohexyl; furyl; or pyridyl.

12. A compound according to claim 1, wherein $R^{13}$, $R^{13a}$, $R^{13b}$, $R^{13c}$ are H.

13. A compound according to claim 1, wherein $T^2$ is $T^3$.

14. A compound according to claim 1, wherein $T^3$ is unsubstituted or substituted with up to three $R^{14}$, which are the same or different.

15. A compound according to claim 1, wherein $R^{14}$ is oxo (=O), where the ring is at least partially substituted; F; Cl; $N(R^{15}R^{15a})$; $OR^{15}$; $C(O)OR^{15}$; $C(O)N(R^{15}R^{15a})$; $N(R^{15})S(O)_2R^{15a}$; $S(O)_2N(R^{15}R^{15a})$; $S(O)_2R^{15}$; $S(O)R^{15}$; $N(R^{15})C(O)R^{15a}$; or $C_{1-6}$ alkyl, which is optionally substituted with one or more $R^{16}$.

16. A compound according to claim 1, wherein $R^{15}$, $R^{15a}$ are independently selected from the group consisting of H; $CH_3$; $CH_2CH_3$; n-butyl; tert.-butyl; isopropyl; 2-ethylbutyl; $CF_3$; $CH_2CH_2OH$; $CH_2CH_2CH_2OH$; $CH_2C(CH_3)_2CH_2OH$; $CH_2CH_2OCH_3$; $CH_2CH_2NH_2$; $CH_2CH_2CF_3$; $CH_2CH_2NHCH_3$; and $CH_2CH_2N(CH_3)_2$.

17. A compound according to claim 1, wherein $R^{16}$ is F; Cl; Br; OH; $CH_3$; or $CH_2CH_3$.

18. A compound according to claim 1, wherein $R^{14}$ is F; Cl; $NH_2$; $NH(CH_3)$; $N(CH_3)_2$; $NH(CH_2)_2OH$; $N((CH_2)_2OH)_2$; OH; $OCH_3$; $OCF_3$; $OCH(CH_3)_2$; $CH_2OH$; $CH_2OCH_3$; $CH_2Br$; $CH_3$; $CH_2CH_3$; $CH(CH_3)_2$; $C(CH_3)_3$; $CF_3$; $C(O)OH$; $C(O)OCH_3$; $C(O)OCH_2CH_3$; $C(O)NH_2$; $C(O)NH(CH_3)$; $C(O)(CH_3)_2$; $C(O)NHCH_2CH_3$; $C(O)N(CH_3)CH_2CH_3$; $C(O)NHCH_2CH_2OH$; $C(O)N(CH_3)CH_2CH_2OH$; $C(O)NHCH_2CH_2OCH_3$; $C(O)N(CH_3)CH_2CH_2OCH_3$; $C(O)NHCH_2CH_2NH_2$; $C(O)N(CH_3)CH_2CH_2NH_2$; $C(O)NHCH_2CH_2NHCH_3$; $C(O)N(CH_3)CH_2CH_2NHCH_3$; $C(O)NHCH_2CH_2N(CH_3)_2$; $C(O)N(CH_3)CH_2CH_2N(CH_3)_2$; $HNC(O)H_3$; $S(O)_2CH_3$; $S(O)CH_3$; $S(O)_2NH_2$; $S(O)_2NHC(CH_3)_3$; $S(O)_2NHCH_2CH(CH_2CH_3)_2$; $S(O)_2NH(CH_2)_2OH$; $S(O)_2NH(CH_2)_2CF_3$; $S(O)_2NH(CH_2)_3OH$; $S(O)_2NHCH_2C(CH_3)_2CH_2OH$; $S(O)_2NH(CH_2)_2OCH_3$; or $NHS(O)_2CH_3$.

19. A compound according to claim 1 selected from the group consisting of

Cyclopropanecarboxylic acid [5-(2-dimethylamino-phenyl)-[1,2,4]triazolo[1,5-a]pyridin-2-yl]-amide;
Cyclopropanecarboxylic acid [5-(3-chloro-4-fluoro-phenyl)-[1,2,4]triazolo[1,5-a]pyridin-2-yl]-amide;
Cyclopropanecarboxylic acid (5-phenyl-[1,2,4]triazolo[1,5-a]pyridin-2-yl)-amide;
Cyclopropanecarboxylic acid [5-(3-trifluoromethoxy-phenyl)-[1,2,4]triazolo[1,5-a]pyridin-2-yl]-amide;
Cyclopropanecarboxylic acid [5-((E)-styryl)-[1,2,4]triazolo[1,5-a]pyridin-2-yl]-amide;
Cyclopropanecarboxylic acid [5-(3-chloro-phenyl)-[1,2,4]triazolo[1,5-a]pyridin-2-yl]-amide;
Cyclopropanecarboxylic acid (5-thiophen-3-yl-[1,2,4]triazolo[1,5-a]pyridin-2-yl)-amide;
Cyclopropanecarboxylic acid [5-(4-methoxy-phenyl)-[1,2,4]triazolo[1,5-a]pyridin-2-yl]-amide;
3-Cyclohexyl-N-[5-(4-hydroxy-3,5-dimethyl-phenyl)-[1,2,4]triazolo[1,5-a]pyridin-2-yl]-propionamide;
Cyclohexanecarboxylic acid (5-thiophen-3-yl-[1,2,4]triazolo[1,5-a]pyridin-2-yl)-amide;
Furan-2-carboxylic acid [5-(3-fluoro-phenyl)-[1,2,4]triazolo[1,5-a]pyridin-2-yl]-amide;
Furan-2-carboxylic acid [5-(4-hydroxy-3,5-dimethyl-phenyl)-[1,2,4]triazolo[1,5-a]pyridin-2-yl]-amide;
3-Methoxy-N-(5-thiophen-3-yl-[1,2,4]triazolo[1,5-a]pyridin-2-yl)-propionamide;
N-[6-(3-Hydroxymethyl-phenyl)-[1,2,4]triazolo[1,5-a]pyridin-2-yl]-3,3-dimethyl-butyramide;
Cyclopropanecarboxylic acid [6-(2-dimethylamino-phenyl)-[1,2,4]triazolo[1,5-a]pyridin-2-yl]-amide;
N-[6-(4-Hydroxy-phenyl)-[1,2,4]triazolo[1,5-a]pyridin-2-yl]-acetamide;
4-[2-(Cyclopropanecarbonyl-amino)-[1,2,4]triazolo[1,5-a]pyridin-5-yl]-N-(2-dimethylamino-ethyl)-benzamide;
4-[2-(Cyclopropanecarbonyl-amino)-[1,2,4]triazolo[1,5-a]pyridin-5-yl]-N-(2-hydroxy-ethyl)-benzamide;
Cyclopropanecarboxylic acid (5-furan-3-yl-[1,2,4]triazolo[1,5-a]pyridin-2-yl)-amide;
N-[5-(3-Amino-phenyl)-[1,2,4]triazolo[1,5-a]pyridin-2-yl]-3-pyridin-3-yl-propionamide;
Cyclopropanecarboxylic acid [5-(3-methanesulfonylamino-phenyl)-[1,2,4]triazolo[1,5-a]pyridin-2-yl]-amide;
3-[2-(Cyclopropanecarbonyl-amino)-[1,2,4]triazolo[1,5-a]pyridin-6-yl]-N,N-dimethylbenzamide;
N-[6-(3-Methanesulfonylphenyl)-[1,2,4]triazolo[1,5-a]pyridin-2-yl]acetamide;
N-[6-(3-Acetylaminophenyl)-[1,2,4]triazolo[1,5-a]pyridin-2-yl]acetamide;
N-[6-(4-Methoxyphenyl)-[1,2,4]triazolo[1,5-a]pyridin-2-yl]acetamide;
N-[6-(1H-Indol-5-yl)-[1,2,4]triazolo[1,5-a]pyridin-2-yl]acetamide;
N-[6-(1H-Indol-4-yl)-[1,2,4]triazolo[1,5-a]pyridin-2-yl]acetamide;
N-[6-(2,3-Dihydrobenzofuran-5-yl)-[1,2,4]triazolo[1,5-a]pyridin-2-yl]acetamide;
N-[6-(2,4-Dimethoxyphenyl)-[1,2,4]triazolo[1,5-a]pyridin-2-yl]acetamide;
N-(6-Pyridin-3-yl-[1,2,4]triazolo[1,5-a]pyridin-2-yl)acetamide;
N-[6-(5-Methoxypyridin-3-yl)-[1,2,4]triazolo[1,5-a]pyridin-2-yl]acetamide;
N-[6-(4-Methoxy-3-trifluoromethylphenyl)-[1,2,4]triazolo[1,5-a]pyridin-2-yl]acetamide;
N-(6-Pyridin-4-yl-[1,2,4]triazolo[1,5-a]pyridin-2-yl)acetamide;
N-[6-(6-Aminopyridin-3-yl)-[1,2,4]triazolo[1,5-a]pyridin-2-yl]acetamide;
N-[6-(2,3-Dihydrobenzo[1,4]dioxin-6-yl)-[1,2,4]triazolo[1,5-a]pyridin-2-yl]acetamide;
N-[6-(3,4-Dichloro-phenyl)-[1,2,4]triazolo[1,5-a]pyridin-2-yl]-acetamide;
5-(2-Acetylamino-[1,2,4]triazolo[1,5-a]pyridin-6-yl)-2-fluoro-N-(2-hydroxy-ethyl)-benzamide;
N-[6-(3-Dimethylsulfamoyl-phenyl)-[1,2,4]triazolo[1,5-a]pyridin-2-yl]-acetamide;
N-[6-(2,5-Dimethoxy-phenyl)-[1,2,4]triazolo[1,5-a]pyridin-2-yl]-acetamide;
N-[6-(3,4,5-Trimethoxy-phenyl)-[1,2,4]triazolo[1,5-a]pyridin-2-yl]-acetamide;
N-{6-[3-(2-Hydroxy-ethylsulfamoyl)-phenyl]-[1,2,4]triazolo[1,5-a]pyridin-2-yl}-acetamide;
N-[6-(3-Hydroxy-phenyl)-[1,2,4]triazolo[1,5-a]pyridin-2-yl]-acetamide;
N-[6-(2-Methoxy-phenyl)-[1,2,4]triazolo[1,5-a]pyridin-2-yl]-3-methyl-butyramide;
2-Cyclohexyl-N-[6-(2-methoxy-phenyl)-[1,2,4]triazolo[1,5-a]pyridin-2-yl]-acetamide;
2-Methoxy-N-[6-(2-methoxy-phenyl)-[1,2,4]triazolo[1,5-a]pyridin-2-yl]-acetamide;
Furan-2-carboxylic acid [6-(2-methoxy-phenyl)-[1,2,4]triazolo[1,5-a]pyridin-2-yl]-amide;
Isoxazole-5-carboxylic acid [6-(2-methoxy-phenyl)-[1,2,4]triazolo[1,5-a]pyridin-2-yl]amide;
N-[6-(2-Methoxy-phenyl)-[1,2,4]triazolo[1,5-a]pyridin-2-yl]-3-phenyl-propionamide;
N-[6-(6-Methoxy-pyridin-3-yl)-[1,2,4]triazolo[1,5-a]pyridin-2-yl]-acetamide;
N-[6-(5-Methanesulfonyl-pyridin-3-yl)-[1,2,4]triazolo[1,5-a]pyridin-2-yl]-acetamide;
N-[6-(3-Methanesulfonyl-phenyl)-[1,2,4]triazolo[1,5-a]pyridin-2-yl]-2-methoxy-acetamide;
N-[6-(3-Methanesulfonyl-phenyl)-[1,2,4]triazolo[1,5-a]pyridin-2-yl]-propionamide;
Furan-2-carboxylic acid [6-(3-methanesulfonyl-phenyl)-[1,2,4]triazolo[1,5-a]pyridin-2-yl]-amide;
N-[6-(3,4-Dimethoxy-phenyl)-[1,2,4]triazolo[1,5-a]pyridin-2-yl]-acetamide;
N-[6-(3-Methoxyphenyl)-[1,2,4]triazolo[1,5-a]pyridin-2-yl)acetamide;
N-[6-(3-Sulfamoylphenyl)-[1,2,4]triazolo[1,5-a]pyridin-2-yl)acetamide;
3-[2-Acetylamino-[1,2,4]triazolo[1,5-a]pyridin-6-yl)benzamide;
3-[2-Acetylamino-[1,2,4]triazolo[1,5-a]pyridin-6-yl)-N-methylbenzamide;
5-[2-Acetylamino-[1,2,4]triazolo[1,5-a]pyridin-6-yl)-N,N-dimethylbenzamide;
4-[2-Acetylamino-[1,2,4]triazolo[1,5-a]pyridin-6-yl)benzamide;
N-[6-(3-Methylsulfamoylphenyl)-[1,2,4]triazolo[1,5-a]pyridin-2-yl]acetamide;
N-[6-(3-Isopropylsulfamoylphenyl)-[1,2,4]triazolo[1,5-a]pyridin-2-yl]acetamide;
N-[6-(3-tertButylsulfamoylphenyl)-[1,2,4]triazolo[1,5-a]pyridin-2-yl]acetamide;
N-[6-(3-Butylsulfamoylphenyl)-[1,2,4]triazolo[1,5-a]pyridin-2-yl]acetamide;
N-(6-Isoquinolin-6-yl)-[1,2,4]triazolo[1,5-a]pyridin-2-yl)acetamide;

N-[6-(4-Hydroxy-3,5-dimethyl-phenyl)-[1,2,4]triazolo[1,5-a]pyridin-2-yl]-acetamide;
N-[6-(4-Hydroxy-3-methoxy-phenyl)-[1,2,4]triazolo[1,5-a]pyridin-2-yl]-acetamide;
N-[6-(2-Methoxy-phenyl)-[1,2,4]triazolo[1,5-a]pyridin-2-yl]-acetamide;
Cyclopropanecarboxylic acid [6-(6-amino-pyridin-3-yl)-[1,2,4]triazolo[1,5-a]pyridin-2-yl]-amide;
N-[6-(4-Hydroxy-3-methoxy-phenyl)-[1,2,4]triazolo[1,5-a]pyridin-2-yl]-3,3-dimethyl-butyramide;
N-[6-(3-Methanesulfonylamino-phenyl)-[1,2,4]triazolo[1,5-a]pyridin-2-yl]-acetamide;
N-[6-(4-Fluoro-phenyl)-[1,2,4]triazolo[1,5-a]pyridin-2-yl]-acetamide;
N-[6-(3-Methanesulfonyl-phenyl)-[1,2,4]triazolo[1,5-a]pyridin-2-yl]-butyramide;
N-(6-Pyrimidin-5-yl-[1,2,4]triazolo[1,5-a]pyridin-2-yl)-acetamide;
N-[6-(5-Methoxy-pyridin-3-yl)-[1,2,4]triazolo[1,5-a]pyridin-2-yl]-acetamide;
N-[6-(3-Fluoro-phenyl)-[1,2,4]triazolo[1,5-a]pyridin-2-yl]-acetamide;
N-[6-(3,5-Difluoro-phenyl)-[1,2,4]triazolo[1,5-a]pyridin-2-yl]-acetamide;
N-[6-(3-Trifluoromethyl-phenyl)-[1,2,4]triazolo[1,5-a]pyridin-2-yl]-acetamide;
N-{6-[5-(2-Hydroxy-ethylsulfamoyl)-pyridin-3-yl]-[1,2,4]triazolo[1,5-a]pyridin-2-yl}-acetamide;
N-(6-Thiophen-3-yl-[1,2,4]triazolo[1,5-a]pyridin-2-yl)-acetamide;
N-(8-Methyl-6-pyridin-3-yl-[1,2,4]triazolo[1,5-a]pyridin-2-yl)-acetamide;
N-[6-(3-Methanesulfonyl-phenyl)-8-methyl-[1,2,4]triazolo[1,5-a]pyridin-2-yl]-acetamide;
N-[6-(3-Hydroxy-4-methoxy-phenyl)-[1,2,4]triazolo[1,5-a]pyridin-2-yl]-acetamide;
N-[6-(5-Trifluoromethyl-pyridin-3-yl)-[1,2,4]triazolo[1,5-a]pyridin-2-yl]-acetamide;
N-[6-(6-Trifluoromethyl-pyridin-3-yl)-[1,2,4]triazolo[1,5-a]pyridin-2-yl]-acetamide;
N-[6-(4-Chloro-3-methanesulfonyl-phenyl)-[1,2,4]triazolo[1,5-a]pyridin-2-yl]-acetamide;
N-[6-(3-Aminophenyl)-[1,2,4]triazolo[1,5-a]pyridin-2-yl]acetamide;
N-{6-[3-(Methanesulfonylmethylamino)phenyl]-[1,2,4]triazolo[1,5-a]pyridin-2-yl}acetamide;
N-[6-(6-Aminopyridin-3-yl)-[1,2,4]triazolo[1,5-a]pyridin-2-yl]-N-benzamide;
Cyclohexanecarboxylic acid [6-(3-methanesulfonylaminophenyl)-[1,2,4]triazolo[1,5-a]pyridin-2-yl]-amide;
Cyclopropanecarboxylic acid [6-(3-methanesulfonylaminophenyl)-[1,2,4]triazolo[1,5-a]pyridin-2-yl]-amide;
N-[6-(5-(Methanesulfonylaminopyridin-3-yl)-[1,2,4]triazolo[1,5-a]pyridin-2-yl]-N-acetamide;
N-[6-(6-Chloro-5-(Methanesulfonylaminopyridin-3-yl)-[1,2,4]triazolo[1,5-a]pyridin-2-yl]-N-acetamide;
N-[6-(5-Butylsulfamoylpyridin-3-yl)-[1,2,4]triazolo[1,5-a]pyridin-2-yl]acetamide;
3-(2-acetamido-[1,2,4]triazolo[1,5-a]pyridin-6-yl)benzoic acid;
N-(6-(4-(trifluoromethoxy)phenyl)-[1,2,4]triazolo[1,5-a]pyridin-2-yl)acetamide;
N-(6-(3,4-difluorophenyl)-[1,2,4]triazolo[1,5-a]pyridin-2-yl)acetamide;
N-(6-(benzo[d][1,3]dioxol-5-yl)-[1,2,4]triazolo[1,5-a]pyridin-2-yl)acetamide;
4-(2-acetamido-[1,2,4]triazolo[1,5-a]pyridin-6-yl)-N-(2-hydroxyethyl)benzamide;
N-(6-(4-fluoro-3-(trifluoromethyl)phenyl)-[1,2,4]triazolo[1,5-a]pyridin-2-yl)acetamide;
N-(6-(3-fluoro-4-(trifluoromethyl)phenyl)-[1,2,4]triazolo[1,5-a]pyridin-2-yl)acetamide;
N-(6-(3,4-dimethoxy-2-methylphenyl)-[1,2,4]triazolo[1,5-a]pyridin-2-yl)acetamide;
N-(6-(3-isopropoxy-4-methoxyphenyl)-[1,2,4]triazolo[1,5-a]pyridin-2-yl)acetamide;
N-(6-(4-(trifluoromethoxy)-3-(trifluoromethyl)phenyl)-[1,2,4]triazolo[1,5-a]pyridin-2-yl)acetamide;
N-[6-(4-Chloro-2-trifluoromethyl-phenyl)-[1,2,4]triazolo[1,5-a]pyridin-2-yl]-acetamide;
N-[6-(4-Fluoro-3-methoxy-phenyl)-[1,2,4]triazolo[1,5-a]pyridin-2-yl]-acetamide;
N-[6-(3-Methoxy-pyridin-4-yl)-[1,2,4]triazolo[1,5-a]pyridin-2-yl]-acetamide;
N-(6-Isoquinolin-4-yl-[1,2,4]triazolo[1,5-a]pyridin-2-yl)-acetamide;
N-(6-Quinolin-3-yl-[1,2,4]triazolo[1,5-a]pyridin-2-yl)-acetamide;
N-[6-(6-Fluoro-pyridin-3-yl)-[1,2,4]triazolo[1,5-a]pyridin-2-yl]-acetamide;
N-{6-[3-(2-Methoxy-ethylsulfamoyl)-phenyl]-[1,2,4]triazolo[1,5-a]pyridin-2-yl}-acetamide;
N-{6-[3-(3-Hydroxy-propylsulfamoyl)-phenyl]-[1,2,4]triazolo[1,5-a]pyridin-2-yl}-acetamide;
N-(6-{3-[Bis-(2-hydroxy-ethyl)-sulfamoyl]-phenyl}-[1,2,4]triazolo[1,5-a]pyridin-2-yl)-acetamide;
N-{6-[3-(3-Hydroxy-2,2-dimethyl-propylsulfamoyl)-phenyl]-[1,2,4]triazolo[1,5-a]pyridin-2-yl}-acetamide;
N-[6-(5-Sulfamoyl-pyridin-3-yl)-[1,2,4]triazolo[1,5-a]pyridin-2-yl]-acetamide;
N-{6-[5-(3,3,3-Trifluoro-propylsulfamoyl)-pyridin-3-yl]-[1,2,4]triazolo[1,5-a]pyridin-2-yl}-acetamide;
N-[6-(5-tert-Butylsulfamoyl-pyridin-3-yl)-[1,2,4]triazolo[1,5-a]pyridin-2-yl]-acetamide;
N-{6-[5-(2-Ethyl-butylsulfamoyl)-pyridin-3-yl]-[1,2,4]triazolo[1,5-a]pyridin-2-yl}-acetamide;
2-[6-(3,4-Dimethoxy-phenyl)-[1,2,4]triazolo[1,5-a]pyridin-2-ylamino]-ethanol;
N-(5-methyl-6-(5-(methylsulfonyl)pyridin-3-yl)-[1,2,4]triazolo[1,5-a]pyridin-2-yl)acetamide;
N-(8-methyl-6-(5-(methylsulfonyl)pyridin-3-yl)-[1,2,4]triazolo[1,5-a]pyridin-2-yl)acetamide;
N,N-dimethyl-6-(5-(methylsulfonyl)pyridin-3-yl)-[1,2,4]triazolo[1,5-a]pyridin-2-amine;
N-(6-(3,4-dimethoxyphenyl)-5-methyl-[1,2,4]triazolo[1,5-a]pyridin-2-yl)acetamide;
N-(6-(3,4-dimethoxyphenyl)-8-methyl-[1,2,4]triazolo[1,5-a]pyridin-2-yl)acetamide;
1-(2-hydroxyethyl)-3-(6-(5-(methylsulfonyl)pyridin-3-yl)-[1,2,4]triazolo[1,5-a]pyridin-2-yl)urea;
1-(6-(3,4-dimethoxyphenyl)-[1,2,4]triazolo[1,5-a]pyridin-2-yl)-3-(2-hydroxyethyl)urea;
1-(6-(3,4-dimethoxyphenyl)-[1,2,4]triazolo[1,5-a]pyridin-2-yl)-3-methylurea;
6-(3,4-dimethoxyphenyl)-N-methyl-[1,2,4]triazolo[1,5-a]pyridin-2-amine;
Methyl 6-(3,4-dimethoxyphenyl)-[1,2,4]triazolo[1,5-a]pyridin-2-ylcarbamate; and
N-(6-(4-hydroxyphenyl)-[1,2,4]triazolo[1,5-a]pyridin-2-yl)acetamide.

20. A pharmaceutical composition comprising a compound or a pharmaceutically acceptable salt thereof according to claim 1 together with a pharmaceutically acceptable carrier, optionally in combination with one or more other pharmaceutical compositions.

21. A pharmaceutical composition comprising a first compound or a first pharmaceutically acceptable salt thereof according to claim 1, and further comprising one or more additional compounds or pharmaceutically acceptable salts thereof selected from the group consisting of compounds according to claim 1 and not being the same as the first compound or the first pharmaceutically acceptable salt thereof; Itk inhibitors; PI3K inhibitors, steroids, leukotriene antagonsits, anti-histamines, cyclosporine or rapamycin, together with a pharmaceutically acceptable carrier, optionally in combination with one or more other pharmaceutical compositions.

22. A compound or a pharmaceutically acceptable salt thereof according to claim 1 for use as a medicament.

23. A method for treating or controlling in a mammalian patient in need of the treatment of one or more conditions selected from the group consisting of autoimmune diseases; organ and bone marrow transplant rejection; graft-versus-host disease; acute or chronic inflammation; contact dermatitis; psoriasis; rheumatoid arthritis; multiple sclerosis; type I diabetes; inflammatory bowel disease; Crohn's disease; ulcerative colitis; lupus erythematosus; asthma; chronic obstructive pulmonary disease (COPD); acute respiratory distress syndrome (ARDS); bronchitis; conjunctivitis; dermatitis; and allergic rhinitis, wherein the method comprises the administration to said patient a therapeutically effective amount of a compound according to claim 1 or a pharmaceutically acceptable salt thereof.

24. A method for treating or controlling in a mammalian patient in need of the treatment of one or more conditions selected from the group consisting of colorectal cancer; brain cancer; gastric cancer; breast cancer; lung cancer; acute myeloid leukemia (AML); myocardial infarction (MI); and hypertension, wherein the method comprises the administration to said patient a therapeutically effective amount of a compound according to claim 1 or a pharmaceutically acceptable salt thereof.

25. A process for the preparation of a compound according to claim 1, comprising the step of
(a) reacting a triazole of formula (II)

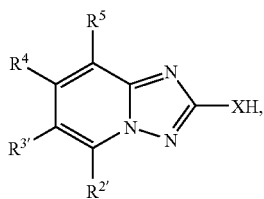

II wherein one of $R^{2'}$, $R^{3'}$ is Br and the other is $R^{5a}$, and X, $R^4$, $R^5$ have the meaning as indicated in claim 1 with $R^1$—X', wherein X is a suitable leaving group for the substitution reaction with the residue XH and $R^1$ has the meaning as indicated in claim 1 to yield triazole of formula (III)

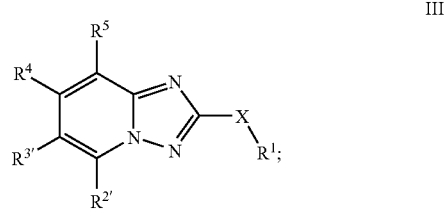

III and
(b) reacting triazole (III) with boronic acid $T^2$-B(OH)$_2$ in a Suzuki reaction to give compounds of formula (I).

26. The process according to claim 25, wherein a triazole of formula (II), wherein X is NH is prepared by reacting a pyridine of formula (IV)

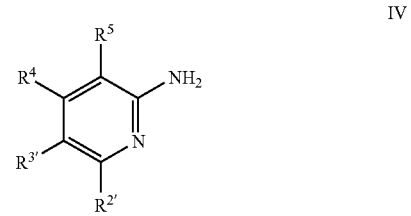

IV with ethoxycarbonyl isothiocyanate to yield after cyclisation in the presence of hydroxylamine the triazole of formula (II).

27. The process according to claim 25, wherein a triazole of formula (III), wherein X is NH and $R^1$ is C(O)$R^7$ is prepared by reacting a triazole of formula (II) with an acid chloride $R^7$—C(O)Cl to yield after optional partial hydrolysis of the respective bis-acylated by-product a triazole of formula (III).

* * * * *